US008722205B2

(12) United States Patent
Xia et al.

(10) Patent No.: US 8,722,205 B2

(45) Date of Patent: May 13, 2014

(54) HETEROLEPTIC IRIDIUM COMPLEX

(75) Inventors: Chuanjun Xia, Lawrenceville, NJ (US); Raymond Kwong, Plainsboro, NJ (US); Suman Layek, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 300 days.

(21) Appl. No.: 12/727,615

(22) Filed: Mar. 19, 2010

(65) Prior Publication Data

US 2010/0244004 A1 Sep. 30, 2010

Related U.S. Application Data

(60) Provisional application No. 61/162,476, filed on Mar. 23, 2009.

(51) Int. Cl.
*H01L 51/54* (2006.01)
*C09K 11/06* (2006.01)

(52) U.S. Cl.
USPC .... 428/690; 428/917; 313/504; 257/E51.044; 546/4

(58) Field of Classification Search
None
See application file for complete search history.

(56) References Cited

U.S. PATENT DOCUMENTS

| | | | | |
|---|---|---|---|---|
| 4,769,292 | A | 9/1988 | Tang et al. | |
| 5,061,569 | A | 10/1991 | VanSlyke et al. | |
| 5,247,190 | A | 9/1993 | Friend et al. | |
| 5,703,436 | A | 12/1997 | Forrest et al. | |
| 5,707,745 | A | 1/1998 | Forrest et al. | |
| 5,834,893 | A | 11/1998 | Bulovic et al. | |
| 5,884,363 | A | 3/1999 | Tofts | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A | 8/2000 | Baldo et al. | |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,279,704 | B2 | 10/2007 | Walters et al. | |
| 2002/0034656 | A1 | 3/2002 | Thompson et al. | |
| 2002/0134984 | A1 | 9/2002 | Igarashi | |
| 2003/0059646 | A1 * | 3/2003 | Kamatani et al. | 428/690 |
| 2003/0175553 | A1 | 9/2003 | Thompson et al. | |
| 2003/0230980 | A1 | 12/2003 | Forrest et al. | |
| 2004/0013905 | A1 | 1/2004 | Tsuboyama et al. | |
| 2004/0174116 | A1 | 9/2004 | Lu et al. | |
| 2005/0025993 | A1 | 2/2005 | Thompson et al. | |
| 2005/0234240 | A1 | 10/2005 | Stossel et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0251923 | A1 | 11/2006 | Lin et al. | |
| 2006/0280965 | A1 | 12/2006 | Kwong et al. | |
| 2006/0287498 | A1 | 12/2006 | Morishita et al. | |
| 2007/0128466 | A1 | 6/2007 | Nomura et al. | |
| 2007/0190359 | A1 | 8/2007 | Knowles et al. | |

FOREIGN PATENT DOCUMENTS

| | | | |
|---|---|---|---|
| CN | 1680366 | A | 10/2005 |
| CN | 100348594 | C | 11/2007 |
| EP | 0650955 | | 5/1995 |
| EP | 1 238 981 | | 9/2002 |
| EP | 1 820 801 | | 8/2007 |
| JP | 200511610 | | 1/2005 |
| JP | 2006-179895 | | 7/2006 |
| JP | 2007123392 | | 5/2007 |
| JP | 2007254297 | | 10/2007 |
| JP | 2008-010653 | | 1/2008 |
| WO | WO 01/39234 | | 5/2001 |

(Continued)

OTHER PUBLICATIONS

Baldo et al., "Highly Efficient Phosphorescent Emission from Organic Electroluminescent Devices," Nature, vol. 395, 151-154, 1998; ("Baldo-I").

(Continued)

*Primary Examiner* — Marie R. Yamnitzky
(74) *Attorney, Agent, or Firm* — Duane Morris LLP

(57) ABSTRACT

Novel compounds comprising heteroleptic iridium complexes are provided. The compounds have a particular combination of ligands which includes a single pyridyl dibenzo-substituted ligand as exemplified by Formula I, where X is NR, O, S, BR, or Se. The compounds may be used in organic light emitting devices, particularly as emitting dopants, to provide devices having improved efficiency, lifetime, and manufacturing.

Formula I

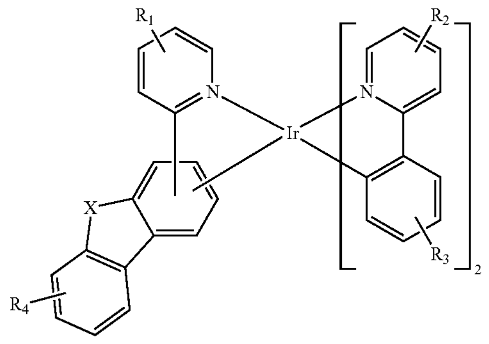

39 Claims, 3 Drawing Sheets

(56) References Cited

FOREIGN PATENT DOCUMENTS

| | | |
|---|---|---|
| WO | WO 02/02714 | 1/2002 |
| WO | WO 03040257 | 5/2003 |
| WO | WO 03060956 | 7/2003 |
| WO | WO 2004093207 | 10/2004 |
| WO | 2004/111068 | 12/2004 |
| WO | WO 2004107822 | 12/2004 |
| WO | WO 2005014551 | 2/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006082742 | 8/2006 |
| WO | WO 2006098120 | 9/2006 |
| WO | WO 2006103874 | 10/2006 |
| WO | WO 2006114966 | 11/2006 |
| WO | WO 2006132173 | 12/2006 |
| WO | WO 2007004380 | 1/2007 |
| WO | WO 2007063754 | 6/2007 |
| WO | WO 2007063796 | 6/2007 |
| WO | 2008-073440 | 6/2008 |
| WO | WO 2009/021126 A2 * | 2/2009 |

OTHER PUBLICATIONS

Baldo et al., "Very high-efficiency green organic light-emitting devices based on electrophosphorescence," Appl. Phys. Lett., vol. 75, No. 1, 4-6 (1999) ("Baldo-II").

Kuwabara, Yoshiyuki et al., "Thermally Stable Multilayered Organic Electroluminescent Devices Using Novel Starburst Molecules, 4,4',4"-Tri(*N*-carbazolyl)triphenylamine (TCTA) and 4,4',4"-Tris(3-methylphenylphenyl-amino)triphenylamine (*m*-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-*C*2,*N*)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(*I*) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1—153505-3 (2005).

Okumoto, Kenji et al., "Green Fluorescent Organic Light-Emitting Device with External Quantum Efficiency of Nearly 10%," *Appl. Phys. Lett.*, 89:063504-1—063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1—123509-3 (2007).

Aonuma, Masaki et al., "Material Design of Hole Transport Materials Capable of Thick-Film Formation in Organic Light Emitting Diodes," *Appl. Phys. Lett.*, 90:183503-1—183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1—263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al. "A Novel Class of Phosphorescent Gold(III) Alkynyl-Based Organic Light-Emitting Devices with Tunable Colour," *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

(56) References Cited

OTHER PUBLICATIONS

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

C. Yang et al., "Tuning the energy level and photophysical and electroluminescent properties of heavy metal complexes by controlling the ligation of the metal with the carbon of the carbazole unit", *Adv. Funct. Mater*. 2007, 17, pp. 651-661.

S. Bettington et al., "Tris-cyclometalated iridium (III) complexes of carbazole (fluorenyl) pyridine ligands: synthesis, redox and photophysical properties, and electrophosphorescent light-emitting diodes", Chem. Eur. J. 2007, 13, pp. 1423-1431.

K. Zhang et al., "Improving the performance of phosphorescent polymer light-emitting diodes using morphology-stable carbazole-based iridium complexes", J. Mater. Chem. 2007, 17, pp. 3451-3460.

Tao et al., "Solution-processable highly efficient yellow-and red-emitting phosphorescent organic light emitting devices from a small molecule bipolar host and iridium complexes", J. Mater. Chem. 2008, 18, pp. 4091-4096.

The Search Report and Written Opinion corresponding to the PCT/US2010/028134 application, (dated Jun. 21, 2010).

* cited by examiner

HETEROLEPTIC IRIDIUM COMPLEX

This application claims priority to U.S. Provisional Application No. 61/162,476, filed Mar. 23, 2009, the disclosure of which is herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic complexes that may be advantageously used in organic light emitting devices. More particularly, the present invention relates to novel heteroleptic iridium complexes containing a pyridyl dibenzo-substituted ligand and devices containing these compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

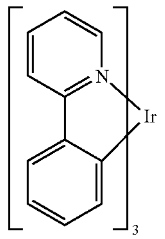

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Novel phosphorescent emissive compounds are provided. The compounds comprise heteroleptic iridium complexes having the formula:

FORMULA I

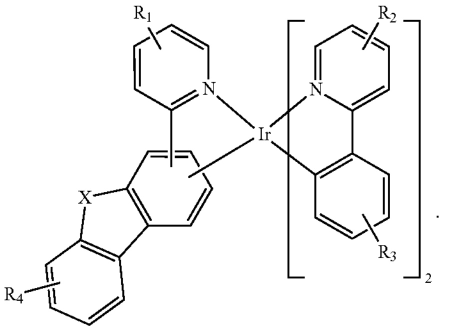

The compound comprises a ligand having the structure

FORMULA II

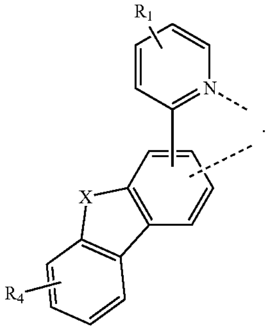

X is selected from the group consisting of NR, O, S, BR, and Se. R is selected from hydrogen and alkyl. Preferably, R has 4 or fewer carbon atoms. $R_1$, $R_2$, $R_3$, and $R_4$ may represent mono, di, tri, or tetra substitutions. Each of $R_1$, $R_2$, $R_3$, and $R_4$ are independently selected from the group consisting of hydrogen, alkyl, and aryl. Preferably, alkyls in the $R_1$, $R_2$, $R_3$ and/or $R_4$ positions of Formula I have four or fewer carbon atoms (e.g., methyl, ethyl, propyl, butyl, and isobutyl). Preferably, $R_1$ and $R_4$ are independently hydrogen or alkyl having four or fewer carbon atoms; more preferably, $R_1$ and $R_4$ are independently hydrogen or methyl. Preferably, $R_2$ and $R_3$ are independently hydrogen or alkyl having four or fewer carbon atoms; more preferably, $R_2$ and $R_3$ are independently hydrogen or methyl; most preferably, $R_2$ and $R_3$ are hydrogen.

Preferably, $R_1$ and $R_4$ are independently hydrogen, alkyl having four or fewer carbon atoms or aryl with 6 or fewer atoms in the ring; more preferably, $R_1$ and $R_4$ are independently hydrogen, methyl or phenyl. Preferably, $R_2$ and $R_3$ are independently hydrogen, alkyl having four or fewer carbon atoms or aryl with 6 or fewer atoms in the ring; more preferably, $R_2$ and $R_3$ are independently hydrogen, methyl or phenyl; most preferably, $R_2$ and $R_3$ are hydrogen.

In one aspect, compounds are provided wherein $R_1$, $R_2$, $R_3$, and $R_4$ are independently selected from the group consisting of hydrogen and alkyl having four or fewer carbon atoms. In another aspect, compounds are provided wherein $R_1$, $R_2$, $R_3$, and $R_4$ are independently selected from the group consisting of hydrogen and methyl. In yet another aspect, compounds are provided wherein $R_1$, $R_2$, $R_3$, and $R_4$ are hydrogen.

In another aspect, compounds are provided wherein $R_1$, $R_2$, $R_3$, and $R_4$ are independently selected from the group consisting of hydrogen, alkyl having four or fewer carbon atoms and aryl with 6 or fewer atoms in the ring. In another aspect, compounds are provided wherein $R_1$, $R_2$, $R_3$, and $R_4$ are independently selected from the group consisting of hydrogen, methyl and phenyl. In yet another aspect, compounds are provided wherein $R_1$, $R_2$, $R_3$, and $R_4$ are hydrogen.

Particular heteroleptic iridium complexes are also provided. In one aspect, heteroleptic iridium complexes are provided having the formula:

FORMULA III

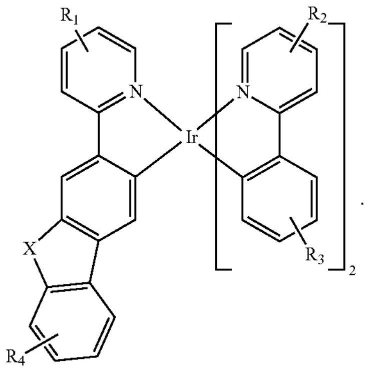

In another aspect, heteroleptic iridium complexes are provided having the formula:

FORMULA IV

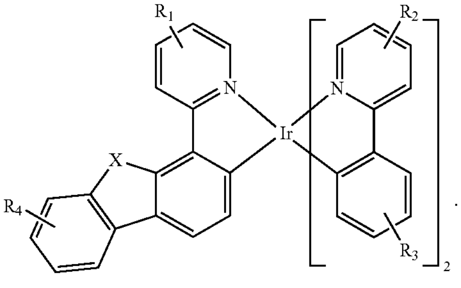

In yet another aspect, heteroleptic iridium complexes are provided having the formula:

FORMULA V

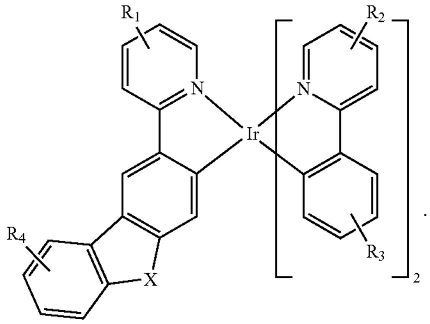

Specific examples of heteroleptic iridium complex are provided including Compounds 1-36. In particular, heteroleptic compounds are provided wherein X is O (i.e., pyridyl dibenzofuran), for example, Compounds 1-12. Additionally, heteroleptic compounds are provided wherein X is S (i.e., pyridyl dibenzothiophene), for example, Compounds 13-24. Moreover, heteroleptic compounds are provided wherein X is NR (i.e., pyridyl carbazole), for example, Compounds 25-36.

Additional specific examples of heteroleptic iridium complexes are provided, including Compounds 37-108. In particular, heteroleptic compounds are provided wherein X is O, for example, Compounds 37-60. Further, heteroleptic compounds are provided wherein X is S, for example, Compounds 61-84. Moreover, heteroleptic compounds are provided wherein X is NR, for example, Compounds 85-108.

Additionally, an organic light emitting device is also provided. The device has an anode, a cathode, and an organic layer disposed between the anode and the cathode, where the organic layer comprises a compound having FORMULA I. In particular, the organic layer of the device may comprise a compound selected from Compounds 1-36. The organic layer may further comprise a host. Preferably, the host contains a triphenylene moiety and a dibenzothiophene moiety. More preferably, the host has the formula:

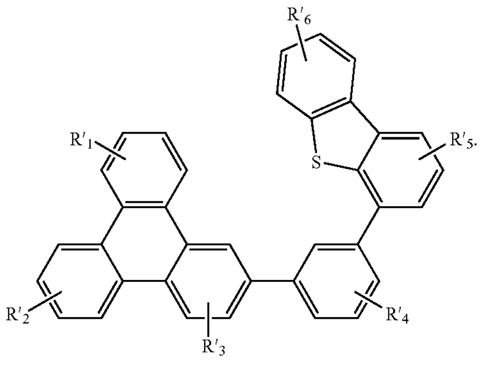

$R'_1$, $R'_2$, $R'_3$, $R'_4$, $R'_5$, and $R'_6$ may represent mono, di, tri, or tetra substitutions. $R'_1$, $R'_2$, $R'_3$, $R'_4$, $R'_5$, and $R'_6$ are independently selected from the group consisting of hydrogen, alkyl, and aryl.

The organic layer of the device may comprise a compound selected from the group consisting of Compounds 1-108. In particular, the organic layer of the device may also comprise a compound selected from Compounds 37-108.

A consumer product comprising a device is also provided. The device contains an anode, a cathode, and an organic layer disposed between the anode and the cathode, where the organic layer further comprises a compound having FORMULA I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
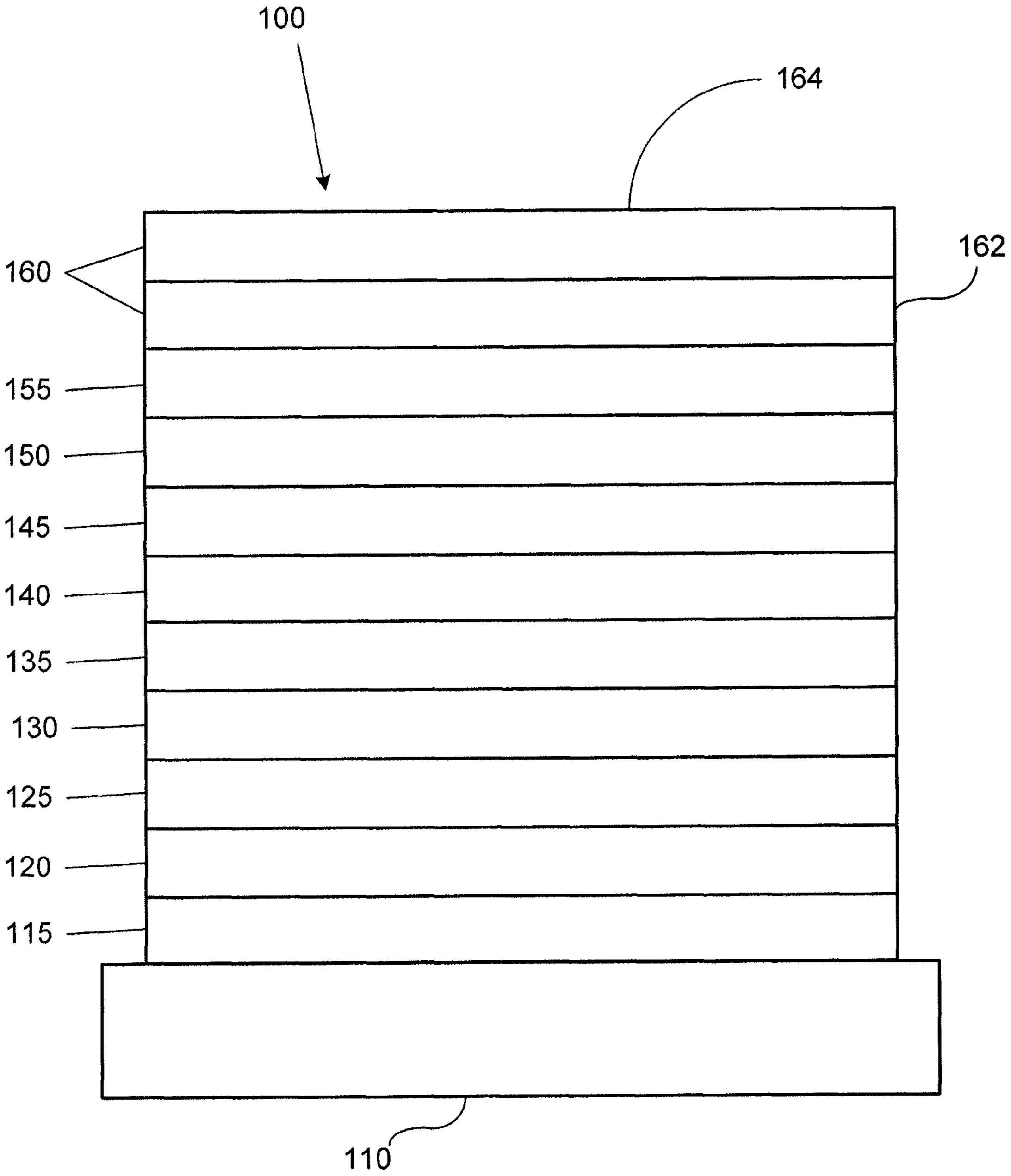
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
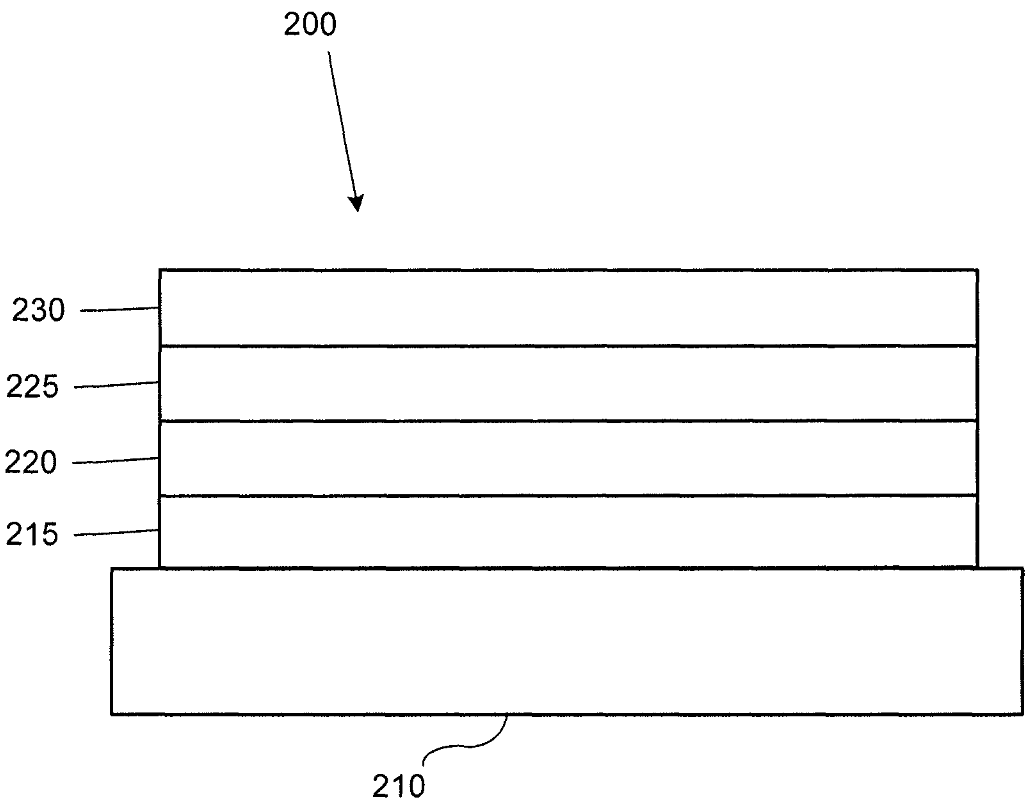
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
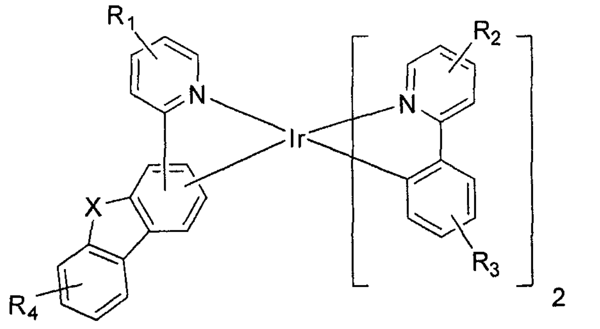
FIG. 3 shows a heteroleptic iridium complex.

Novel compounds are provided, the compounds comprising a heteroleptic iridium complex (illustrated in FIG. 3). In particular, the complex has two phenylpyridine ligands and one ligand having the structure

FORMULA II

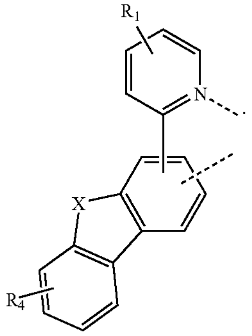

The ligand having the structure FORMULA II consists of a pyridine joined to a dibenzofuran, dibenzothiophene, carbazole, dibenzoborole, or dibenzoselenophene (herein also referred to as "pyridyl dibenzo-substituted"). These compounds may be advantageously used in organic light emitting devices as an emitting dopant in an emissive layer.

Iridium complexes containing two or three pyridyl dibenzofuran, dibenzothiophene, carbazole, and fluorene ligands have been reported. By replacing the phenyl group in tris(2-phenylpyridine)iridium with dibenzofuran, dibenzothiophene, carbazole, and fluorene groups, the HOMO-LUMO energy levels, photophysical properties, and electronic properties of the resulting complex can be significantly affected. A variety of emission colors, ranging from green to red, have been achieved by using complexes with different combinations of pyridyl dibenzo-substituted ligands (i.e., bis and tris complexes). However, the existing complexes may have practical limitations. For example, iridium complexes having two or three of these types of ligands (e.g., pyridyl dibenzofuran, dibenzothiophene, or carbazole) have high molecular weights, which often results in a high sublimation temperature. In some instances, these complexes can become non-sublimable due to the increased molecular weight. For example, tris(2-(dibenzo[b,d]furan-4-yl)pyridine)Iridium(III) decomposed during sublimation attempts. Additionally, known compounds comprising a pyridyl fluorene ligand may have reduced stability. Fluorene groups (e.g., C═O and CRR') disrupt conjugation within the ligand structure resulting in a diminished ability to stabilize electrons. Therefore, compounds with the beneficial properties of pyridyl dibenzo-substituted ligands (e.g., dibenzofuran, dibenzothiophene, carbazole, dibenzoborole, and dibenzoselenophene) and a relatively low sublimation temperature are desirable.

Additionally, iridium complexes having two or three of the ligands having FORMULA II have high molecular weights and stronger intermolecular interactions, which often results in a high sublimation temperature. In some instances, these complexes can become non-sublimable due to the increased molecular weight and strong intermolecular interactions.

Novel heteroleptic iridium complexes are provided herein. The complexes contain pyridyl dibenzo-substituted ligands having the structure FORMULA II. In particular, the novel heteroleptic complexes include a single pyridyl dibenzo-substituted ligand wherein the ligand contains O, S, N, Se, or B (i.e. the ligand is pyridyl dibenzofuran, pyridyl dibenzothiophene, pyridyl carbazole, pyridyl dibenzoselenophene, or pyridyl dibenzoborole) and two phenylpyridine ligands. As a result of the particular combination of ligands in the heteroleptic compounds disclosed herein, these compounds can provide both improved photochemical and electrical properties as well as improved device manufacturing. In particular, by containing only one of the dibenzo-substituted pyridine ligands having FORMULA II, the complexes provided herein will likely have lower sublimation temperatures (correlated with reduced molecular weight and/or weaker intermolecular interactions). Additionally, these compounds maintain all of the benefits associated with the pyridyl dibenzo-substituted ligand, such as improved stability, efficiency, and narrow line width. Therefore, these compounds may be used to provide improved organic light emitting devices and improved commercial products comprising such devices. In particular, these compounds may be particularly useful in red and green phosphorescent organic light emitting devices (PHOLEDs).

As mentioned previously, bis or tris iridium complexes containing ligands having FORMULA II may be limited in practical use due to the high sublimation temperature of the complex. The invention compounds, however, have a lower sublimation temperature which can improve device manufacturing. Table 1 provides the sublimation temperature for several compounds provided herein and the corresponding bis or tris complex. For example, Compound 1 has a sublimation temperature of 243° C. while the corresponding tris complex fails to sublime. Additionally, other tris complexes comprising three pyridyl dibenzo-substituted ligands (i.e., tris complex comprising pyridyl dibenzothiophene) fail to sublime. Therefore, the compounds provided herein may allow for improved device manufacturing as compared to previously reported bis and tris compounds.

TABLE 1

| Compounds | Sublimation temperature (° C.) |
|---|---|
| 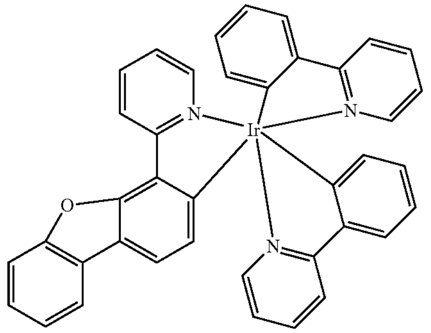 Compound 1 | 243 |
| 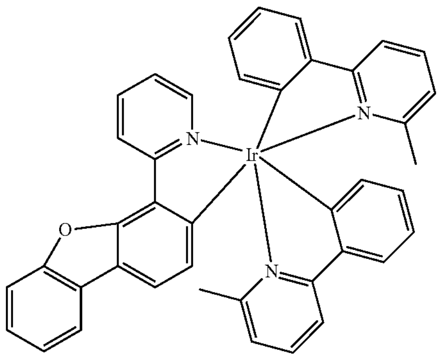 Compound 4 | 218 |

TABLE 1-continued
| Compounds | Sublimation temperature (° C.) |
|---|---|
| 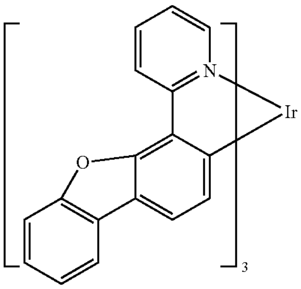 | Fail to sublime |
| 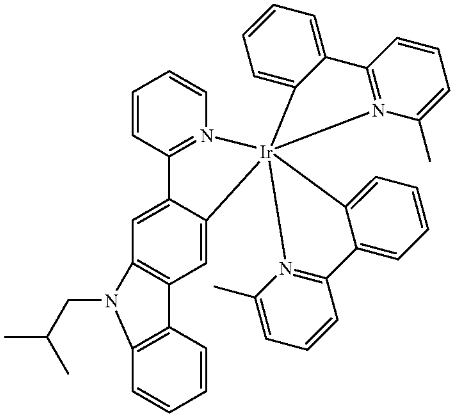 Compound 29 | 230 |
| 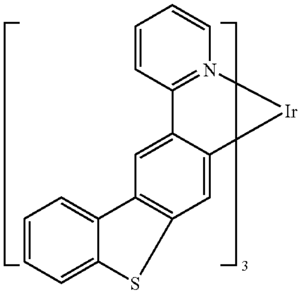 | Fail to sublime |
| 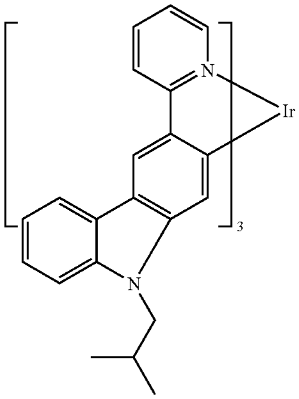 | 290 |
TABLE 1-continued
| Compounds | Sublimation temperature (° C.) |
|---|---|
| 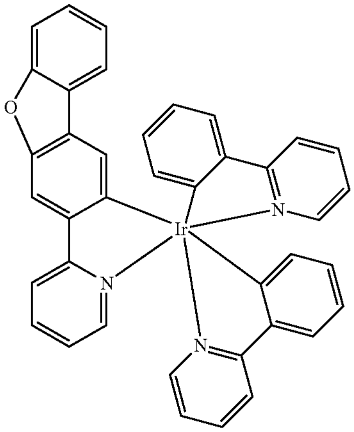 Compound 2 | 232 |
| 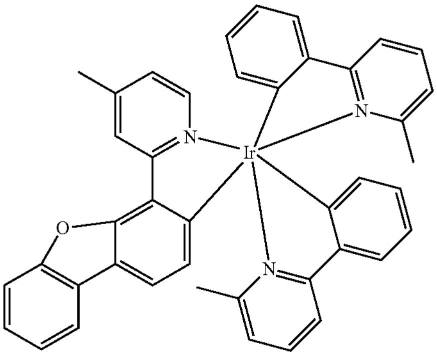 Compound 10 | 240 |
| 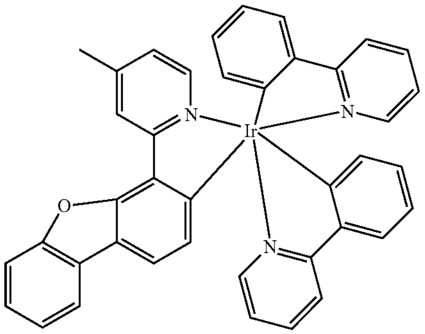 Compound 7 | 256 |

TABLE 1-continued

| Compounds | Sublimation temperature (° C.) |
|---|---|
| 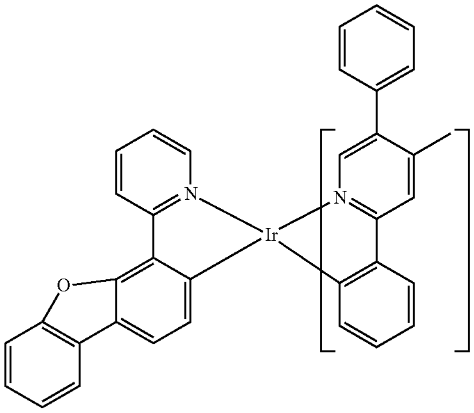 Compound 37 | 224 |

Generally, the dibenzo-substituted pyridine ligand would be expected to have lower triplet energy than the phenylpyridine ligand, and consequently the dibenzo-substituted pyridine ligand would be expected to control the emission properties of the compound. Therefore, modifications to the dibenzo-substituted pyridine ligand may be used to tune the emission properties of the compound. The compounds disclosed herein contain a dibenzo-substituted pyridine ligand containing a heteroatom (e.g., O, S, or NR) and optionally further substituted by chemical groups at the $R_1$ and $R_4$ positions. Thus, the emission properties of the compounds may be tuned by selection of a particular heteroatom and/or varying the substituents present on the dibenzo-substituted pyridine ligand.

The compounds described herein comprise heteroleptic iridium complexes having the formula:

FORMULA I

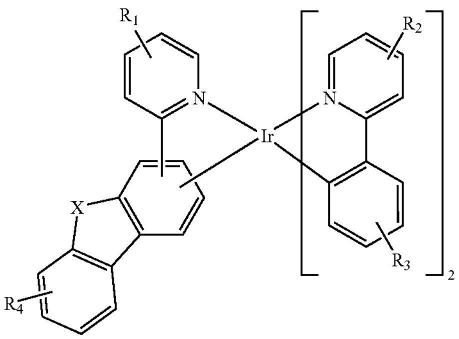

Features of the compounds having FORMULA I include comprising one ligand having the structure

FORMULA II

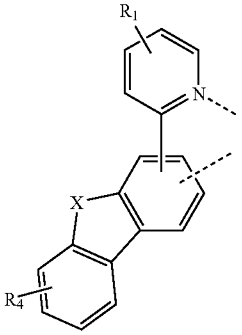

and two phenylpyridine ligands that may have further substitution, wherein all ligands are coordinated to Ir.

X is selected from the group consisting of NR, O, S, BR, and Se. R is selected from hydrogen and alkyl. $R_1$, $R_2$, $R_3$ and $R_4$ may represent mono, di, tri, or tetra substitutions; and each of $R_1$, $R_2$, $R_3$ and $R_4$ are independently selected from the group consisting of hydrogen, alkyl having four or fewer carbon atoms, and aryl.

In another aspect, $R_1$, $R_2$, $R_3$ and $R_4$ are independently selected from the group consisting of hydrogen, alkyl having four or fewer carbon atoms, and aryl with 6 or fewer atoms in the ring.

The term "aryl" as used herein refers to an aryl, comprising either carbon atoms or heteroatoms, that is not fused to the phenyl ring of the phenylpyridine ligand (i.e., aryl is a non-fused aryl). The term "aryl" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls. Additionally, the aryl group may be optionally substituted with one or more substituents selected from halo, CN, $CO_2R$, C(O)R, $NR_2$, cyclic-amino, $NO_2$, and OR. "Aryl" also encompasses a heteroaryl, such as single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. This includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Additionally, the heteroaryl group may be optionally substituted with one or more substituents selected from halo, CN, $CO_2R$, C(O)R, $NR_2$, cyclic-amino, $NO_2$, and OR. For example, $R_1$, $R_2$, $R_3$ and/or $R_4$ may be an aryl, including an heteroaryl, that is not used to the phenyl ring of the phenylpyridine.

The term "alkyl" as used herein contemplates both straight and branched chain alkyl radicals. Examples include methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR, wherein each R is independently selected from H, alkyl, alkenyl, alkynyl, aralkyl, aryl and heteroaryl. Preferably, in order to make the compounds sublimable and/or to reduce sublimation temperature, alkyls in the $R_1$, $R_2$, $R_3$ and/or $R_4$ positions of Formula I have four or fewer carbon atoms (e.g., methyl, ethyl, propyl, butyl, and isobutyl).

In general, the compounds provided herein have relatively low sublimation temperatures compared to previously reported compounds. Thus, these novel compounds provide improved device fabrication among other beneficial properties. Moreover, it is believed that heteroleptic compounds having FORMULA I wherein $R_1$, $R_2$, $R_3$ and $R_4$ are selected from smaller substituents may be particularly beneficial. A smaller substituents includes, for example, hydrogen or alkyl. In particular, it is believed that compounds wherein the substituents $R_1$, $R_2$, $R_3$ and/or $R_4$ are selected from smaller substituents may have even lower sublimation temperatures thereby further improving manufacturing while maintaining the desirable properties (e.g., improved stability and lifetimes) provided by the ligand having the structure FORMULA II.

Generally, the compounds provided having FORMULA I have substituents such that $R_1$, $R_2$, $R_3$ and $R_4$ are independently selected from the group consisting of hydrogen, alkyl, and aryl. Preferably, any alkyl has four or fewer carbon atoms. To minimize molecular weight and thereby lower the sublimation temperature, compounds having smaller substituents on the ligand having the structure FORMULA II are preferred. Preferably, $R_1$ and $R_4$ are independently selected from the group consisting of hydrogen and alkyl having four or fewer carbon atoms; more preferably, $R_1$ and $R_4$ are independently selected from the group consisting of hydrogen and methyl.

For similar reasons, compounds are preferred having smaller substituents present on the phenylpyridine ligand. Additionally, the phenylpyridine ligand is believed to contribute less to the emission of the complex. Moreover, the complex contains two of the phenylpyridine ligand, thus substituents present on the phenylpyridine ligand contribute more to the overall molecular weight of the complex. For at least these reasons, preferably $R_2$ and $R_3$ are independently selected from hydrogen and alkyl having four or fewer carbon atoms; more preferably, $R_2$ and $R_3$ are independently selected from hydrogen and methyl; most preferably, $R_2$ and $R_3$ are hydrogen.

Compounds having alkyl and aryl substitutions that can decrease intermolecular interactions are also preferred.

In another aspect, preferably $R_2$ and $R_3$ are independently selected from hydrogen, alkyl having four or fewer carbon atoms and aryl with 6 or fewer atoms in the ring; more preferably, $R_2$ and $R_3$ are independently selected from hydrogen, methyl and phenyl; most preferably, $R_2$ and $R_3$ are hydrogen.

Compounds are preferred wherein the overall molecular weight of the complex is low to reduce the sublimation temperature and improve device manufacturing. Toward this end, compounds wherein all substituents are relatively small are preferred. In one aspect, preferably $R_1$, $R_2$, $R_3$ and $R_4$ are independently selected from the group consisting of hydrogen and alkyl having four or fewer carbon atoms; more preferably, $R_1$, $R_2$, $R_3$ and $R_4$ are independently selected from the group consisting of hydrogen and methyl; most preferably, $R_1$, $R_2$, $R_3$ and $R_4$ are hydrogen.

In another aspect, preferably $R_1$, $R_2$, $R_3$ and $R_4$ are independently selected from the group consisting of hydrogen, alkyl having four or fewer carbon atoms and aryl with 6 or fewer atoms in the ring; more preferably, $R_1$, $R_2$, $R_3$ and $R_4$ are independently selected from the group consisting of hydrogen, methyl and phenyl; most preferably, $R_1$, $R_2$, $R_3$ and $R_4$ are hydrogen.

As discussed above, X can also be BR. Preferably, R has 4 or fewer carbon atoms. For similar reasons as those previously discussed, smaller alkyl groups (i.e., alkyls having 4 or fewer carbon atoms) on the carbazole portion of the substituted ligand will likely lower the sublimation temperature of the complex and thus improve device manufacturing.

Particular heteroleptic iridium complexes are also provided. In one aspect, heteroleptic iridium complexes are provided having the formula:

FORMULA III

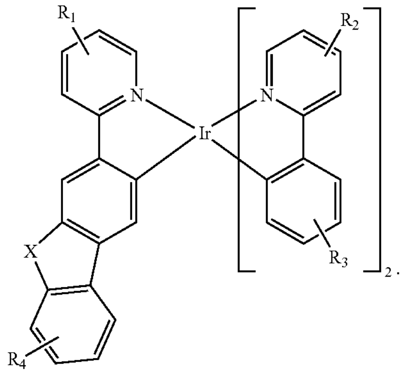

In another aspect, heteroleptic iridium complexes are provided having the formula:

FORMULA IV

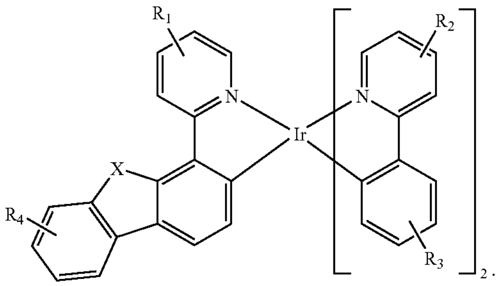

In yet another aspect, heteroleptic iridium complexes are provided having the formula:

FORMULA V

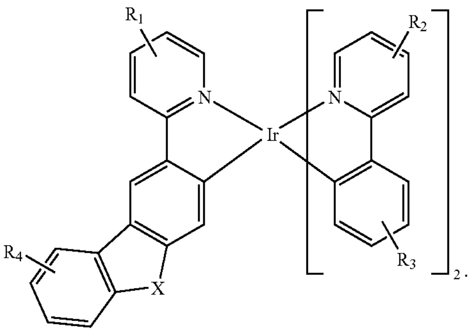

Specific examples of heteroleptic iridium complexes are provided, and include compounds selected from the group consisting of:

Compound 1
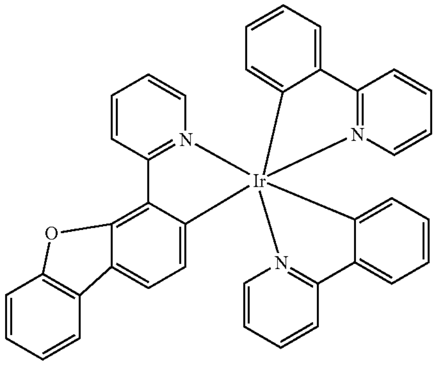
Compound 2
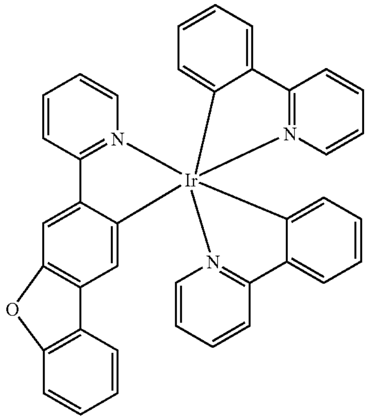
Compound 3
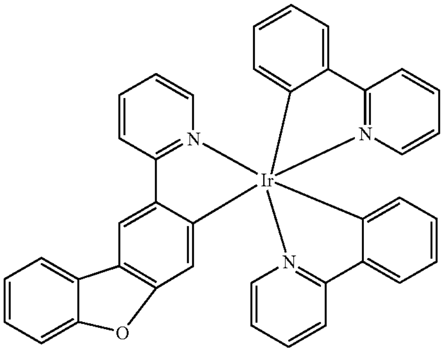
Compound 4
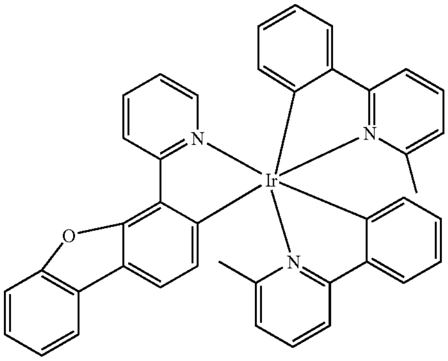
-continued
Compound 5
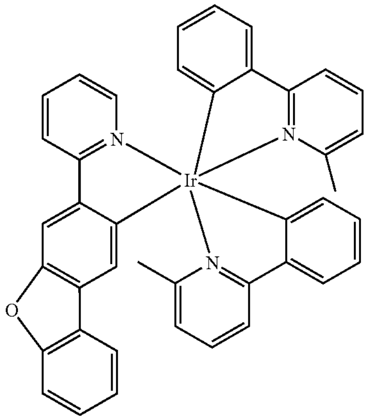
Compound 6
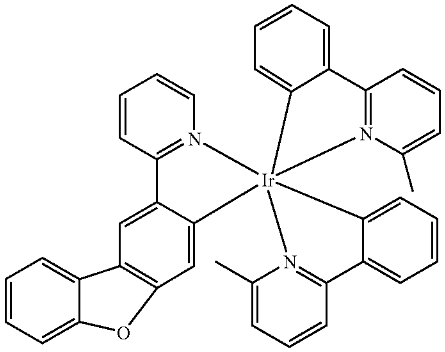
Compound 7
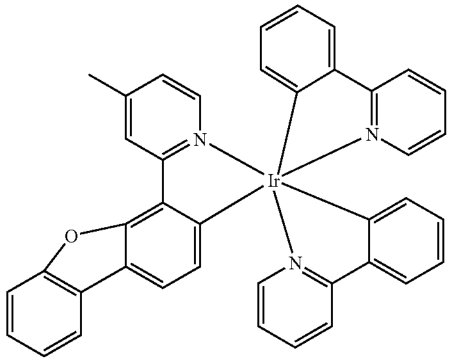
Compound 8
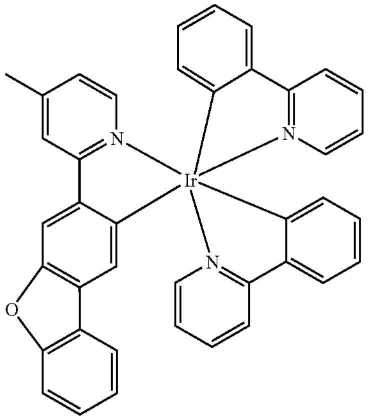

-continued
Compound 9
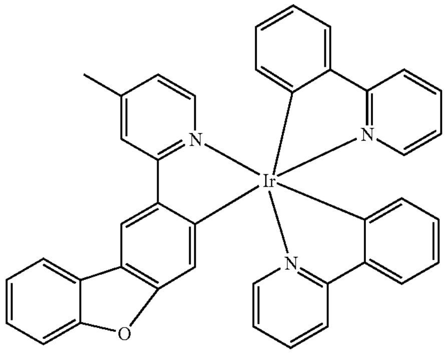
Compound 10
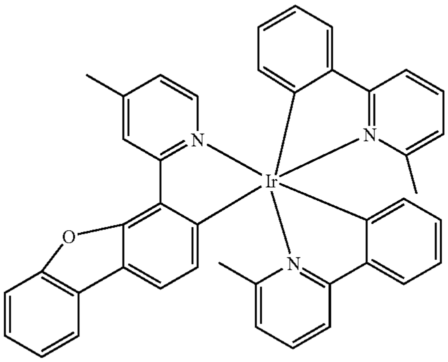
Compound 11
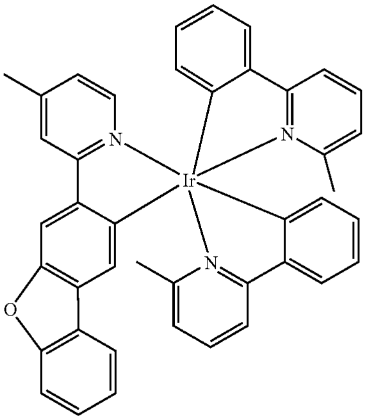
Compound 12
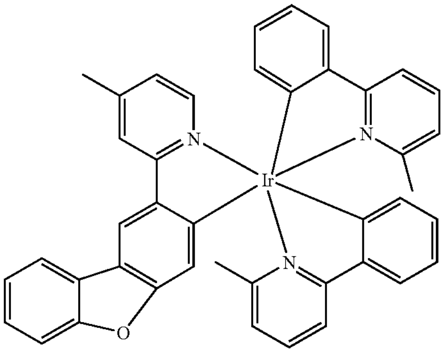
-continued
Compound 13
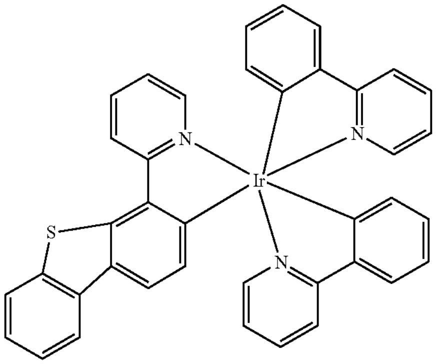
Compound 14
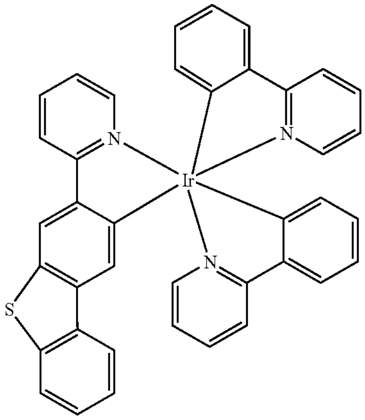
Compound 15
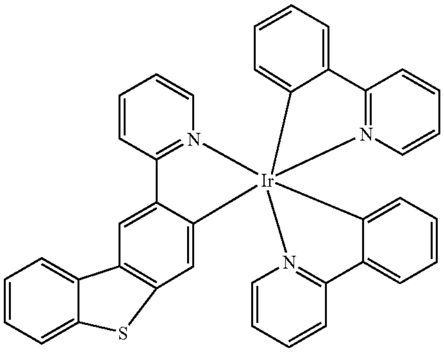
Compound 16
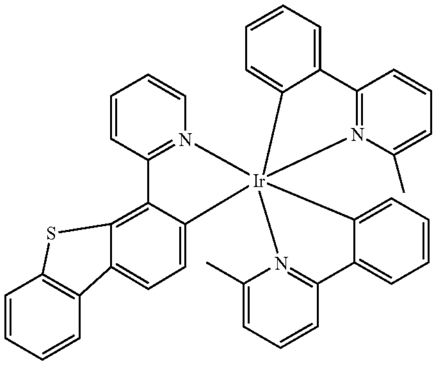

-continued
Compound 17
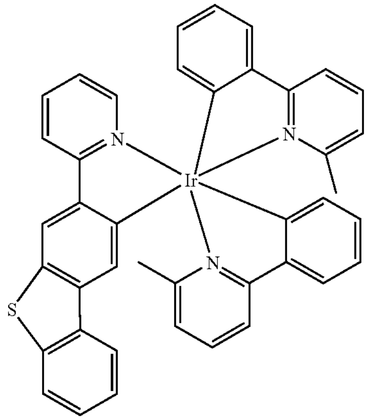
Compound 18
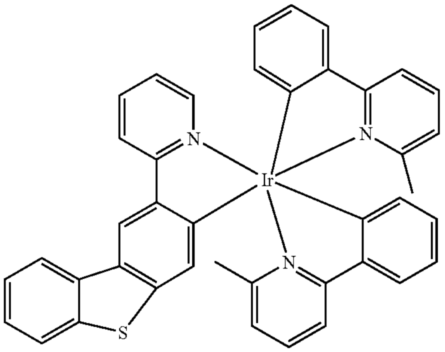
Compound 19
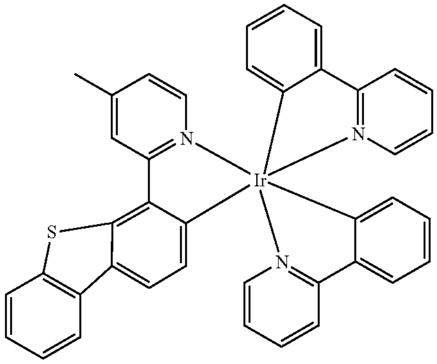
Compound 20
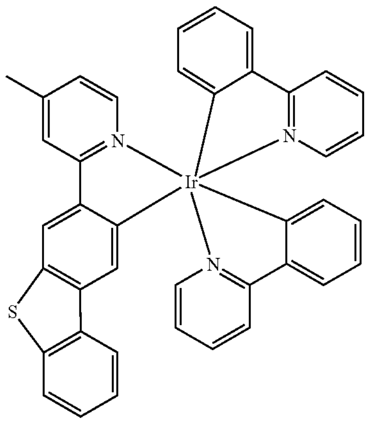
-continued
Compound 21
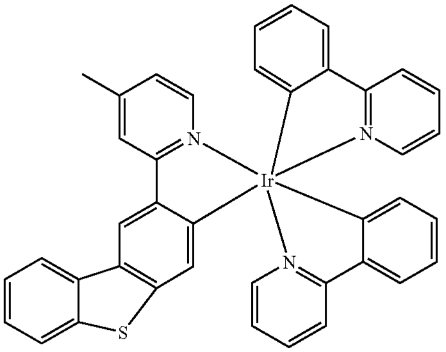
Compound 22
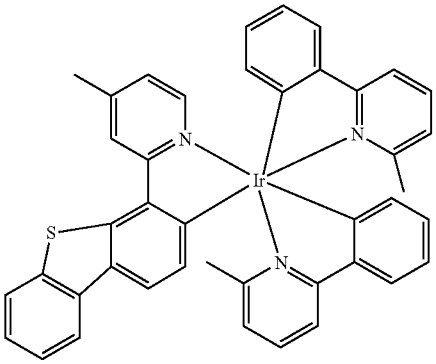
Compound 23
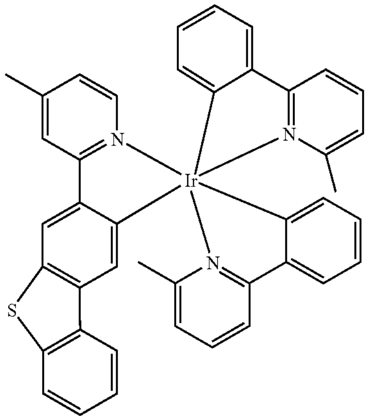
Compound 24
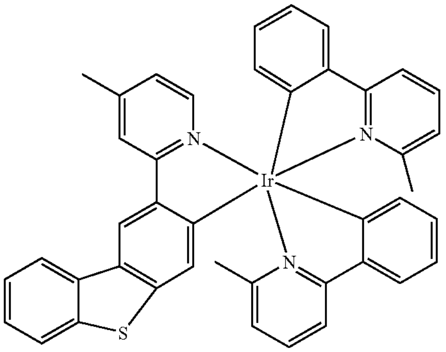

Compound 25
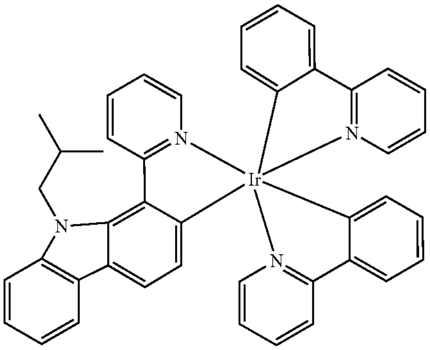
Compound 26
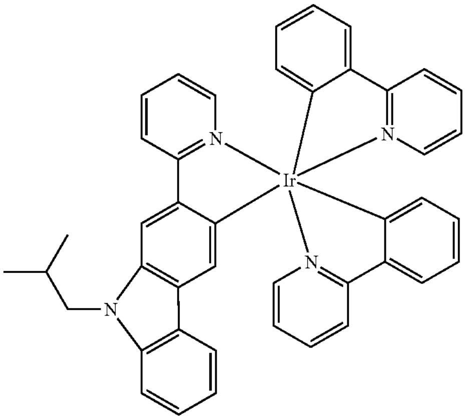
Compound 27
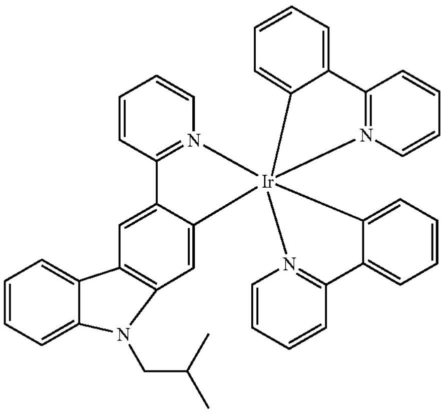
Compound 28
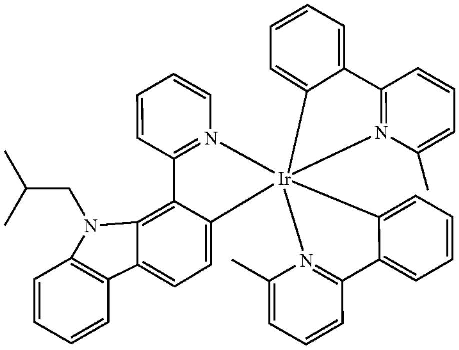
Compound 29
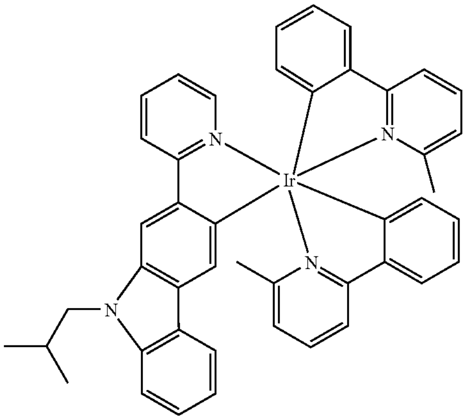
Compound 30
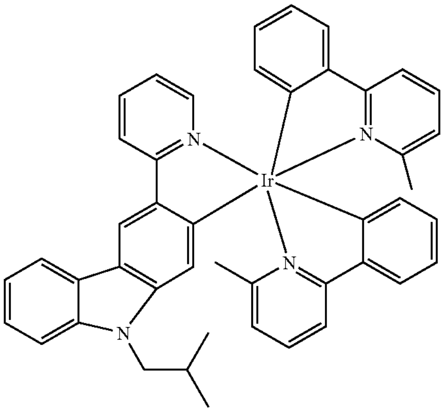
Compound 31
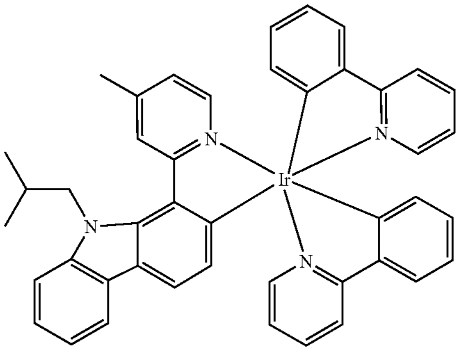

-continued
Compound 32
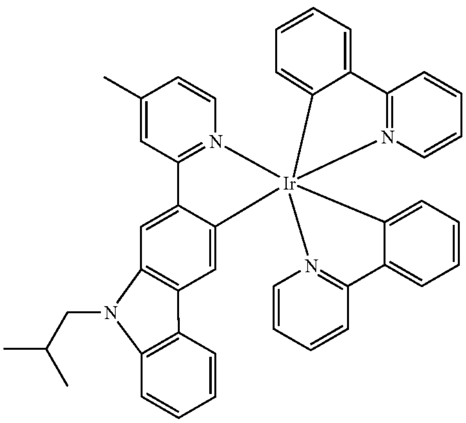
Compound 33
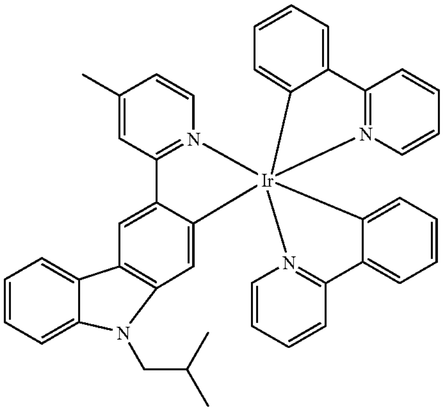
Compound 34
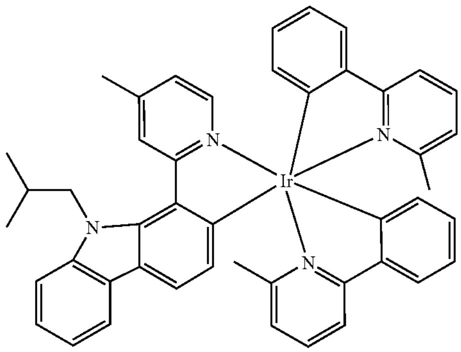
-continued
Compound 35
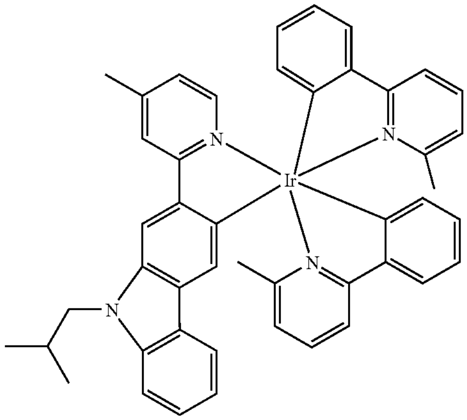
Compound 36
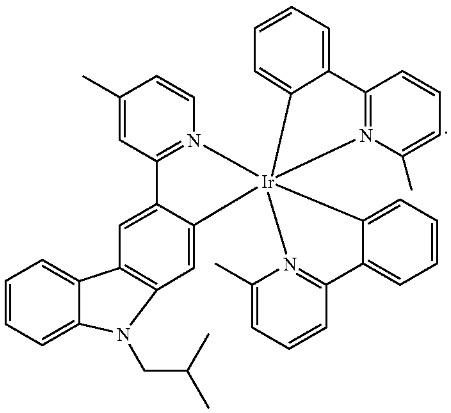
Additional specific examples of heteroleptic iridium complexes are provided, and include compounds selected from the group consisting of:
Compound 37
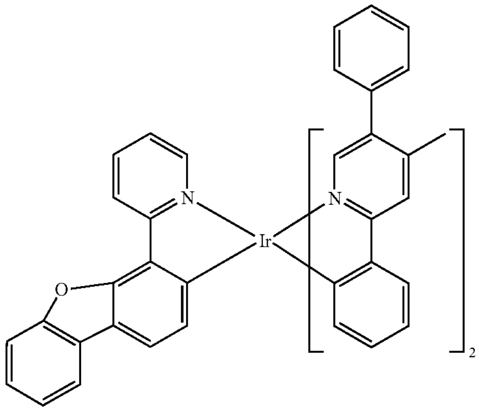

-continued
Compound 38
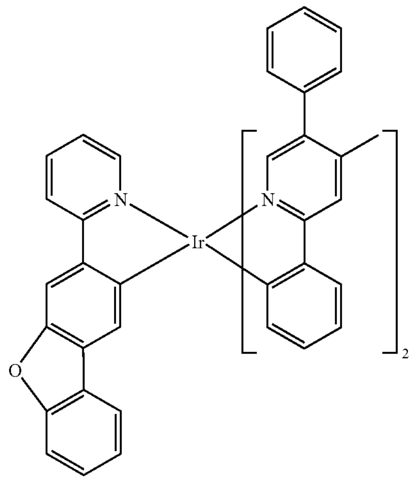
Compound 39
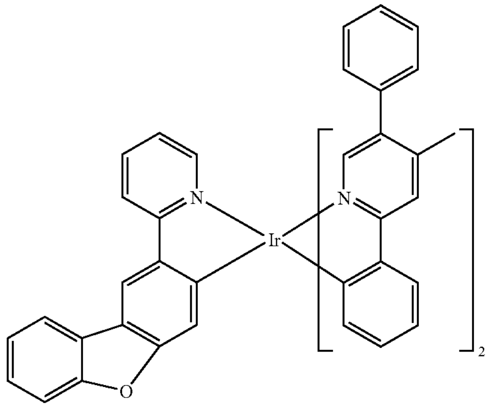
Compound 40
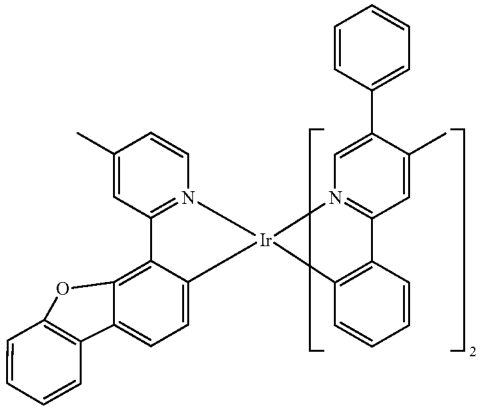
-continued
Compound 41
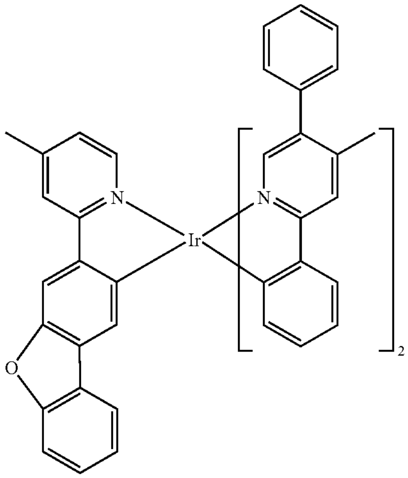
Compound 42
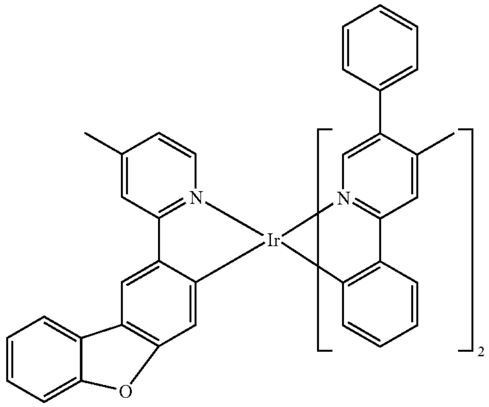
Compound 43
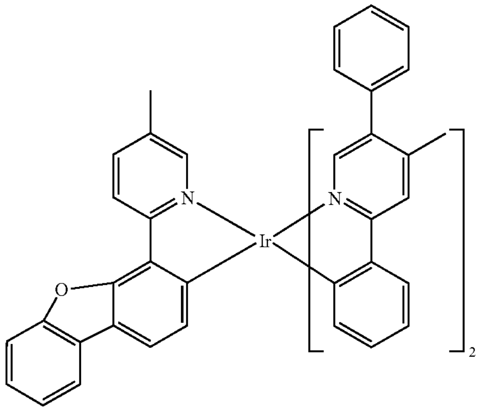

-continued
Compound 44
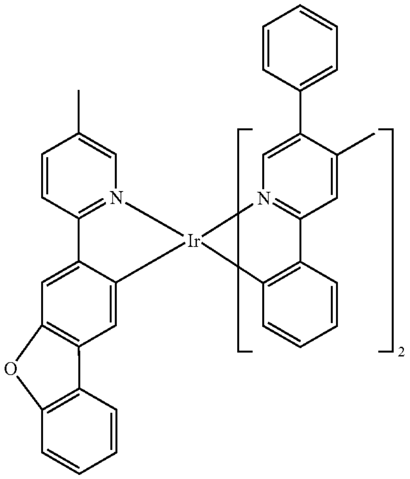
Compound 45
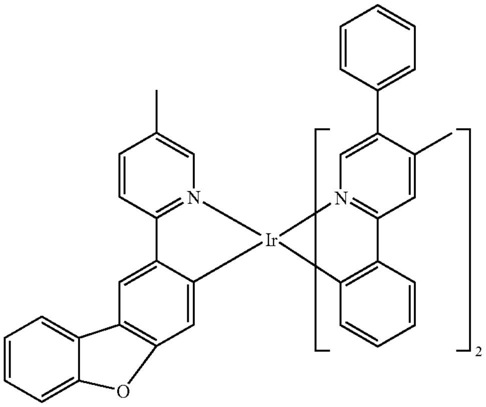
Compound 46
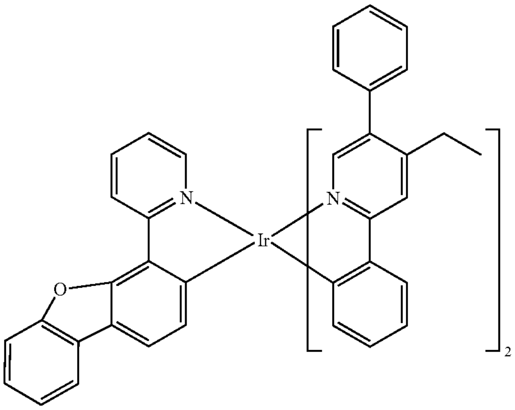
-continued
Compound 47
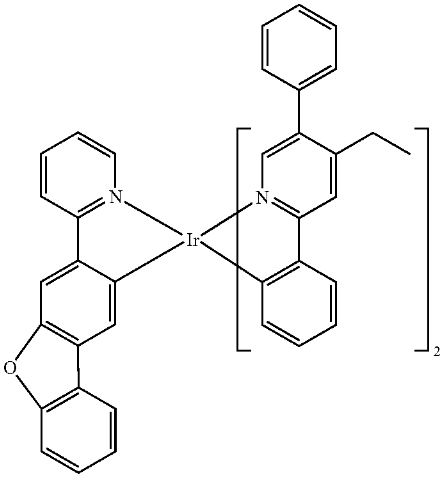
Compound 48
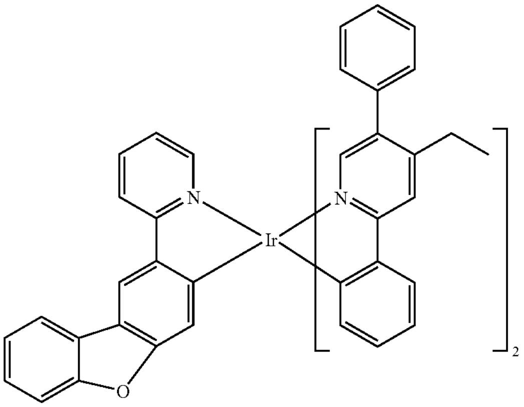
Compound 49
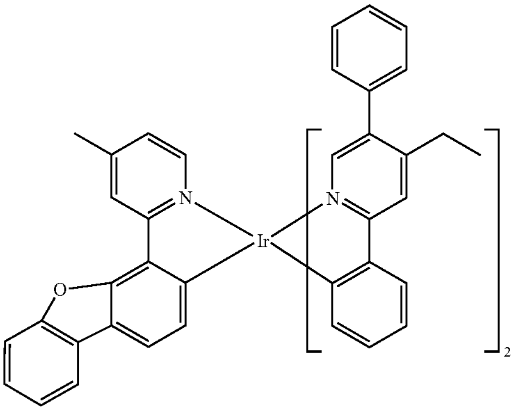

-continued
Compound 50
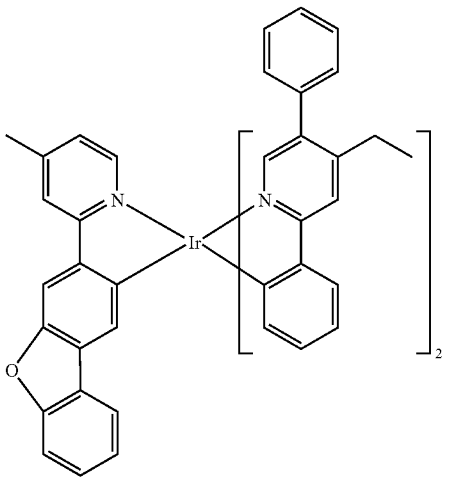
Compound 51
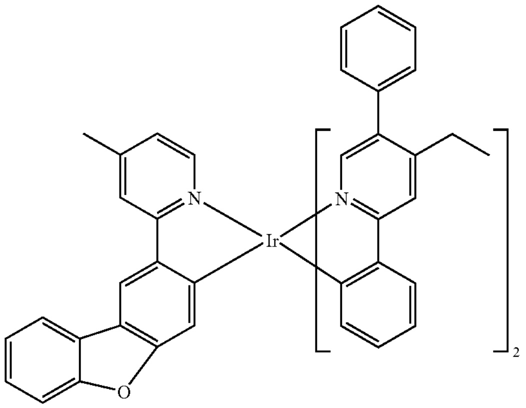
Compound 52
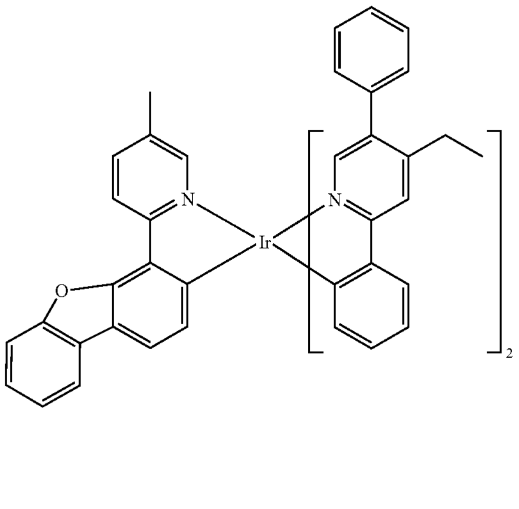
-continued
Compound 53
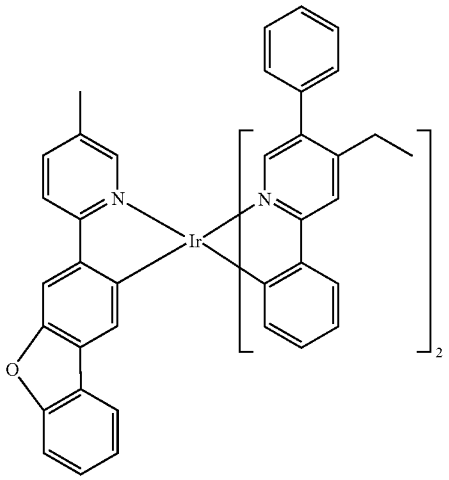
Compound 54
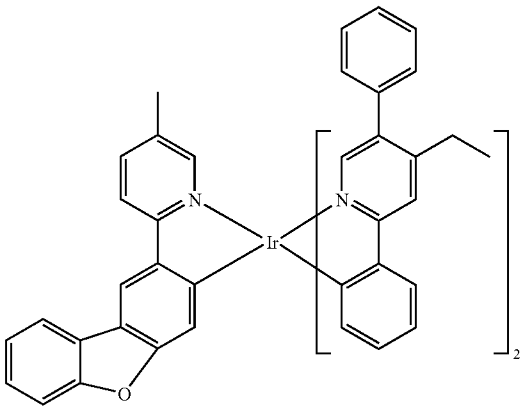
Compound 55
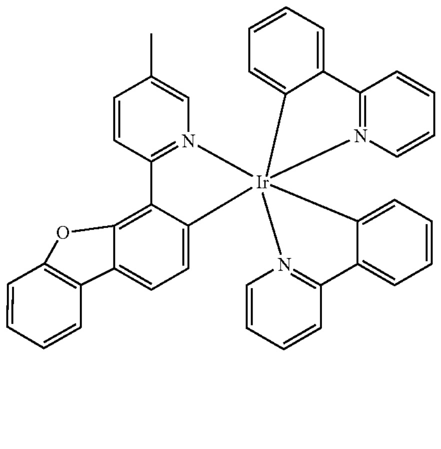

-continued
Compound 56
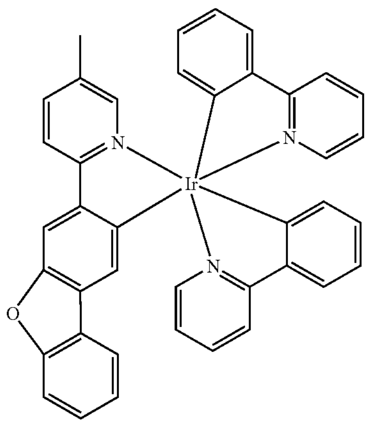
Compound 57
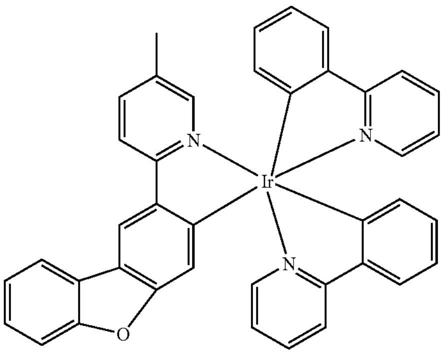
Compound 58
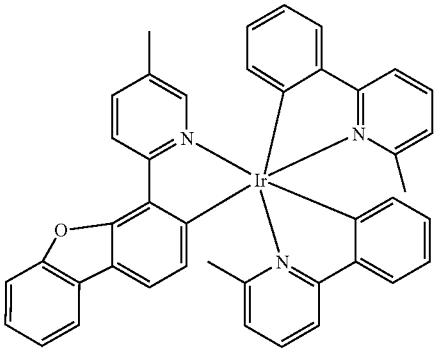
Compound 59
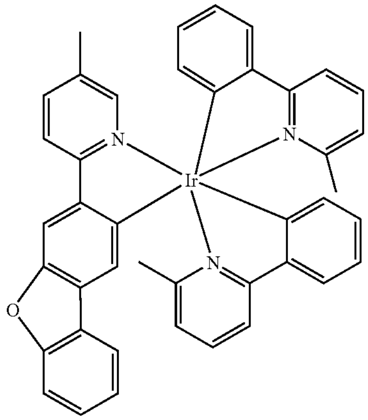
-continued
Compound 60
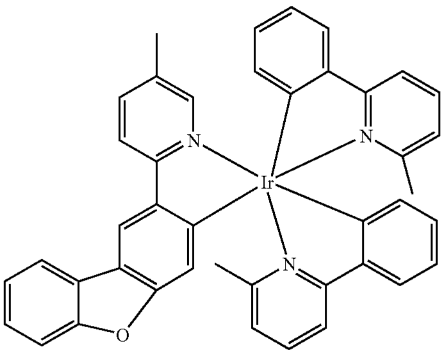
Compound 61
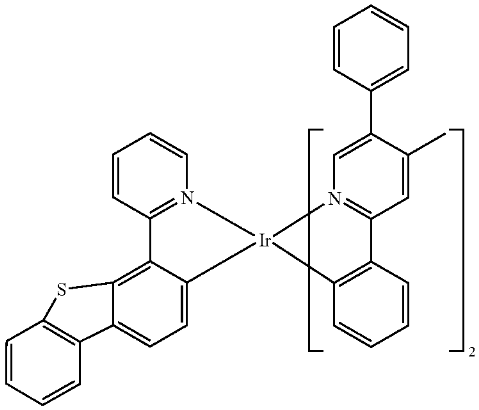
Compound 62
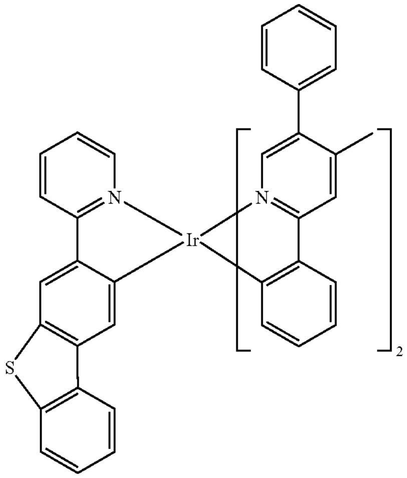

Compound 63
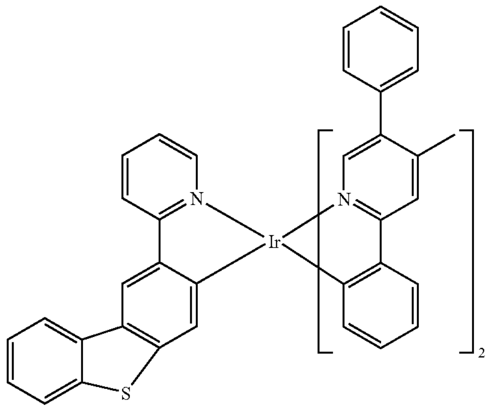
Compound 64
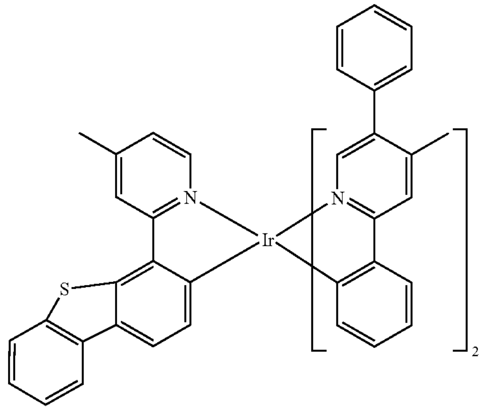
Compound 65
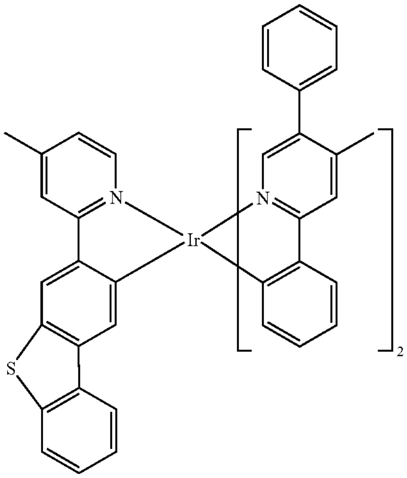
Compound 66
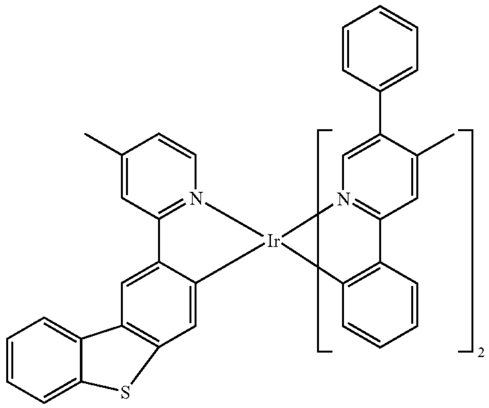
Compound 67
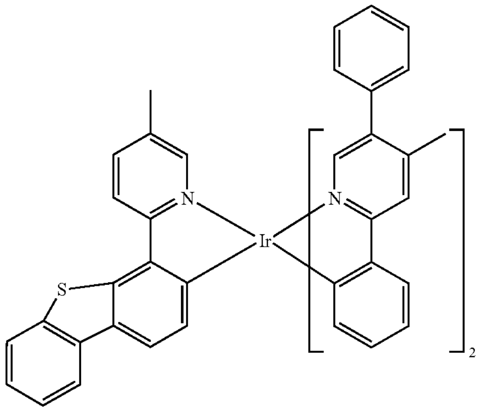
Compound 68
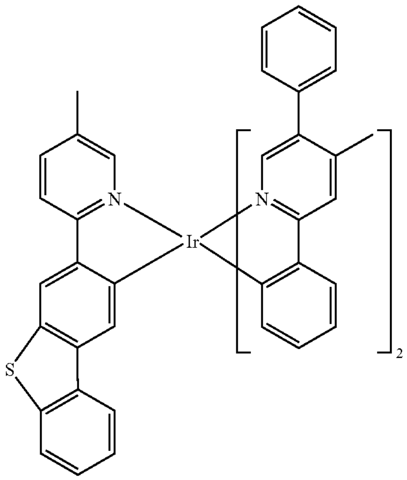

-continued
Compound 69
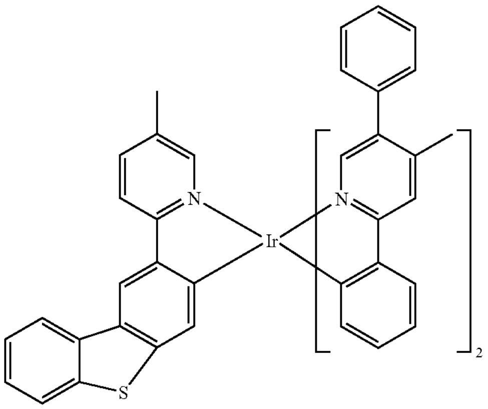
Compound 70
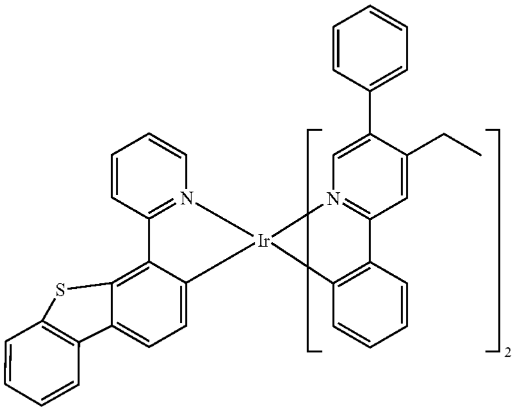
Compound 71
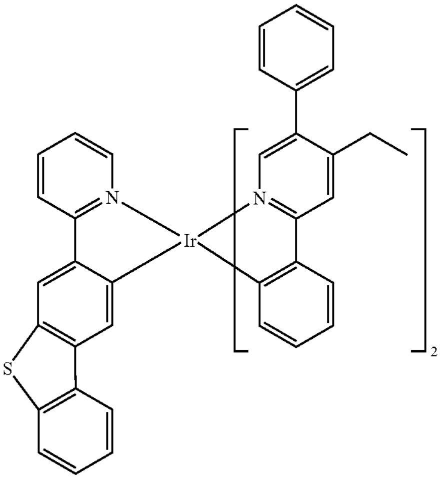
-continued
Compound 72
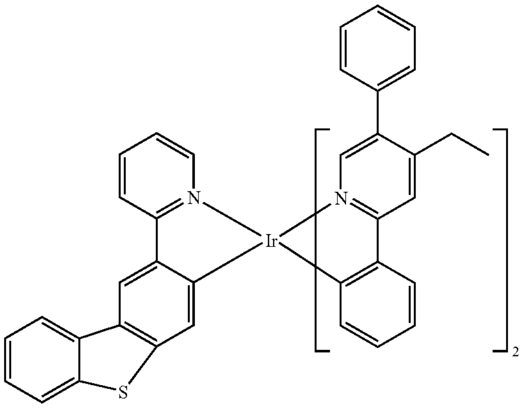
Compound 73
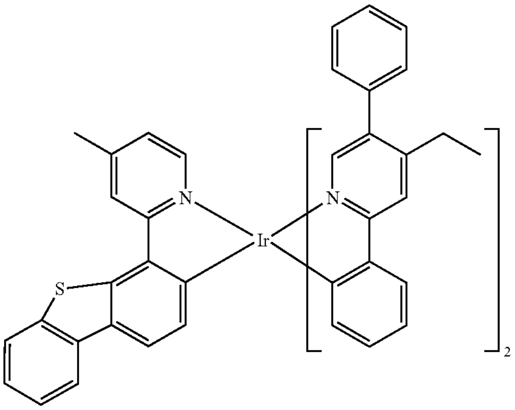
Compound 74
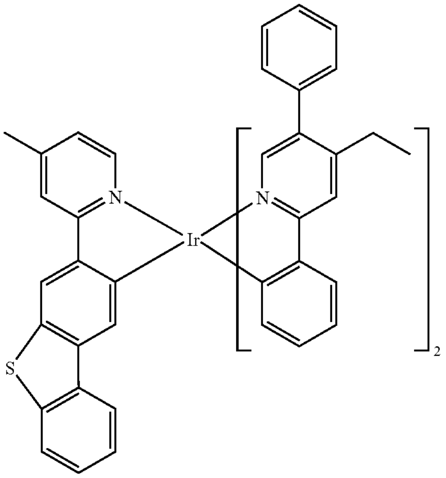

-continued
Compound 75
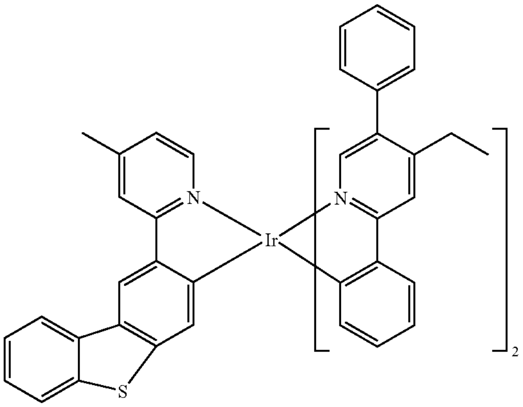
Compound 76
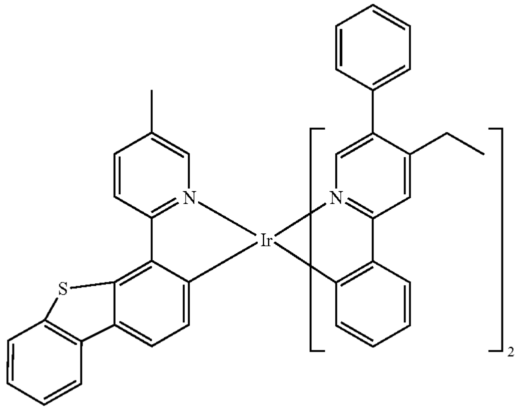
Compound 77
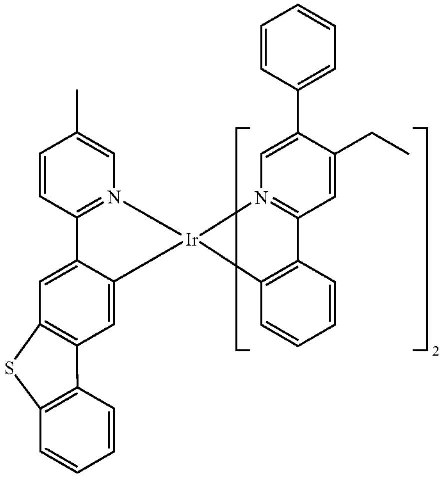
-continued
Compound 78
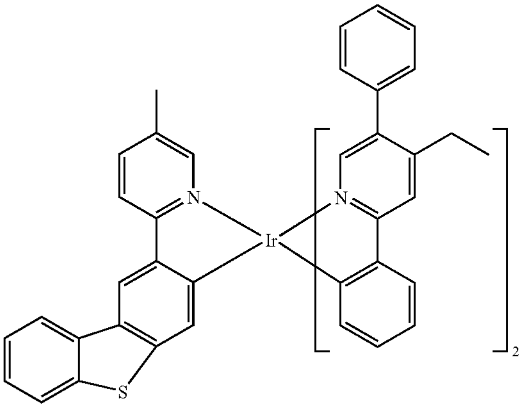
Compound 79
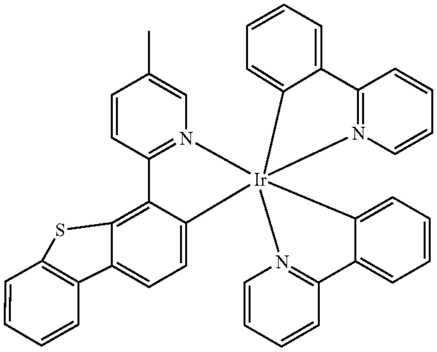
Compound 80
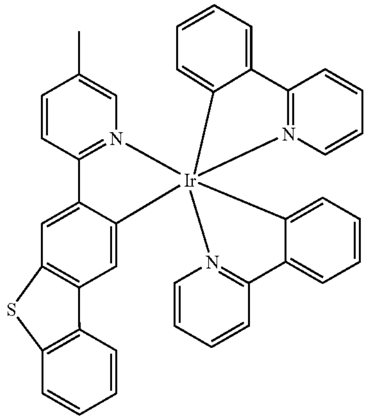
Compound 81
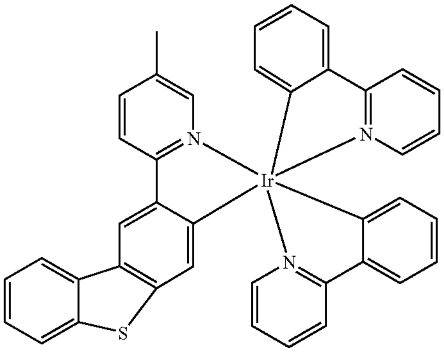

-continued
Compound 82
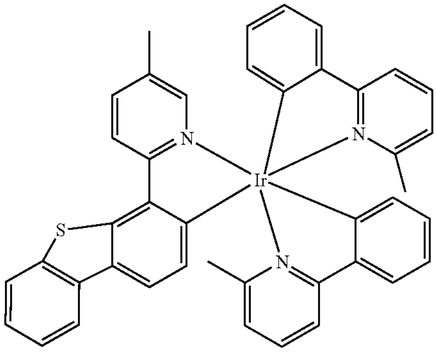
Compound 83
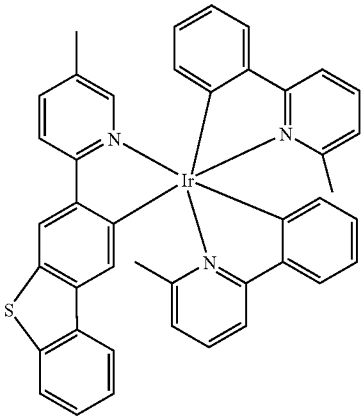
Compound 84
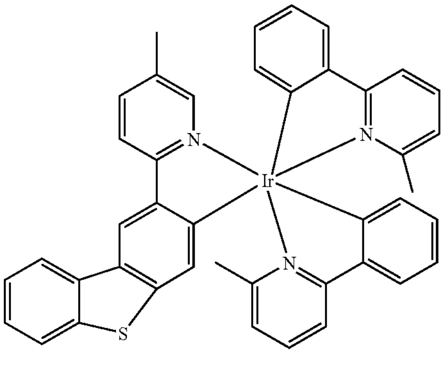
Compound 85
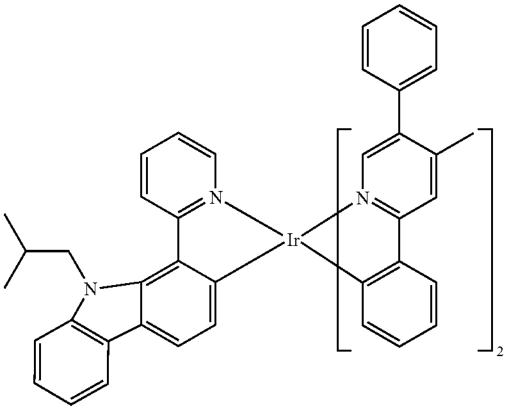
-continued
Compound 86
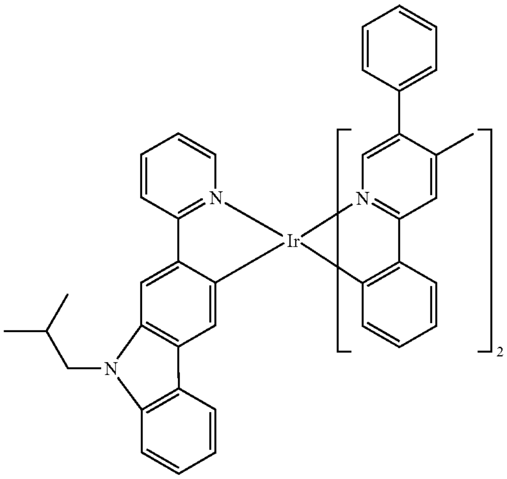
Compound 87
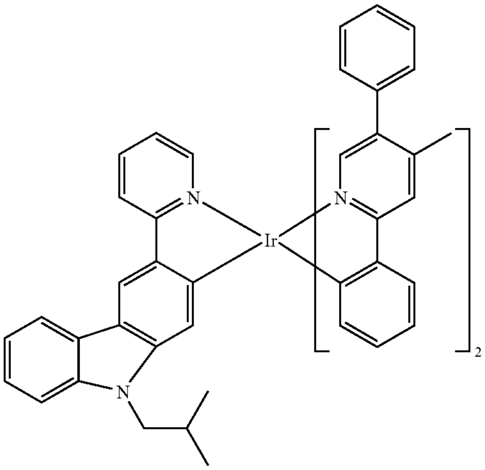
Compound 88
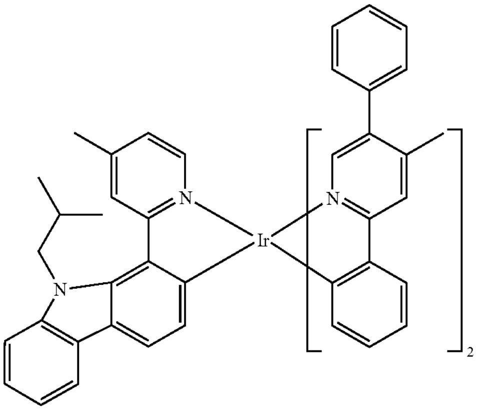

Compound 89
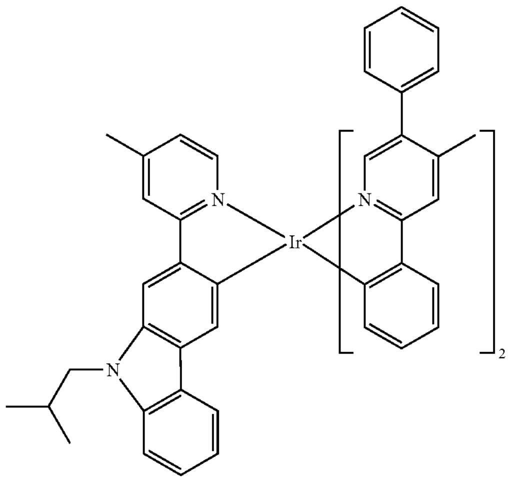
Compound 90
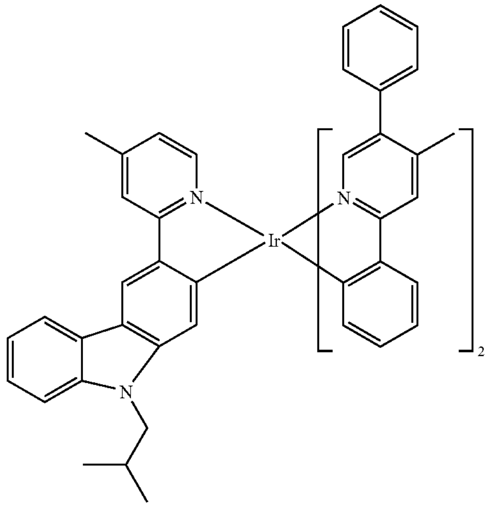
Compound 91
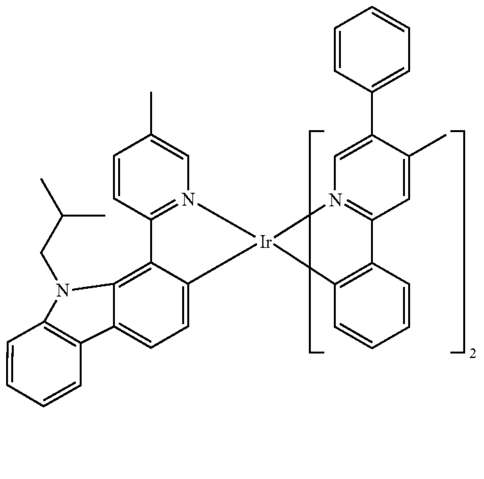
Compound 92
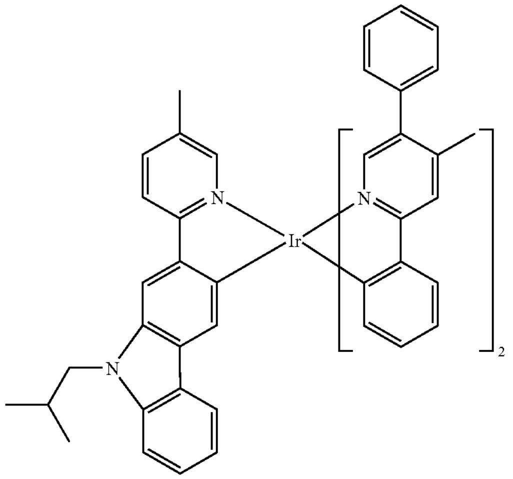
Compound 93
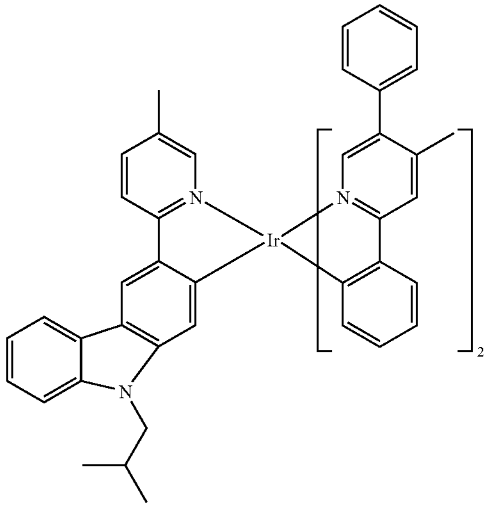
Compound 94
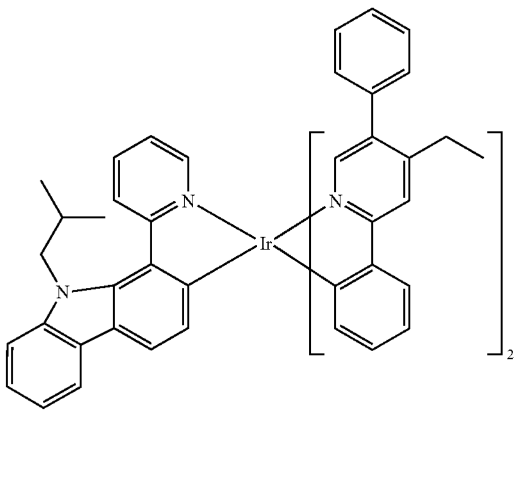

-continued
Compound 95
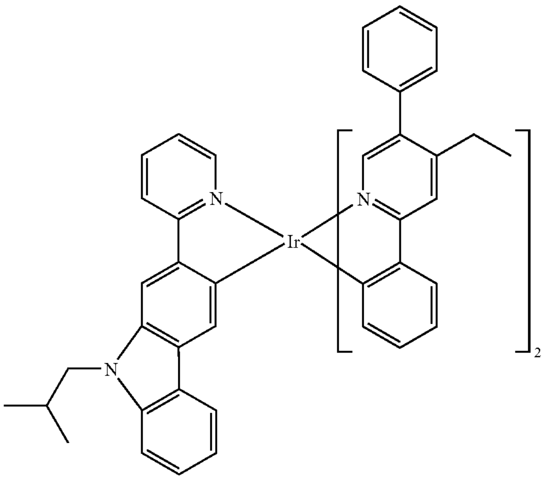
Compound 96
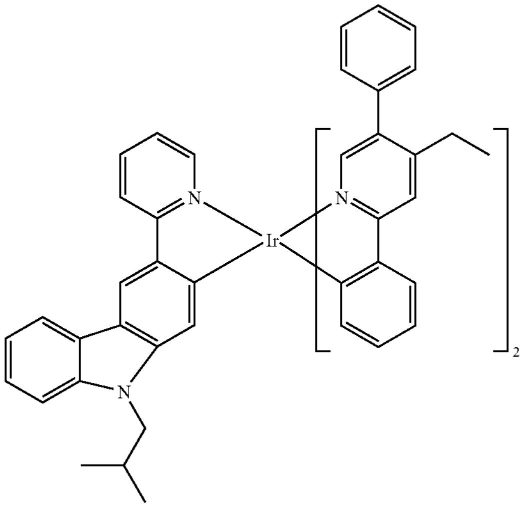
Compound 97
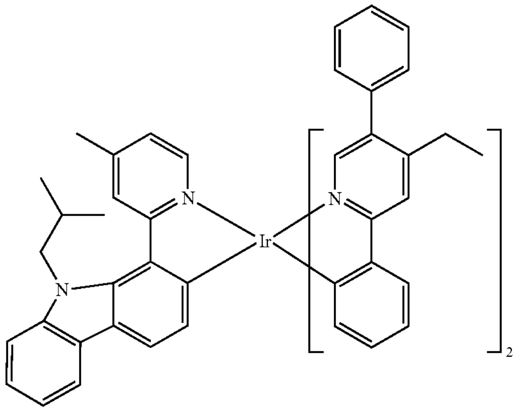
-continued
Compound 98
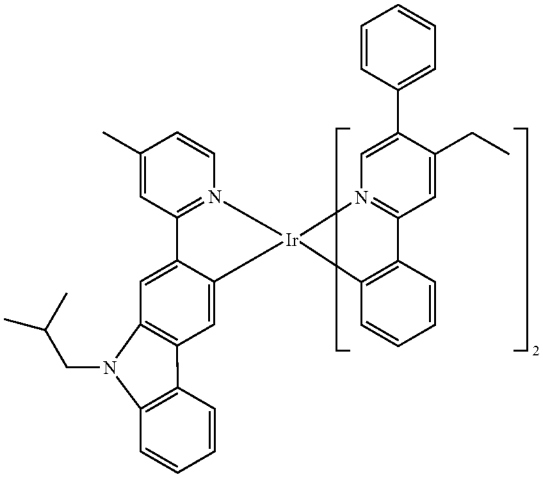
Compound 99
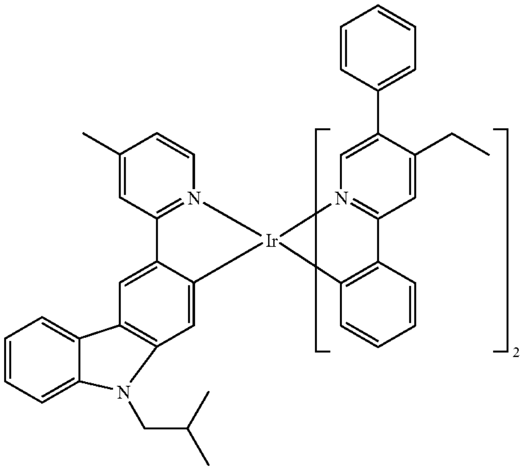
Compound 100
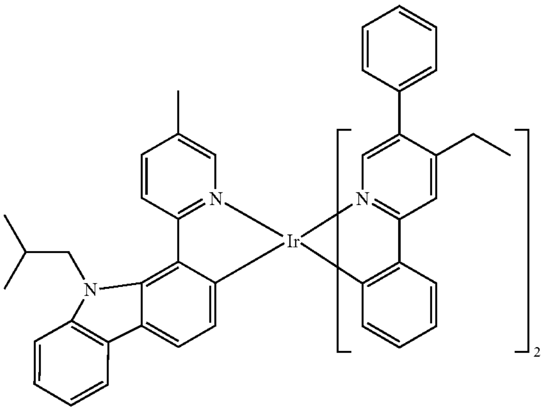

-continued
Compound 101
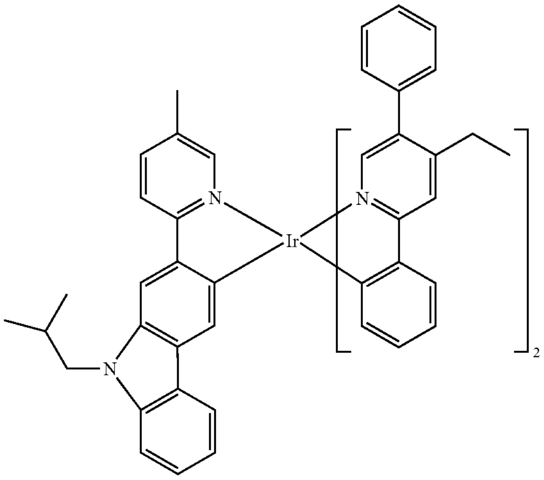
Compound 102
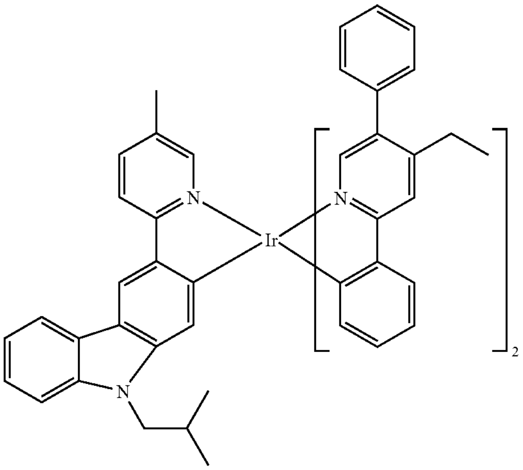
Compound 103
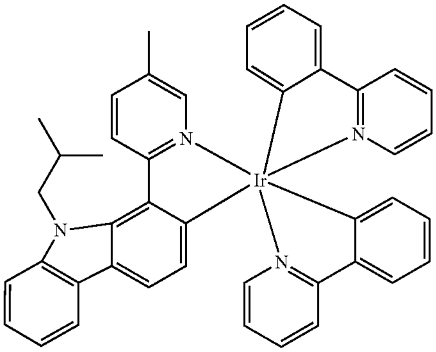
-continued
Compound 104
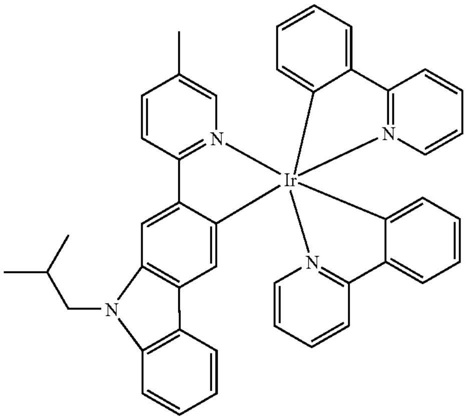
Compound 105
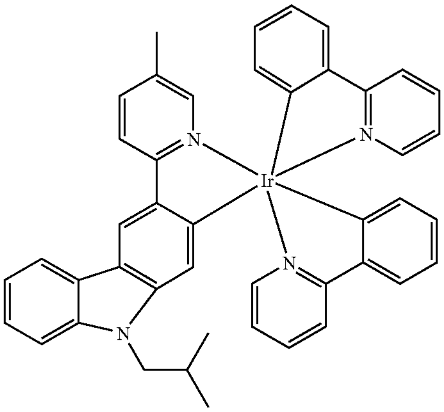
Compound 106
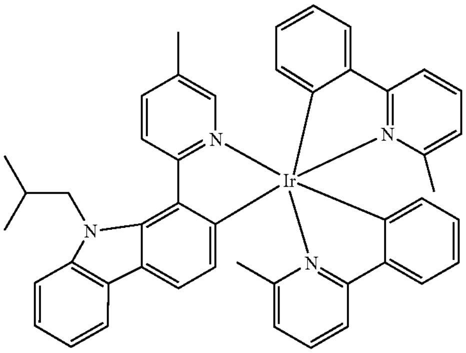

-continued

Compound 107

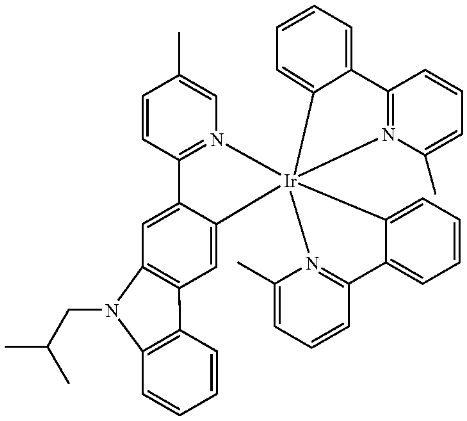

Compound 108

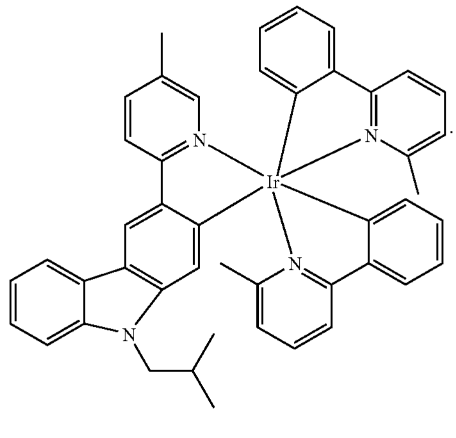

The heteroleptic iridium compound may be selected from the group consisting of Compound 1-Compound 108.

Compounds having FORMULA I in which X is selected from O, S and NR may be particularly advantageous. Without being bound by theory, it is thought that the aromaticity of the ligands comprising a dibenzofuran, dibenzothiophene or carbazole moiety (i.e., X is O, S, or NR) provides electron delocalization which may result in improved compound stability and improved devices. Moreover, it is believed that compounds wherein X is O may be more preferable than compounds wherein X is S or NR. In many cases, dibenzofuran containing compounds and devices comprising such compounds demonstrate especially desirable properties.

In one aspect, compounds are provided wherein X is O. Exemplary compounds where X is O include, but are not limited to, Compounds 1-12. Compounds wherein X is O may be especially preferred at least because these compounds may generate devices having desirable properties. For example, these compounds may provide devices having improved efficiency and a long lifetime. Additionally, the reduced sublimation temperature of these compounds can also result in improved manufacturing of such desirable devices.

Additional exemplary compounds where X is O are provided and include, without limitation, Compounds 37-60. Compounds 1-12 and 37-60 may provide devices having improved efficiency, lifetime, and manufacturing.

In another aspect, compounds are provided wherein X is S. Exemplary compounds where X is S include, but are not limited to, Compounds 13-24. These compounds, containing a pyridyl dibenzofuran ligand, may also be used in devices demonstrating good properties. For example, compounds wherein X is S may provide devices having improved stability and manufacturing.

Additional exemplary compounds where X is S are provided and include, without limitation, Compounds 61-84. Compounds 13-24 and 61-84 may provide devices having improved stability and manufacturing.

In yet another aspect, compounds are provided wherein X is NR. Exemplary compounds wherein X is NR include, but are not limited to, Compounds 25-36. These compounds containing a pyridyl carbazole ligand may also be used to provide devices having good properties, such as improved efficiency.

Additional exemplary compounds where X is NR are provided and include, without limitation, Compounds 85-108. Compounds 26-36 and 85-108 may provide devices having improved efficiency.

Additionally, an organic light emitting device is also provided. The device comprises an anode, a cathode, and an organic layer disposed between the anode and the cathode, wherein the organic layer comprises a compound having FORMULA I. X is selected from the group consisting of NR, O, S, BR, and Se. R is selected from hydrogen and alkyl. Preferably, R has 4 or fewer carbon atoms. $R_1$, $R_2$, $R_3$ and $R_4$ may represent mono, di, tri, or tetra substitutions. Each of $R_1$, $R_2$, $R_3$ and $R_4$ are independently selected from the group consisting of hydrogen, alkyl having four or fewer carbon atoms, and aryl. Preferably, $R_2$ and $R_3$ are independently selected from the group consisting of hydrogen and alkyl having four or fewer carbon atoms. Selections for the heteroatoms and substituents described as preferred for the compound of FORMULA I are also preferred for use in a device that includes a compound having FORMULA I. These selections include those described for X, R, $R_1$, $R_2$ and $R_3$ and $R_4$.

In another aspect, each of $R_1$, $R_2$, $R_3$ and $R_4$ are independently selected from the group consisting of hydrogen, alkyl having four or fewer carbon atoms, and aryl with 6 or fewer atoms in the ring. Preferably, $R_2$ and $R_3$ are independently selected from the group consisting of hydrogen, alkyl having four or fewer carbon atoms and aryl with 6 or fewer atoms in the ring.

In particular, devices are provided wherein the compound is selected from the group consisting of Compounds 1-36.

In addition, devices are provided which contain a compound selected from the group consisting of Compounds 37-108. Moreover, the devices provided may contain a compound selected from the group consisting of Compounds 1-108.

In one aspect, the organic layer is an emissive layer and the compound having FORMULA I is an emitting dopant. The organic layer may further comprise a host. Preferably, the host comprises a triphenylene moiety and a dibenzothiophene moiety. More preferably, the host has the formula:

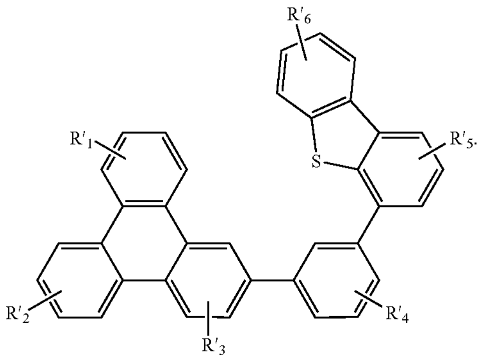

R'1, R'2, R'3, R'4, R'5, and R'6 may represent mono, di, tri, or tetra substitutions. Each of R'1, R'2, R'3, R'4, R'5, and R'6 are independently selected from the group consisting of hydrogen, alkyl, and aryl.

As discussed above, the heteroleptic compounds provided herein may be advantageously used in organic light emitting devices to provide devices having desirable properties such as improved lifetime, stability and manufacturing.

A consumer product comprising a device is also provided. The device further comprises an anode, a cathode, and an organic layer. The organic layer further comprises a heteroleptic iridium complex having FORMULA I.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | 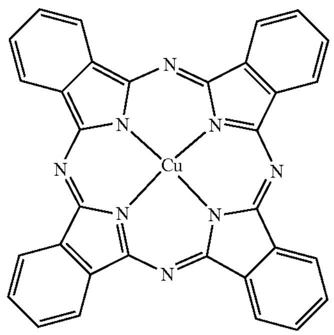 | Appl. Phys. Lett. 69, 2160 (1996) |
| Starburst triarylamines | 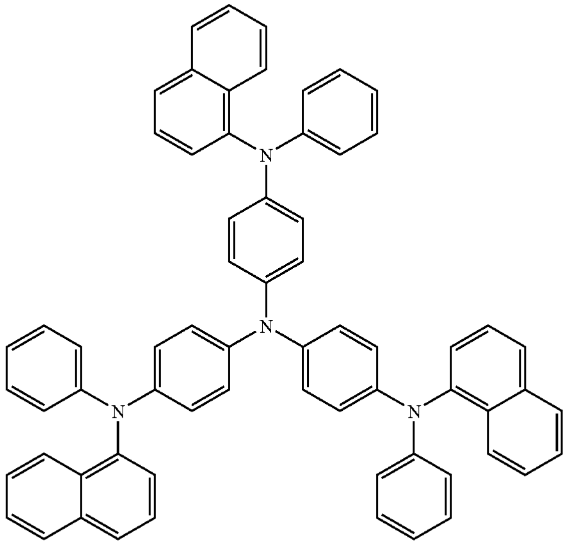 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |

TABLE 2-continued
| MATERIAL | EXAMPLES OF MATERIAL | PUBLICATIONS |
|---|---|---|
| $CF_x$ Fluorohydrocarbon polymer | $-\!\![\!-CH_xF_y-\!]_n-$ | Appl. Phys. Lett. 78, 673 (2001) |
| Conducting polymers (e.g., PEDOT:PSS, polyaniline, polypthiophene) | 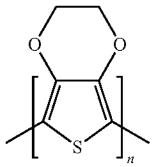 + 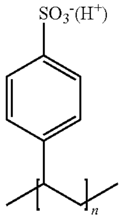 | Synth. Met. 87, 171 (1997) WO2007002683 |
| Phosphonic acid and sliane SAMs | 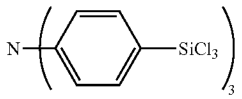 | US20030162053 |
| Triarylamine or polythiophene polymers with conductivity dopants | 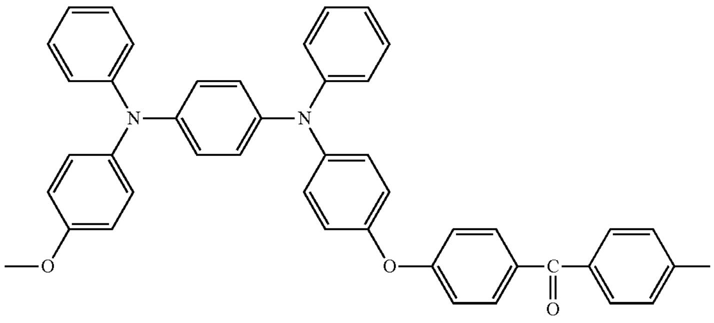 and 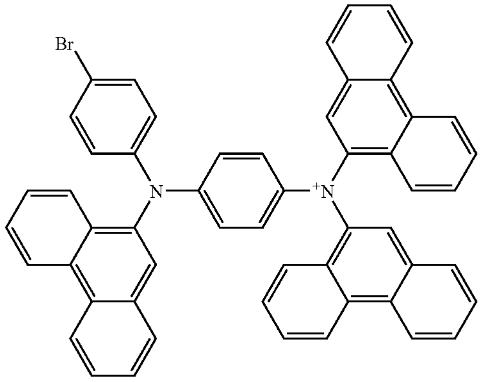 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 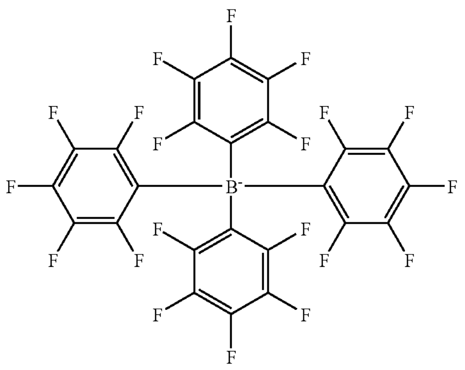 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EA01725079A1 |

TABLE 2-continued
| MATERIAL | EXAMPLES OF MATERIAL | PUBLICATIONS |
|---|---|---|
| Arylamines complexed with metal oxides such as molybdenum and tungsten oxides | 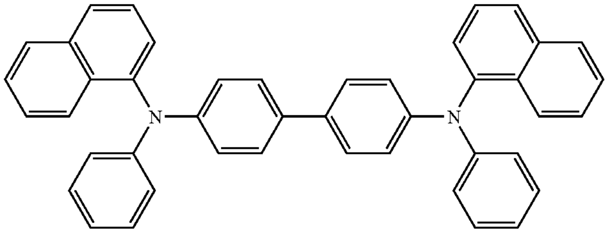 + $MoO_x$ | SID Symposium Digest, 37, 923 (2006) WO2009018009 |
| p-type semiconducting organic complexes | 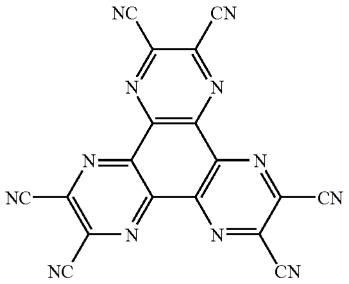 | US20020158242 |
| Metal organometallic complexes | 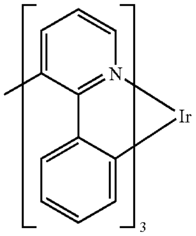 | US20060240279 |
| Cross-linkable compounds | 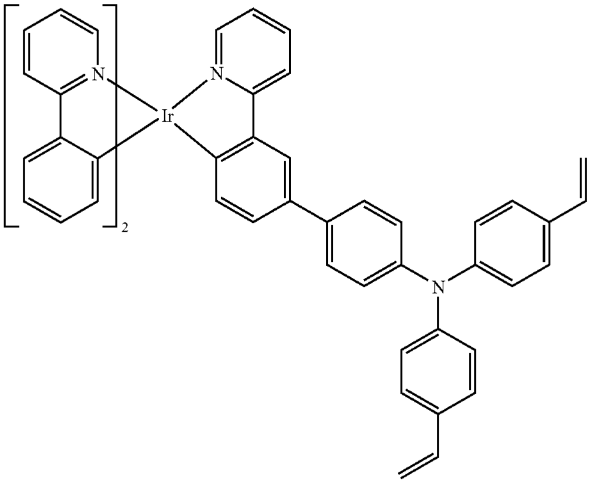 | US20080220265 |
| Hole transporting materials | | |
| Triarylamines (e.g., TPD, α-NPD) | 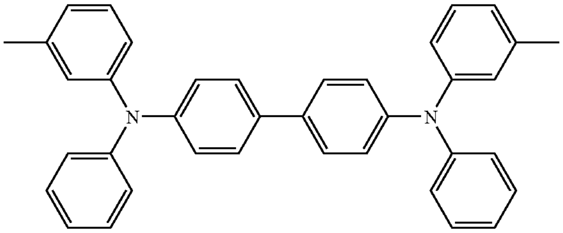 | Appl. Phys. Lett. 51, 913 (1987) |

TABLE 2-continued
| MATERIAL | EXAMPLES OF MATERIAL | PUBLICATIONS |
|---|---|---|
| | 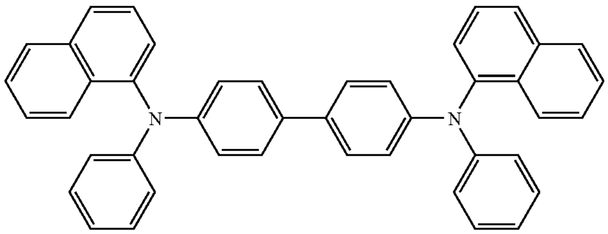 [SMILES: c1ccc(N(c2ccc(-c3ccc(N(c4ccccc4)c4cccc5ccccc45)cc3)cc2)c2cccc3ccccc23)cc1] | US5061569 |
| | 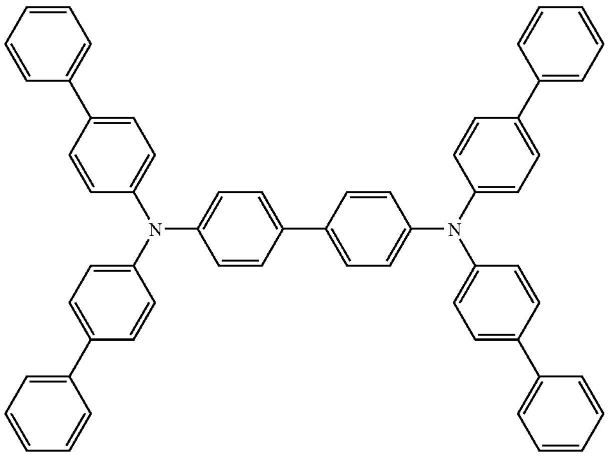 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 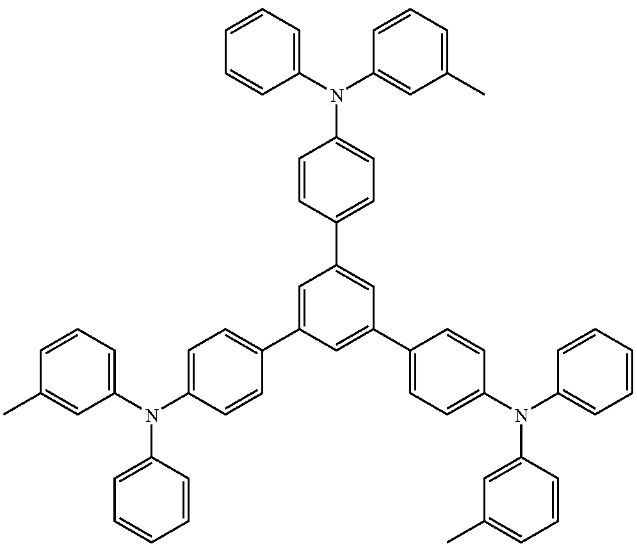 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 2-continued
| MATERIAL | EXAMPLES OF MATERIAL | PUBLICATIONS |
|---|---|---|
| | 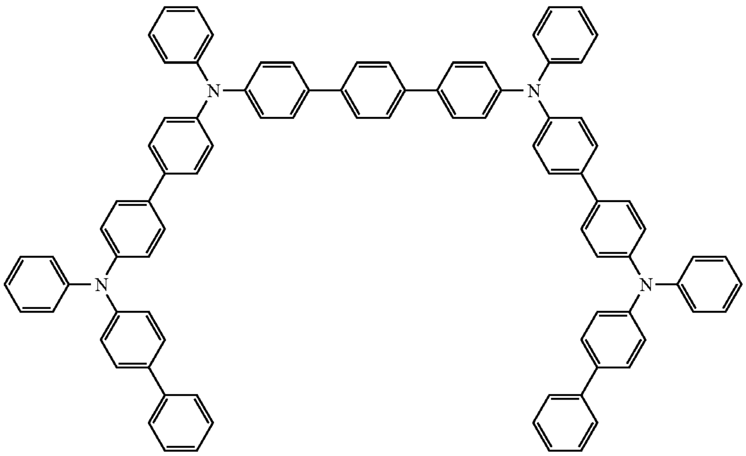 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 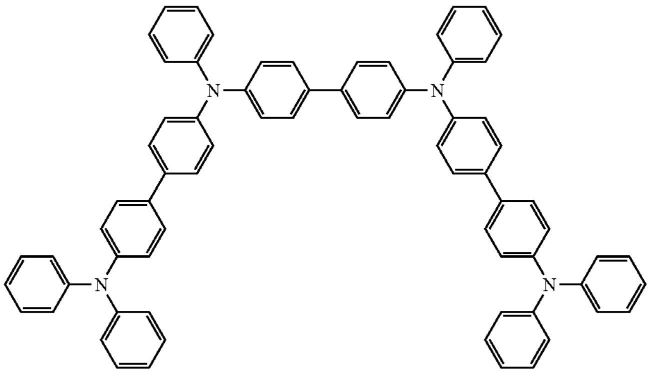 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett 90, 183503 (2007) |
| Triaylamine on spirofluorene core | 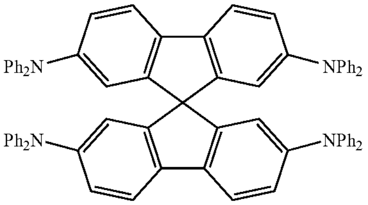 | Synth. Met. 91, 209 (1997) |
| Arylamine carbazole compounds | 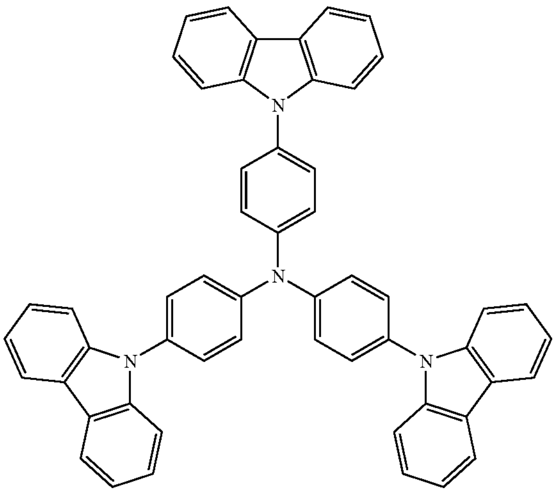 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 2-continued
| MATERIAL | EXAMPLES OF MATERIAL | PUBLICATIONS |
|---|---|---|
| Triarylamine with (di)benzothiophene/ (di)benzofuran | 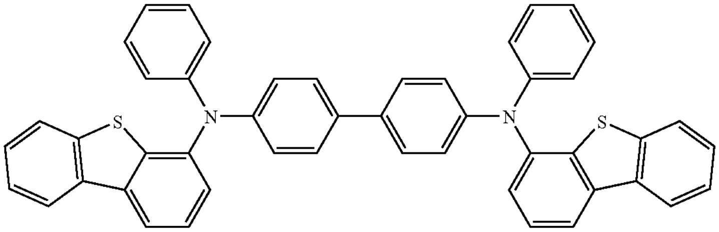 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 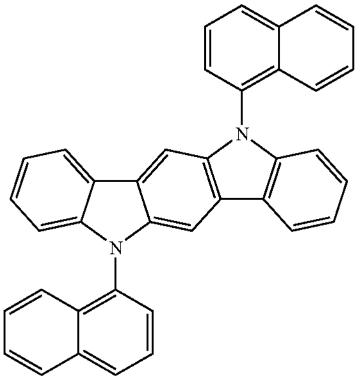 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 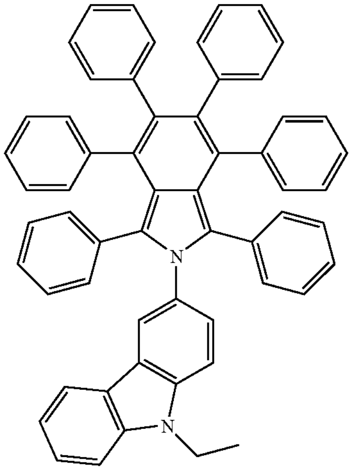 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 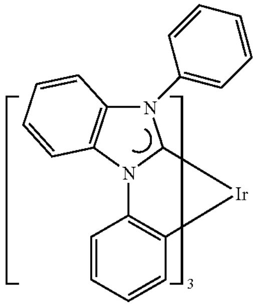 | US20080018221 |

TABLE 2-continued
| MATERIAL | EXAMPLES OF MATERIAL | PUBLICATIONS |
|---|---|---|
| Phosphorescent OLED host materials<br>Red hosts | | |
| Arylcarbazoles | 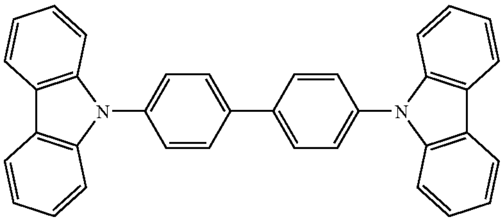 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., $Alq_3$, BAlq) | 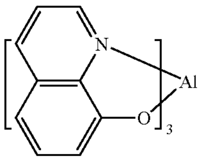 | Nature 395, 151 (1998) |
| | 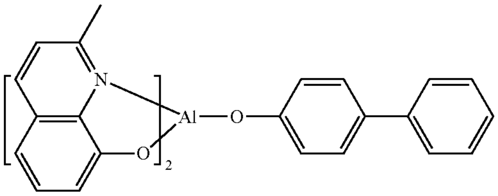 | US20060202194 |
| | 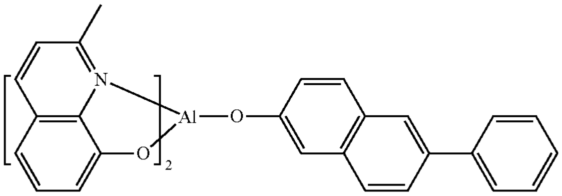 | WO2005014551 |
| | 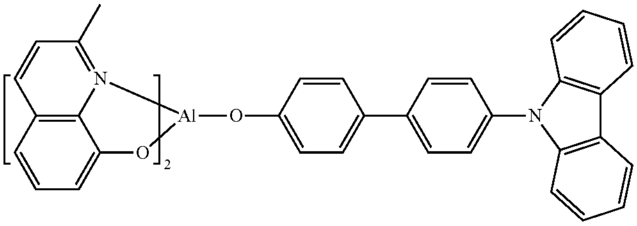 | WO2006072002 |
| Metal phenoxybenzothiazole compounds | 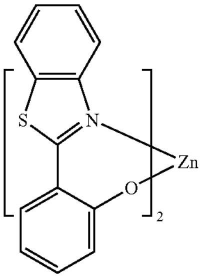 | Appl. Phys. Lett. 90, 123509 (2007) |
| Conjugated oligomers and polymers (e.g., polyfluorene) | 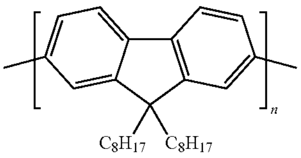 | Org. Electron. 1, 15 (2000) |

TABLE 2-continued
| MATERIAL | EXAMPLES OF MATERIAL | PUBLICATIONS |
|---|---|---|
| Aromatic fused rings | 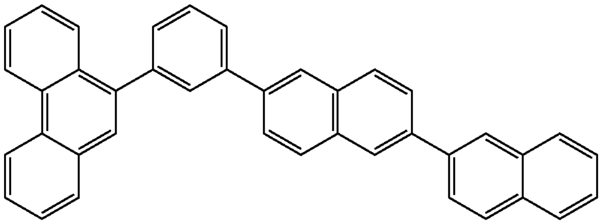 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 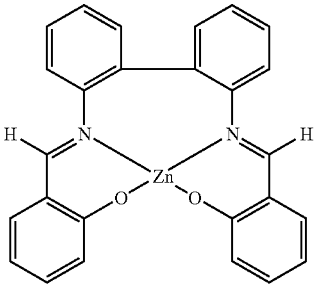 | WO2009062578 |
| Green hosts | | |
| Arylcarbazoles | 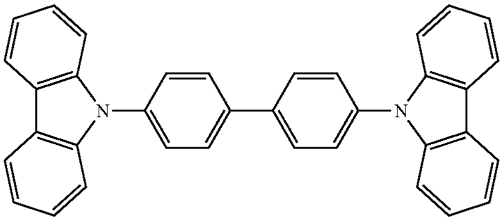 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 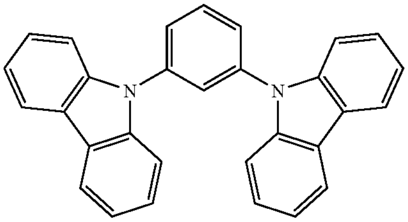 [SMILES: c1cc(-n2c3ccccc3c3ccccc32)cc(-n2c3ccccc3c3ccccc32)c1] | US20030175553 |
| | 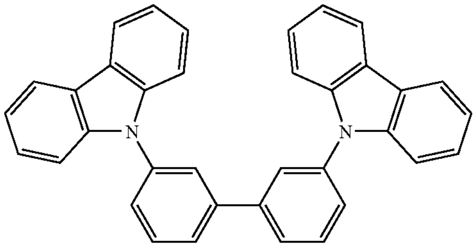 [SMILES: c1cc(-c2cccc(-n3c4ccccc4c4ccccc43)c2)cc(-n2c3ccccc3c3ccccc32)c1] | WO2001039234 |
| Aryltriphenylene compounds | 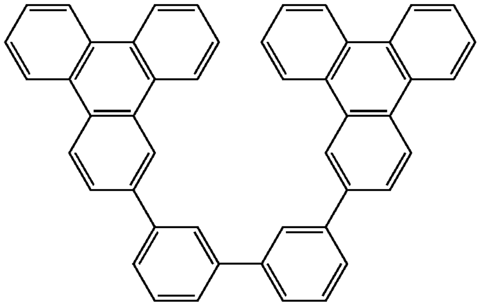 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 2-continued
| MATERIAL | EXAMPLES OF MATERIAL | PUBLICATIONS |
|---|---|---|
| | 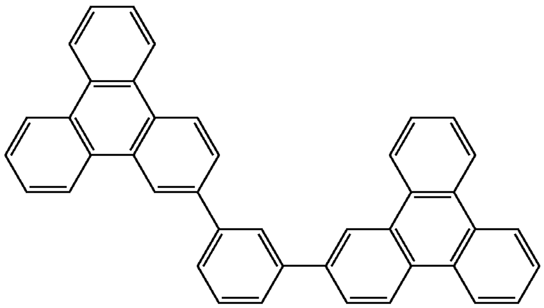 [SMILES: c1cc(-c2ccc3c4ccccc4c4ccccc4c3c2)cc(-c2ccc3c4ccccc4c4ccccc4c3c2)c1] | US20060280965 |
| | 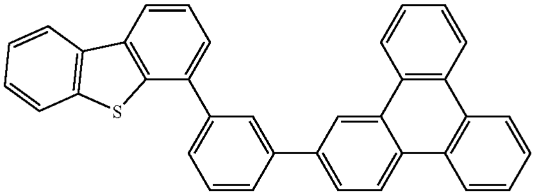 [SMILES: c1cc(-c2ccc3c4ccccc4c4ccccc4c3c2)cc(-c2cccc3c2sc2ccccc23)c1] | WO2009021126 |
| Donor acceptor type molecules | 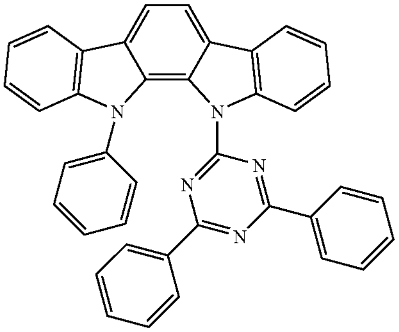 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 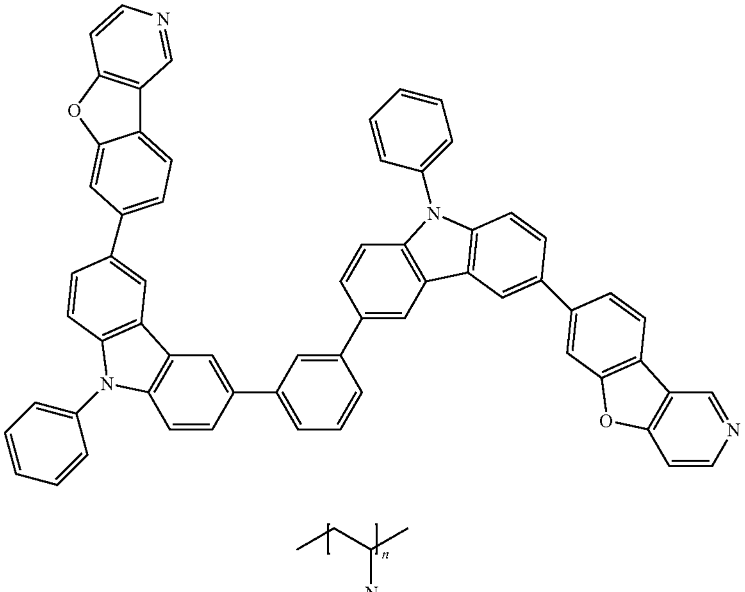 | JP2008074939 |
| Polymers (e.g., PVK) | 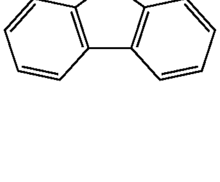 | Appl. Phys. Lett. 77, 2280 (2000) |

TABLE 2-continued
| MATERIAL | EXAMPLES OF MATERIAL | PUBLICATIONS |
| --- | --- | --- |
| Spirofluorene compounds | 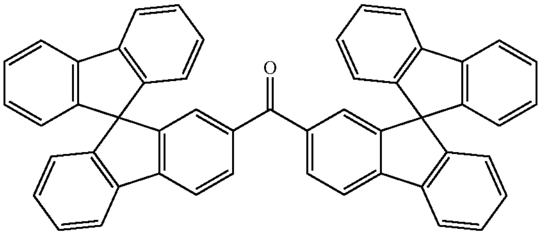 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 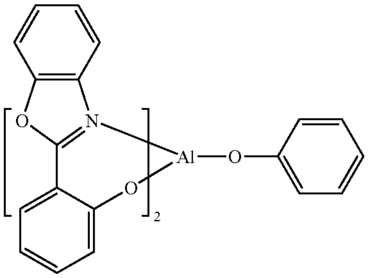 | WO2005089025 |
| | 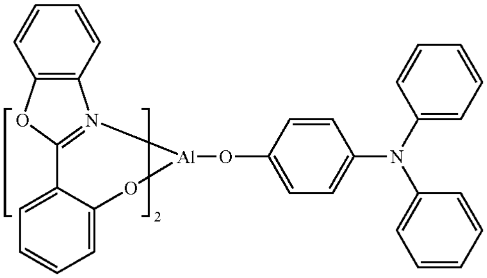 | WO2006132173 |
| | 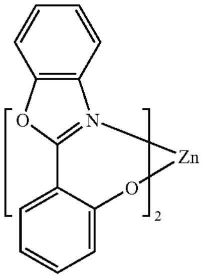 | JP200511610 |
| Spirofluorene-carbazole compounds | 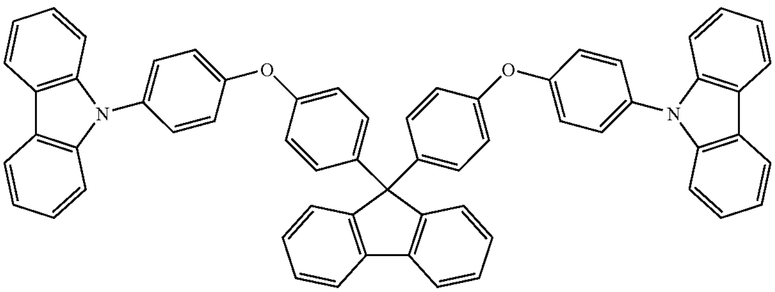 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 2-continued
| MATERIAL | EXAMPLES OF MATERIAL | PUBLICATIONS |
|---|---|---|
| | 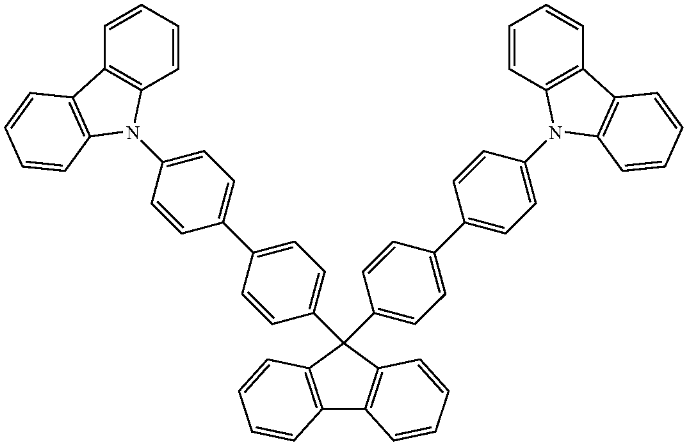 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 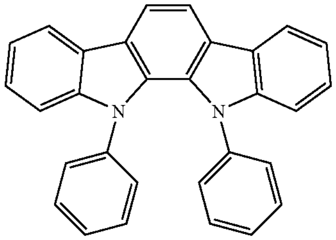 [SMILES: c1ccc(-n2c3ccccc3c3ccc4c5ccccc5n(-c5ccccc5)c4c32)cc1] | WO2007063796 |
| | 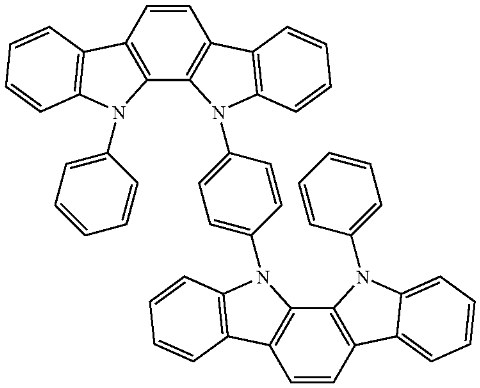 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 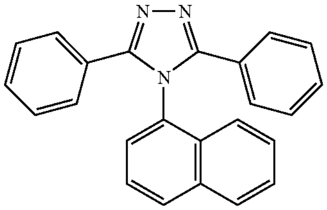 [SMILES: c1ccc(-c2nnc(-c3ccccc3)n2-c2cccc3ccccc23)cc1] | J. Appl. Phys. 90, 5048 (2001) |
| | 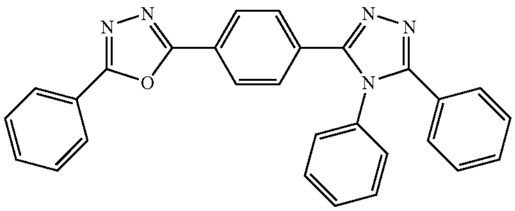 [SMILES: c1ccc(-c2nnc(-c3ccc(-c4nnc(-c5ccccc5)n4-c4ccccc4)cc3)o2)cc1] | WO2004107822 |

TABLE 2-continued
| MATERIAL | EXAMPLES OF MATERIAL | PUBLICATIONS |
|---|---|---|
| Tetraphenylene complexes | 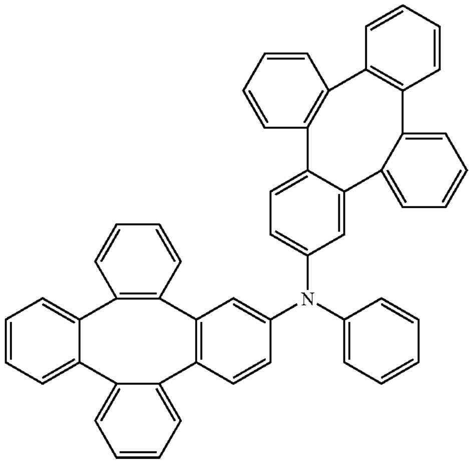 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 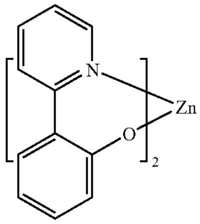 | WO2005030900 |
| Metal coordination complexes (e.g., Zn, Al with N^N ligands) | 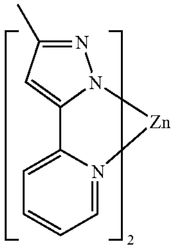 | US20040137268, US20040137267 |
| Blue hosts | | |
| Arylcarbazoles | 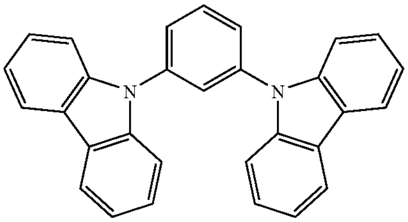 [SMILES: c1cc(-n2c3ccccc3c3ccccc32)cc(-n2c3ccccc3c3ccccc32)c1] | Appl. Phys. Lett, 82, 2422 (2003) |
| | 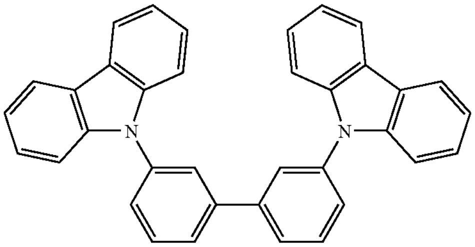 [SMILES: c1cc(-c2cccc(-n3c4ccccc4c4ccccc43)c2)cc(-n2c3ccccc3c3ccccc32)c1] | US20070190359 |

TABLE 2-continued
| MATERIAL | EXAMPLES OF MATERIAL | PUBLICATIONS |
| --- | --- | --- |
| Dibenzothiophene/ Dibenzofuran-carbazole compounds | 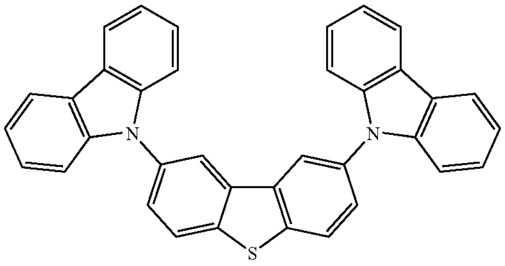 [SMILES: c1ccc2c(c1)c1ccccc1n2-c1ccc2sc3ccc(-n4c5ccccc5c5ccccc54)cc3c2c1] | WO2006114966, US20090167162 |
| | 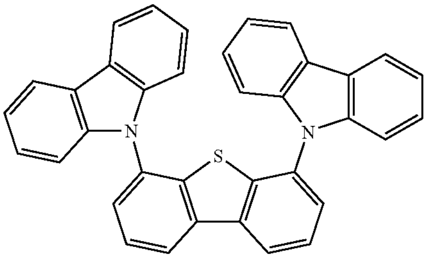 [SMILES: c1cc(-n2c3ccccc3c3ccccc32)c2sc3c(-n4c5ccccc5c5ccccc54)cccc3c2c1] | US20090167162 |
| | 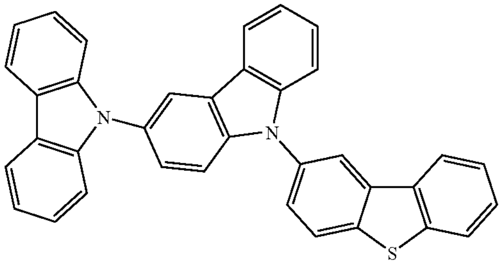 [SMILES: c1ccc2c(c1)sc1ccc(-n3c4ccccc4c4cc(-n5c6ccccc6c6ccccc65)ccc43)cc12] | WO2009086028 |
| | 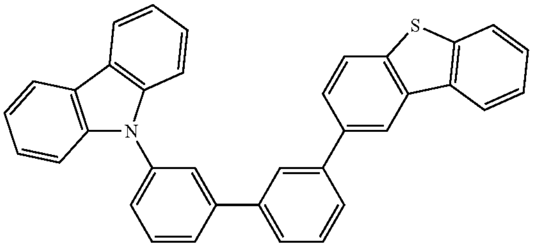 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 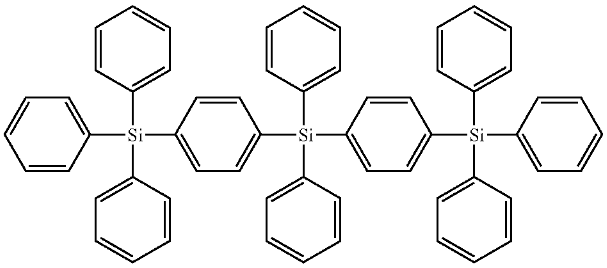 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 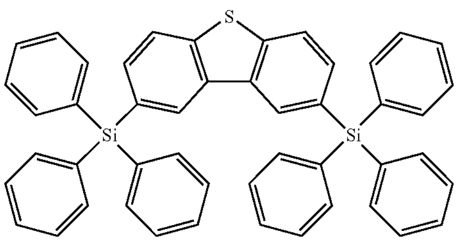 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued
| MATERIAL | EXAMPLES OF MATERIAL | PUBLICATIONS |
|---|---|---|
| Silicon/Germanium aryl compounds | 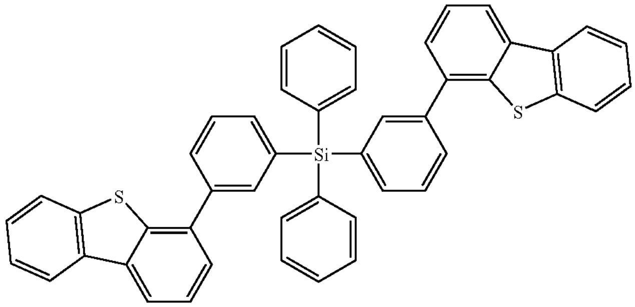 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 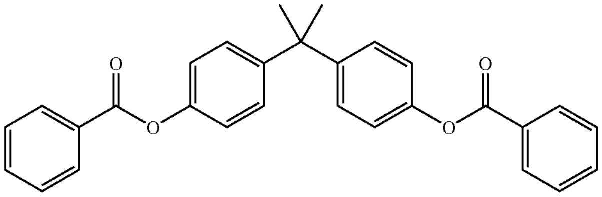 [SMILES: CC(C)(c1ccc(OC(=O)c2ccccc2)cc1)c1ccc(OC(=O)c2ccccc2)cc1] | WO2006100298 |
| High triplet metal organometallic complex | 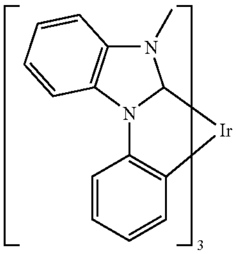 | U.S. Pat. No. 7,154,114 |
| Phosphorescent dopants<br>Red dopants | | |
| Heavy metal porphyrins (e.g., PtOEP) | 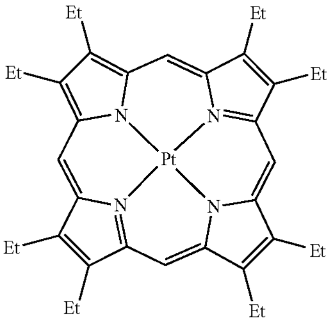 | Nature 395, 151 (1998) |
| Iridium(III) organometallic complexes | 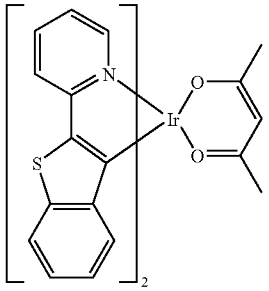 | Appl. Phys. Lett. 78, 1622 (2001) |

TABLE 2-continued
| MATERIAL | EXAMPLES OF MATERIAL | PUBLICATIONS |
|---|---|---|
| | 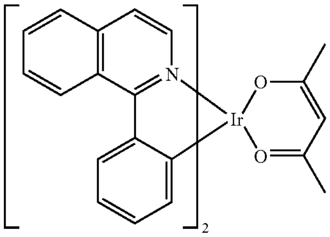 | US2006835469 |
| | 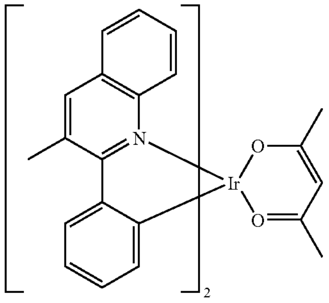 | US2006835469 |
| | 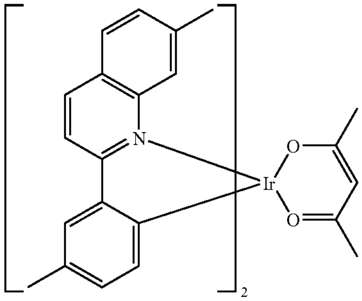 | US20060202194 |
| | 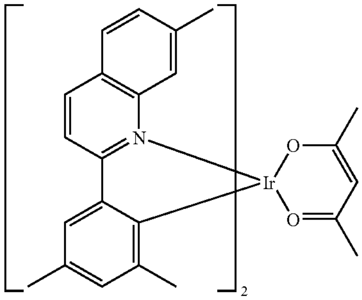 | US20060202194 |
| | 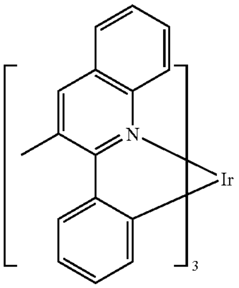 | US20070087321 |

TABLE 2-continued
| MATERIAL | EXAMPLES OF MATERIAL | PUBLICATIONS |
|---|---|---|
| | 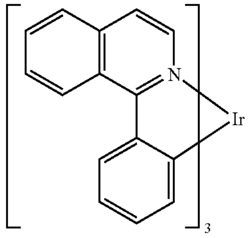 | US20070087321 |
| | 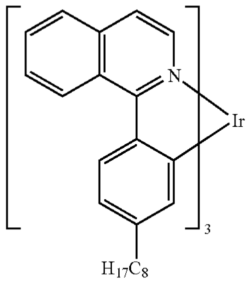 | Adv. Mater. 19, 739 (2007) |
| | 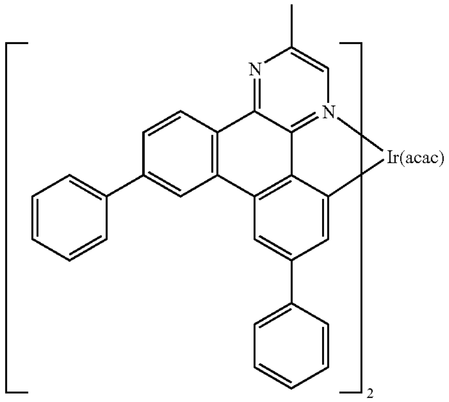 | WO2009100991 |
| | 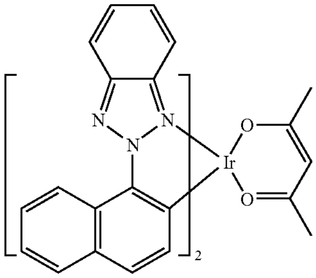 | WO2008101842 |
| Platinum(II) organometallic complexes | 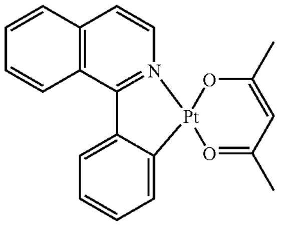 | WO2003040257 |

TABLE 2-continued
| MATERIAL | EXAMPLES OF MATERIAL | PUBLICATIONS |
|---|---|---|
| Osminum(III) complexes | 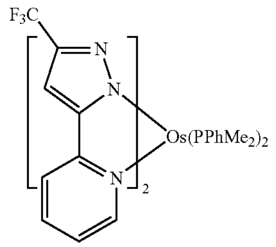 | Chem. Mater. 17, 3532 (2005) |
| Ruthenium(II) complexes | 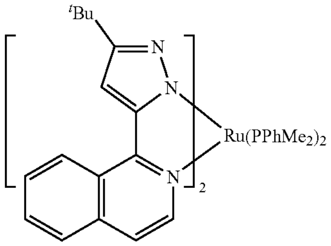 | Adv. Mater. 17, 1059 (2005) |
| Rhenium (I), (II), and (III) complexes | 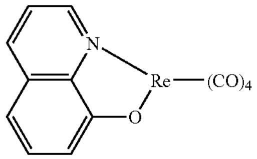 | US20050244673 |
| Green dopants | | |
| Iridium(III) organometallic complexes | 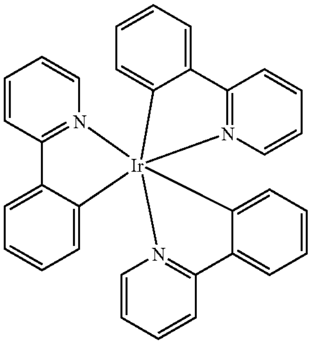 and its derivatives | Inorg. Chem. 40, 1704 (2001) |
| | 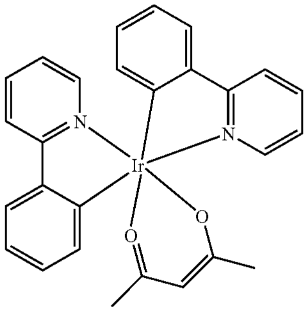 | US20020034656 |

TABLE 2-continued
| MATERIAL | EXAMPLES OF MATERIAL | PUBLICATIONS |
| --- | --- | --- |
| | 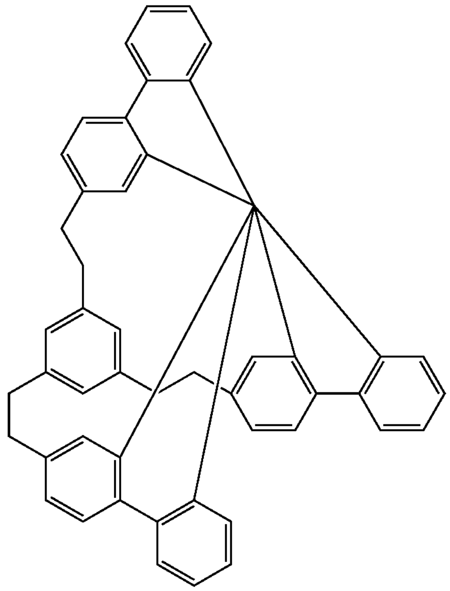 | U.S. Pat. No. 7,332,232 |
| | 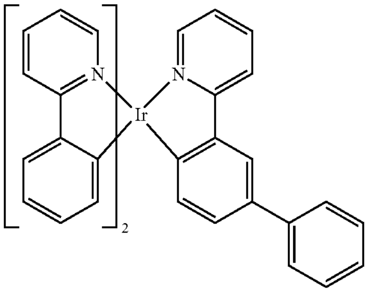 | US20090108737 |
| | 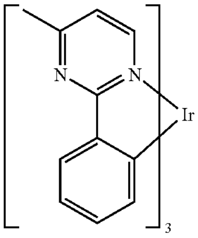 | US20090039776 |
| | 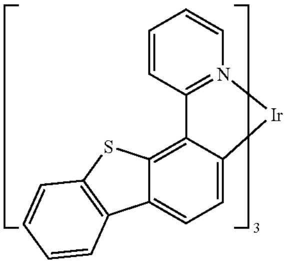 | U.S. Pat. No. 6,921,915 |

TABLE 2-continued
| MATERIAL | EXAMPLES OF MATERIAL | PUBLICATIONS |
|---|---|---|
| | 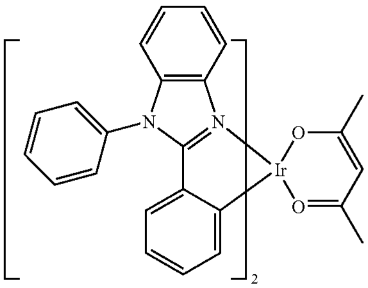 | U.S. Pat. No. 6,687,266 |
| | 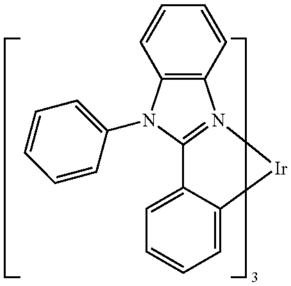 | Chem. Mater. 16, 2480 (2004) |
| | 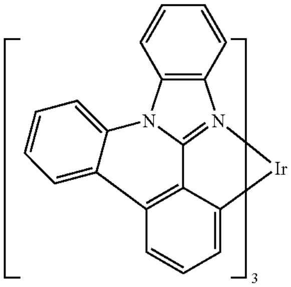 | US20070190359 |
| | 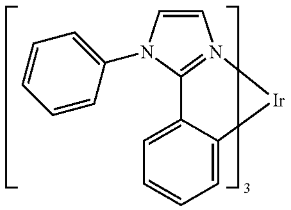 | US 20060008670 JP2007123392 |
| | 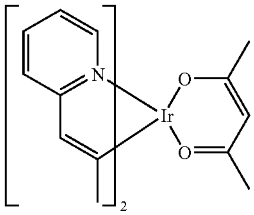 | Adv. Mater. 16, 2003 (2004) |

TABLE 2-continued
| MATERIAL | EXAMPLES OF MATERIAL | PUBLICATIONS |
|---|---|---|
| | 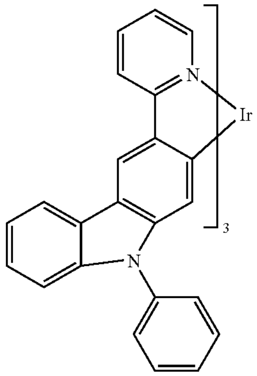 | Angew. Chem. Int. Ed. 2006, 45, 7800 |
| | 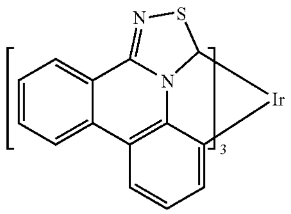 | WO2009050290 |
| | 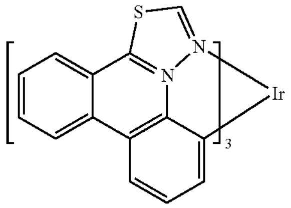 | US20090165846 |
| | 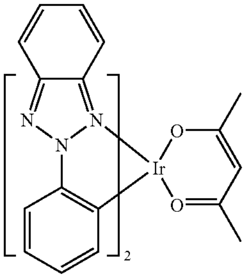 | US20080015355 |
| Monomer for polymeric metal organometallic compounds | 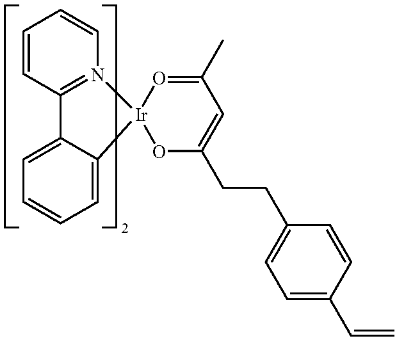 | U.S. Pat. No. 7,250,226, U.S. Pat. No. 7,396,598 |

TABLE 2-continued
| MATERIAL | EXAMPLES OF MATERIAL | PUBLICATIONS |
|---|---|---|
| Pt(II) organometallic complexes, including polydentated ligands | 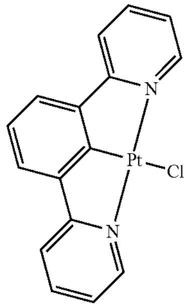 | Appl. Phys. Lett. 86, 153505 (2005) |
| | 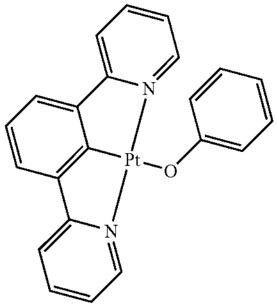 | Appl. Phys. Lett. 86, 153505 (2005) |
| | 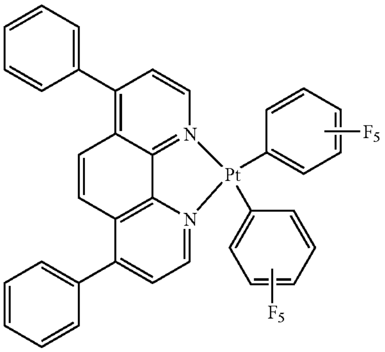 | Chem. Lett. 34, 592 (2005) |
| | 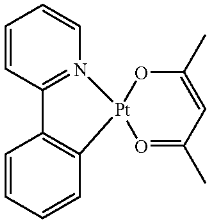 | WO2002015645 |
| | 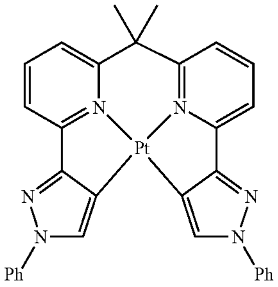 | US20060263635 |

TABLE 2-continued
| MATERIAL | EXAMPLES OF MATERIAL | PUBLICATIONS |
|---|---|---|
| Cu complexes | 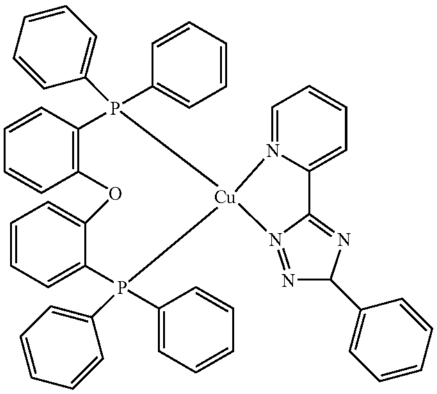 | WO2009000673 |
| Gold complexes | 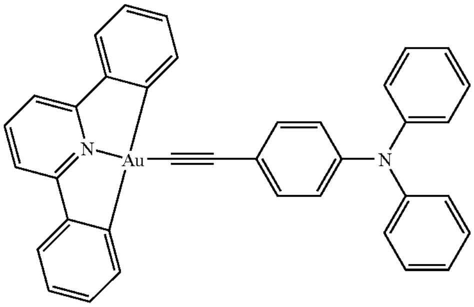 | Chem. Commun. 2906 (2005) |
| Rhenium(III) complexes | 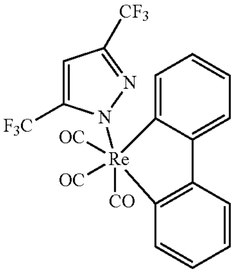 | Inorg. Chem. 42, 1248 (2003) |
| Deuterated organometallic complexes | 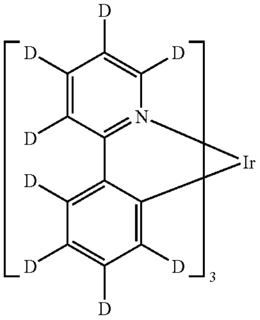 | US20030138657 |

TABLE 2-continued
| MATERIAL | EXAMPLES OF MATERIAL | PUBLICATIONS |
|---|---|---|
| Organometallic complexes with two or more metal centers | 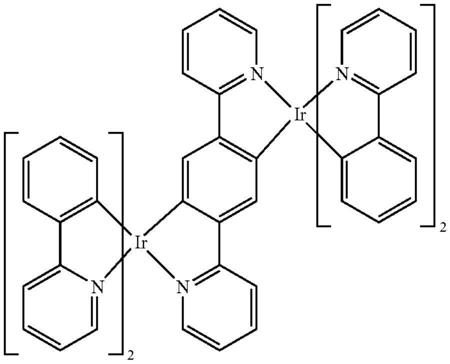 | US20030152802 |
| | 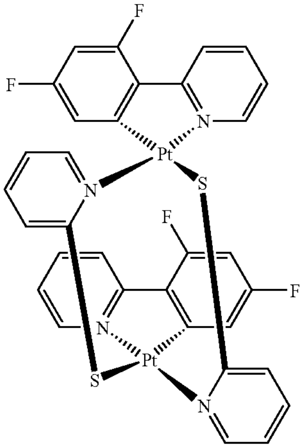 | U.S. Pat. No. 7,090,928 |
| Blue dopants | | |
| Iridium(III) organometallic complexes | 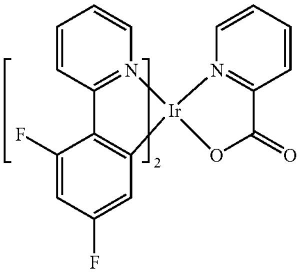 | WO2002002714 |
| | 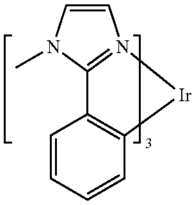 | WO2006009024 |
| | 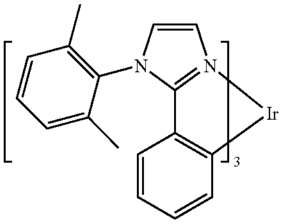 | US20060251923 |

TABLE 2-continued
| MATERIAL | EXAMPLES OF MATERIAL | PUBLICATIONS |
|---|---|---|
| | 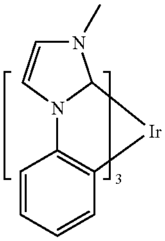 | U.S. Pat. No. 7,393,599, WO2006056418, US20050260441, WO2005019373 |
| | 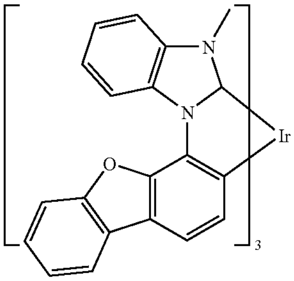 | U.S. Pat. No. 7,534,505 |
| | 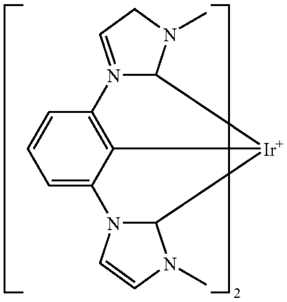 | U.S. Pat. No. 7,445,855 |
| | 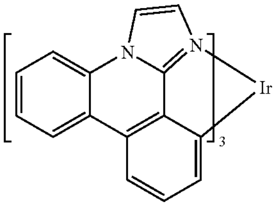 | US20070190359, US20080297033 |
| | 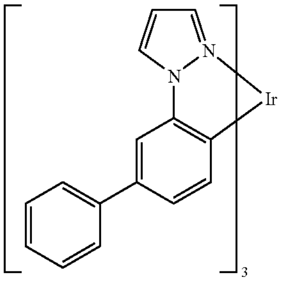 | U.S. Pat. No. 7,338,722 |
| | 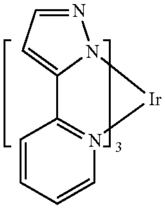 | US20020134984 |

TABLE 2-continued
| MATERIAL | EXAMPLES OF MATERIAL | PUBLICATIONS |
|---|---|---|
| | 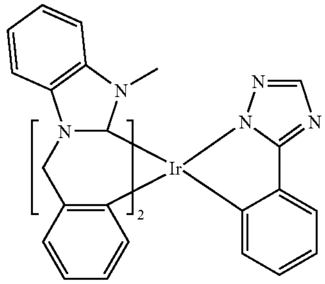 | Angew. Chem. Int. Ed. 47, 1 (2008) |
| | 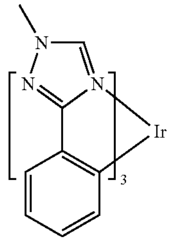 | Chem. Mater. 18, 5119 (2006) |
| | 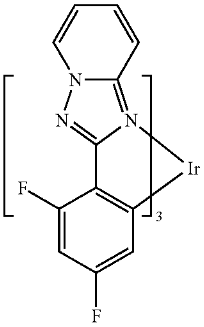 | Inorg. Chem. 46, 4308 (2007) |
| | 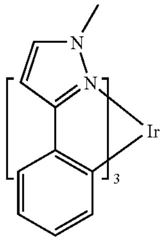 | WO2005123873 |
| | 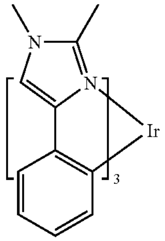 | WO2005123873 |
| | 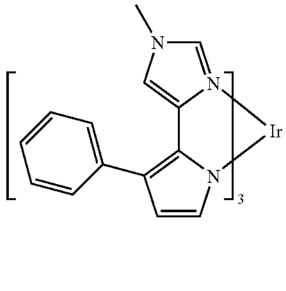 | WO2007004380 |

TABLE 2-continued
| MATERIAL | EXAMPLES OF MATERIAL | PUBLICATIONS |
|---|---|---|
| | 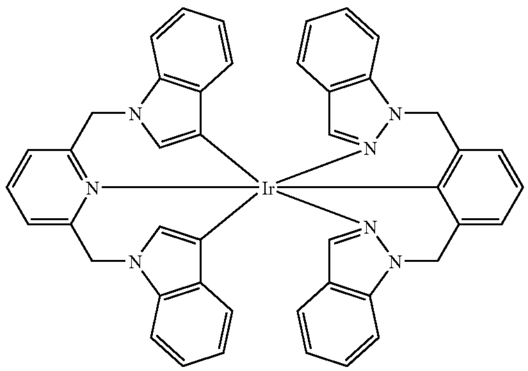 | WO2006082742 |
| Osmium(II) complexes | 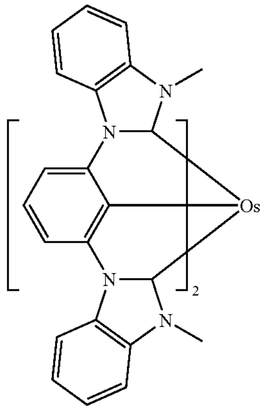 | U.S. Pat. No. 7,279,704 |
| | 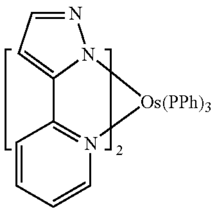 | Organometallics 23, 3745 (2004) |
| Gold complexes | 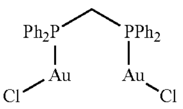 | Appl. Phys. Lett.74,1361 (1999) |
| Platinum(II) complexes | 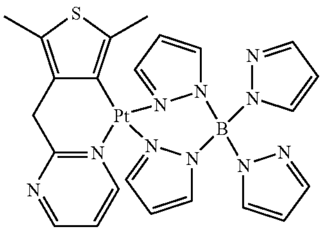 | WO2006098120, WO2006103874 |

TABLE 2-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 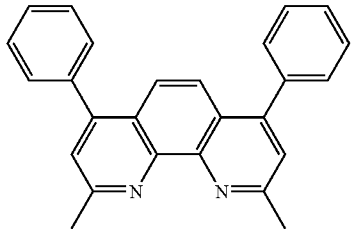 [SMILES: Cc1cc(-c2ccccc2)c2ccc3c(-c4ccccc4)cc(C)nc3c2n1] | Appl. Phys. Lett. 75, 4 (1999) |
| | 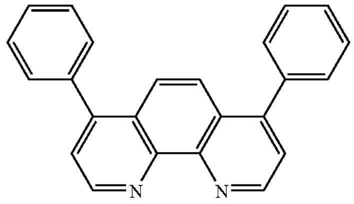 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 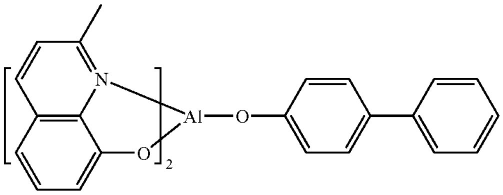 | Appl. Phys. Lett. 81, 162 (2002) |
| 5-member ring electron deficient heterocycles such as triazole, oxadiazole, imidazole, benzoimidazole | 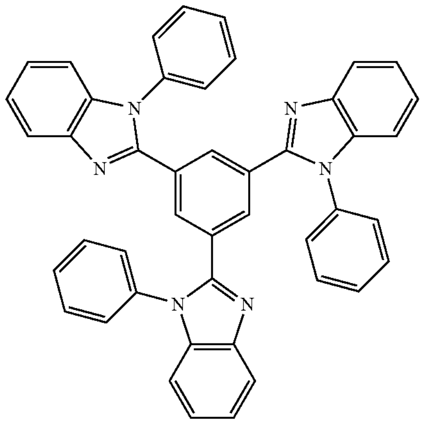 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 2-continued
| MATERIAL | EXAMPLES OF MATERIAL | PUBLICATIONS |
|---|---|---|
| Triphenylene compounds | 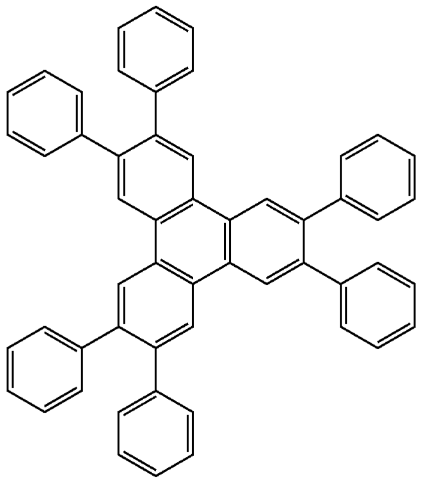 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 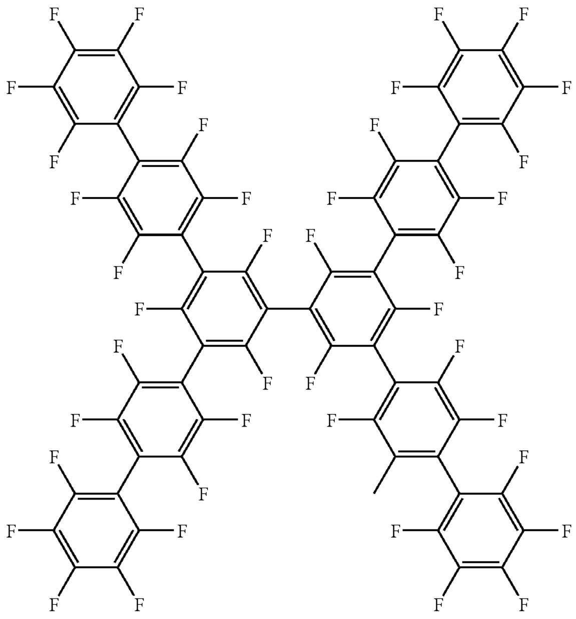 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 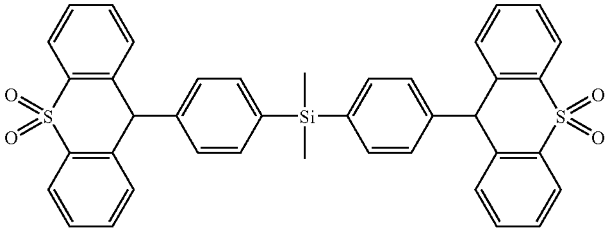 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 2-continued
| MATERIAL | EXAMPLES OF MATERIAL | PUBLICATIONS |
|---|---|---|
| Electron transporting materials | | |
| Anthracene-benzoimidazole compounds | 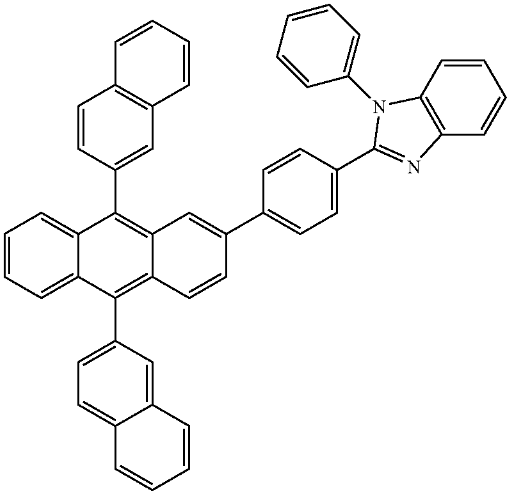 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 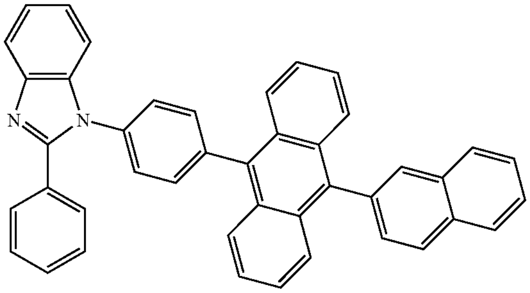 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 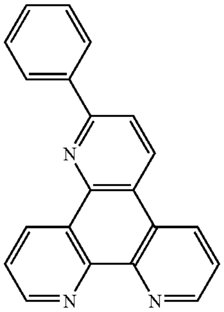 [SMILES: c1ccc(-c2ccc3c4cccnc4c4ncccc4c3n2)cc1] | US20090115316 |
| Anthracene-benzothiazole compounds | 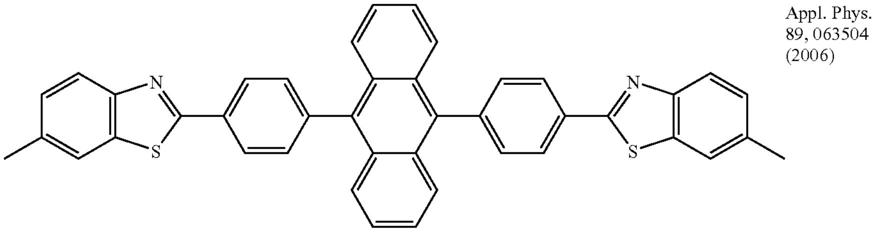 | Appl. Phys. Lett. 89, 063504 (2006) |
| Metal 8-hydroxyquinolates (e.g., $Alq_3$, $Zrq_4$) | 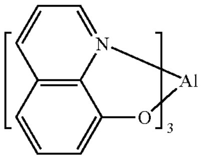 | Appl. Phys. Lett. 51, 913 (1987) U.S. Pat. No. 7,230,107 |

TABLE 2-continued
| MATERIAL | EXAMPLES OF MATERIAL | PUBLICATIONS |
| --- | --- | --- |
| Metal hydroxybenoquinolates | 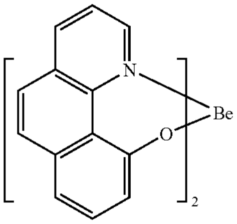 | Chem. Lett. 5, 905 (1993) |
| Bathocuprine compounds such as BCP, BPhen, etc | 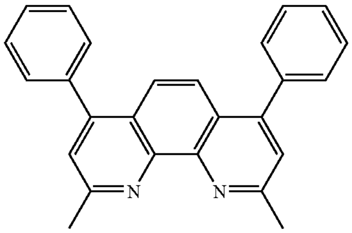 [SMILES: Cc1cc(-c2ccccc2)c2ccc3c(-c4ccccc4)cc(C)nc3c2n1] | Appl. Phys. Lett. 91, 263503 (2007) |
| | 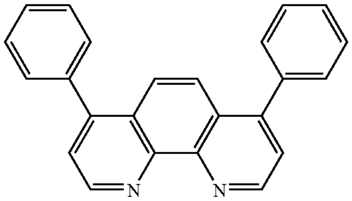 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g.,triazole, oxadiazole, imidazole, benzoimidazole) | 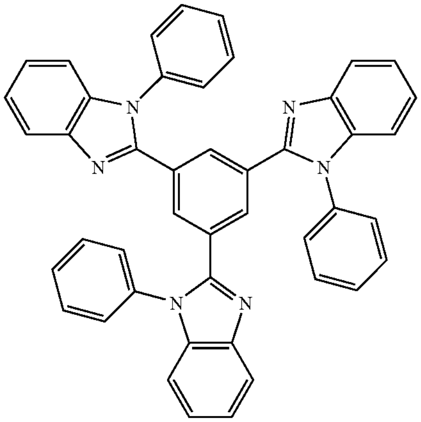 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 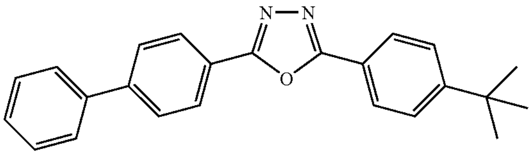 [SMILES: CC(C)(C)c1ccc(-c2nnc(-c3ccc(-c4ccccc4)cc3)o2)cc1] | Appl. Phys. Lett. 55, 1489 (1989) |
| | 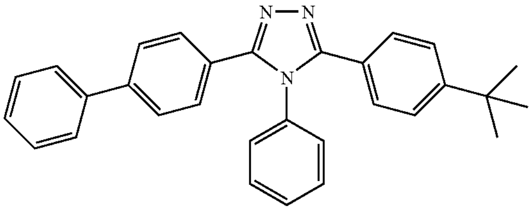 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |

TABLE 2-continued
| MATERIAL | EXAMPLES OF MATERIAL | PUBLICATIONS |
|---|---|---|
| Silole compounds | 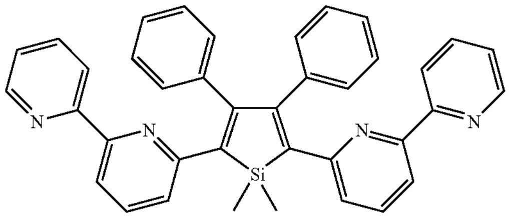 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 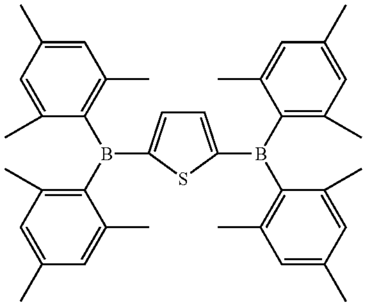 | J. Am. Chem. Soc. 120, 9714 (1998) |
| Fluorinated aromatic compounds | 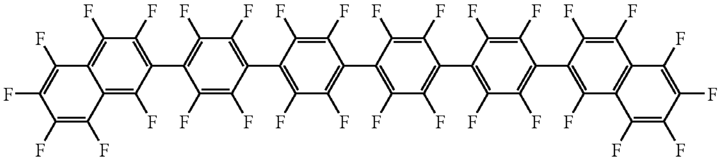 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 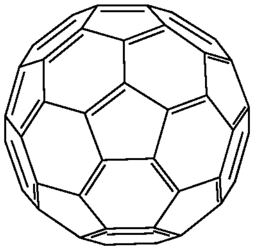 | US20090101870 |
| Triazine complexes | 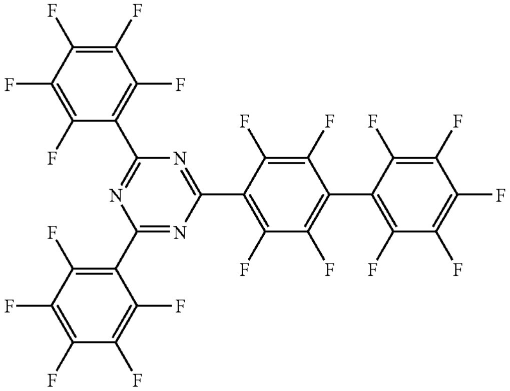 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 2-continued

| MATERIAL | EXAMPLES OF MATERIAL | PUBLICATIONS |
|---|---|---|
| Zn (N^N) complexes | 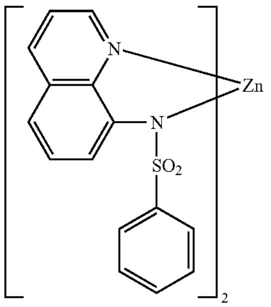 | U.S. Pat. No. 6,528,187 |

EXPERIMENTAL

Compound Examples

Example 1

Synthesis of Compound 1

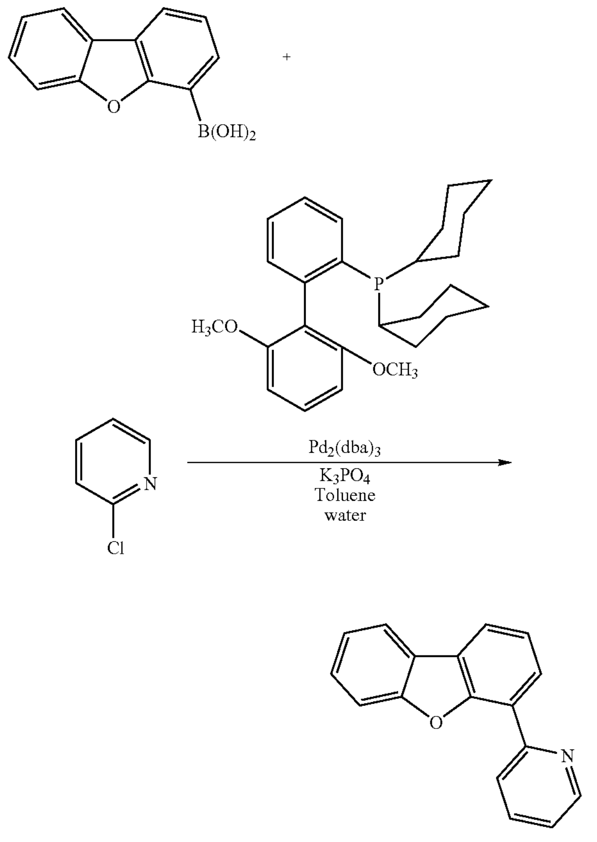 [SMILES: OB(O)c1cccc2c1oc1ccccc12 ; COc1cccc(OC)c1-c1ccccc1P(C1CCCCC1)C1CCCCC1 ; Clc1ccccn1 ; c1ccc(-c2cccc3c2oc2ccccc23)nc1]

Synthesis of 2-(dibenzo[b,d]furan-4-yl)pyridine. 4-dibenzofuranboronic acid (5.0 g, 23.6 mmol), 2-chloropyridine (2.2 g, 20 mmol), dicyclohexyl(2',6'-dimethoxybiphenyl-2-yl)phosphine (S-Phos) (0.36 g, 0.8 mmol), and potassium phosphate (11.4 g, 50 mmol) were mixed in 100 mL of toluene and 10 mL of water. Nitrogen is bubbled directly into the mixture for 30 minutes. Next, $Pd_2(dba)_3$ was added (0.18 g, 0.2 mmol) and the mixture was heated to reflux under nitrogen for 8 h. The mixture was cooled and the organic layer was separated. The organic layers are washed with brine, dried over magnesium sulfate, filtered, and evaporated to a residue. The residue was purified by column chromatography eluting with dichloromethane. 4.5 g of desired product was obtained after purification.

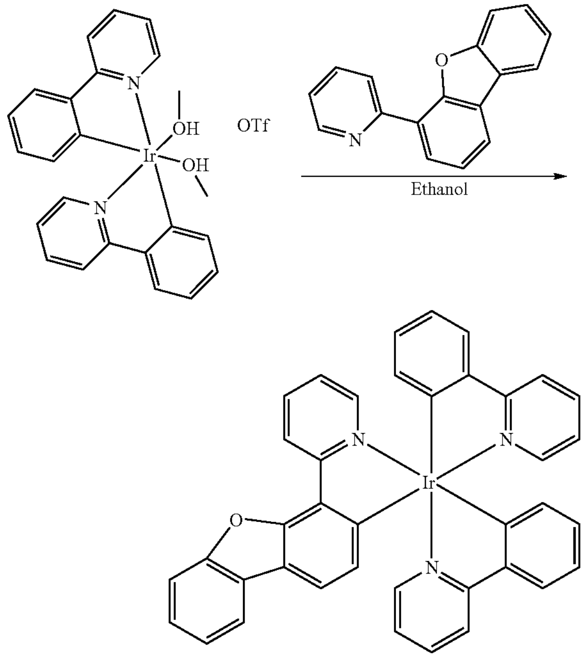

Compound 1

Synthesis of Compound 1. The iridium triflate precursor (0.97 g, 1.4 mmol) and 2-(dibenzo[b,d]furan-4-yl)pyridine (1.0 g, 4.08 mmol) were mixed in 50 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 0.9 g of pure product was obtained after the column purification. (HPLC purity: 99.9%)

Example 2

Synthesis of Compound 2

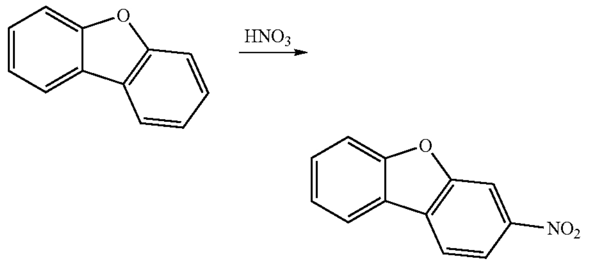

Synthesis of 3-nitrodibenzofuran. To 80 mL trifluoroacetic acid in a 250 mL round bottom flask was added dibenzofuran (7.06 g, 42 mmol) and stirred vigorously to dissolve the content at room temperature. The solution was then cooled on ice and 1.2 equivalent 70% $HNO_3$ (4.54 g, 50.40 mmol) in 20 mL trifluoroacetic acid was poured into the stirred solution slowly. After stirring for 30 minutes contents from the flask was poured into 150 mL ice-water and stirred for another 15 minutes. Off white color precipitate was then filtered out and finally washed with 2M NaOH and water. Moist material was then recrystallized from 1.5 L boiling ethanol in the form of light yellow color crystal. 7.2 g of product was isolated.

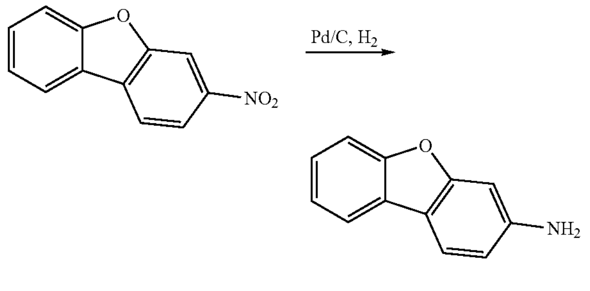

Synthesis of 3-aminodibenzofuran. 3-nitrodibenzofuran (6.2 g, 29.08 mmol) was dissolved in 360 mL ethyl acetate and was degassed 5 minutes by passing nitrogen gas through the solution. 500 mg of Pd/C was added to the solution and the content was hydrogenated at 60 psi pressure. Reaction was let go until pressure in hydrogenation apparatus stabilizes at 60 psi for 15 minutes. Reaction content was then filtered through a small celite pad and off white color product was obtained. (5.3 g, 28.9 mmol)

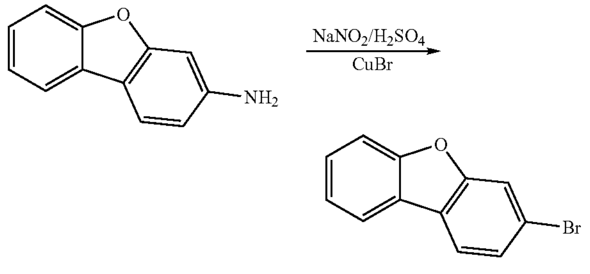

Synthesis of 3-bromodibenzofuran. $NaNO_2$ (2.21 g, 32.05 mmol) was dissolved in 20 mL conc. $H_2SO_4$ in conical flask kept at 0° C. Solution of 2-aminodibenzofuran (5.3 g, 28.9 mmol) in minimum volume of glacial acetic acid was then slowly added to the flask so that temperature never raised above 5-8° C. and the mixture was stirred at 0° C. for another 1.5 h. 100 mL ether was added to the stirred mixture and precipitate of corresponding diazo salt immediately settled down. Brown color diazo salt was immediately filtered out and transferred to a flask containing CuBr (6.25 g, 43.5 mmol) in 150 mL 48% HBr. The flask was then placed in a water bath maintained at 64° C. and stirred for 2 h. After cooling down to room temperature, the dark color reaction content was filtered out and the precipitate was washed with water twice. Isolated solid was then flashed over Silica gel column with 5-10% DCM/Hexane to give 4.79 g final compound.

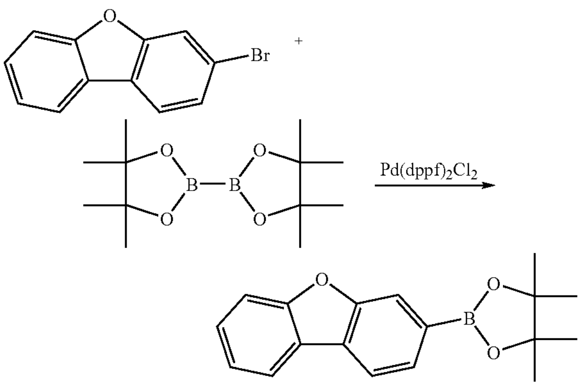

Synthesis of 2-(dibenzo[b,d]furan-3-yl)-4,4,5,5-tetramethyl-1,3,2-dioxaborolane. 3-bromodibenzofuran (4.79 g, 19.39 mmol), bispinacolatodiboron (6.4 g, 25.2 mmol), KOAc (7.61 g, 77.54 mmol) was added to 100 mL of dioxane in a r.b. flask. Content was degassed for 30 minutes under bubbling nitrogen gas and $Pd(dppf)_2Cl_2$ (158 mg, 0.019 mmol) was added to the reaction mixture. After degassing for another 10 minutes, the reaction mixture was heated to 80° C. and stirred overnight. Reaction flask was then cooled to room temperature and filtered through a pad of celite. Deep brown color solution was then partitioned in between brine and ethyl acetate. Organic layer was collected, dried over anhydrous $Na_2SO_4$ and excess solvent was evaporated under vacuum. Brown colored solid was then dry loaded in silica gel column and quickly flashed with 5% ethylacetate/hexane/0.005% triethylamine to give 5.08 g final product.

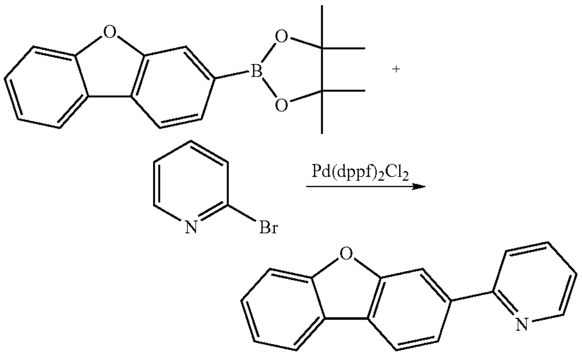

Synthesis of 2-(dibenzofuran-3-yl)pyridine. Dibenzofuran boronate ester (5.85 g, 20 mmol), 2-bromopyridine (2.93 mL, 30 mmol), 30 mL 2 M $Na_2CO_3$ (60 mmol) was slurried in 200 mL toluene/ethanol (1:1) in a 500 mL 3-neck round bottom flask and degassed for 30 minutes under bubbling nitrogen gas. $Pd(dppf)_2Cl_2$ (160 mg, 0.2 mmol) was added to the slurry and degassing continued for another 10 minutes. The reaction contents were then refluxed overnight. Reaction content was cooled to room temperature and filtered thru a small celite pad. Brown color biphasic solution was then partitioned between brine and ethylacetate. Organic layer was dried over anhydrous $Na_2SO_4$ and excess solvent was removed under vacuum. Residue from previous step was dry loaded in silica gel column and eluted with 5-8% ethylacetate/hexane to give 4.3 g final product.

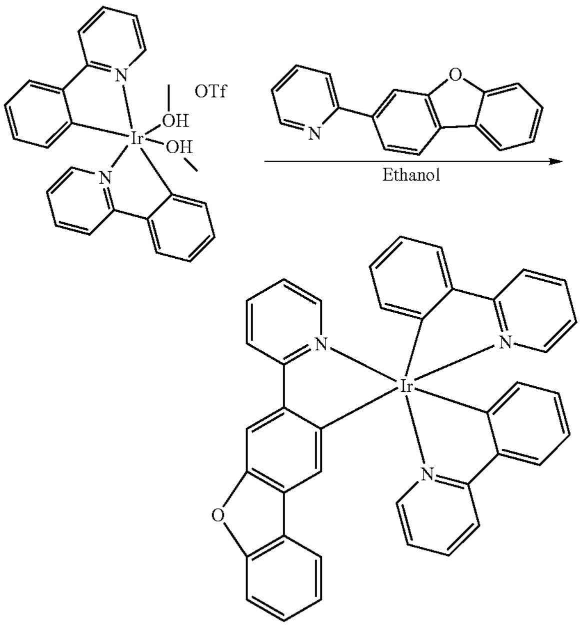

Compound 2

Synthesis of Compound 2. The iridium triflate precursor (2.8 g, 3.9 mmol), 2-(dibenzofuran-3-yl)pyridine (4 g, 16.3 mmol) were refluxed in 100 mL ethanol overnight. Bright yellow precipitate was filtered out, dried and dry loaded in a silica gel column. 210 mg final compound was isolated after elution with 3:2 DCM/hexane.

Example 3

Synthesis of Compound 4

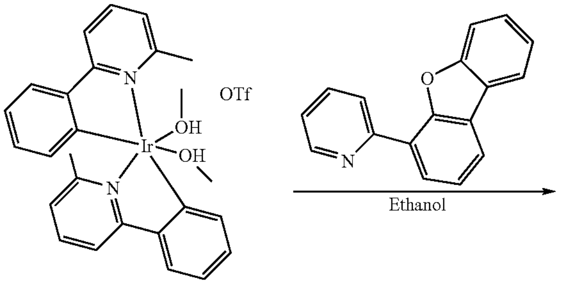

-continued

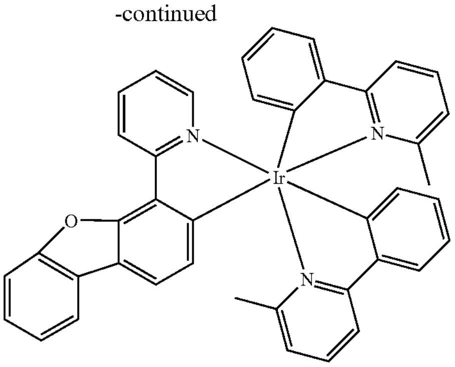

Compound 4

Synthesis of Compound 4. The iridium triflate precursor (1.6 g, 2.2 mmol) and 2-(dibenzo[b,d]furan-4-yl)pyridine (1.6 g, 6.5 mmol) were mixed in 50 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.4 g of pure product was obtained after the column purification.

Example 4

Synthesis of Compound 10

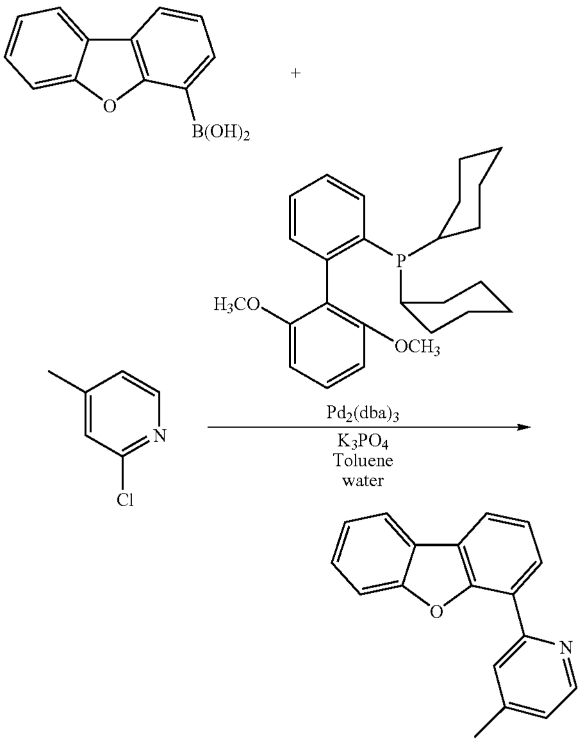

Synthesis of 4-methyl-2-(dibenzo[b,d]furan-4-yl)pyridine. 4-dibenzofuranboronic acid (5.0 g, 23.6 mmol), 2-chloro-4-methylpyridine (2.6 g, 20 mmol), dicyclohexyl (2',6'-dimethoxybiphenyl-2-yl)phosphine (S-Phos) (0.36 g, 0.8 mmol), and potassium phosphate (11.4 g, 50 mmol) were mixed in 100 mL of toluene and 10 mL of water. Nitrogen is bubbled directly into the mixture for 30 minutes. Next, $Pd_2(dba)_3$ was added (0.18 g, 0.2 mmol) and the mixture was heated to reflux under nitrogen for 8 h. The mixture was cooled and the organic layer was separated. The organic layers are washed with brine, dried over magnesium sulfate, filtered, and evaporated to a residue. The residue was purified by column chromatography eluting with dichloromethane. 4.7 g of desired product was obtained after purification.

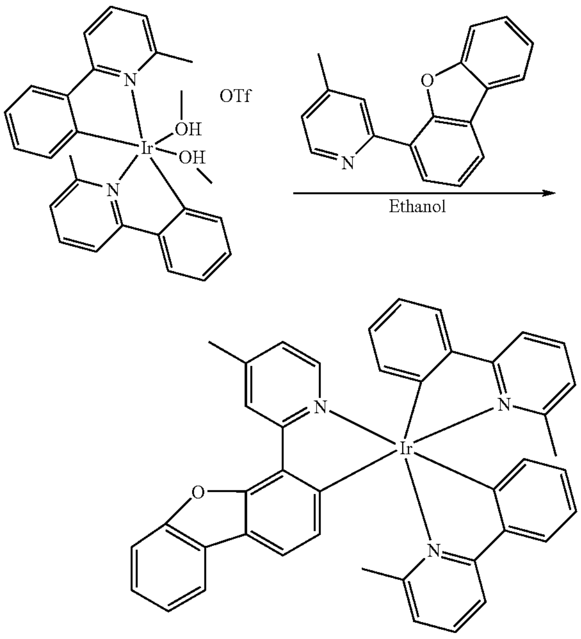

Compound 10

Synthesis of Compound 10. The iridium triflate precursor (2.0 g, 2.7 mmol) and 4-methyl-2-(dibenzo[b,d]furan-4-yl) pyridine (2.1 g, 8.1 mmol) were mixed in 60 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.6 g of pure product was obtained after the column purification.

Example 5

Synthesis of Compound 29

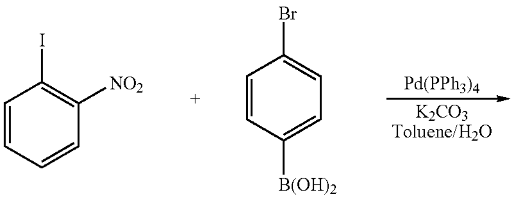

-continued

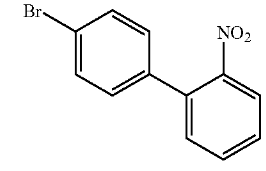

Synthesis of 4'-bromo-2-nitrobiphenyl. o-iodonitrobenzene (9.42 g, 37.84 mmol), 4-bromobenzeneboronic acid (7.6 g, 37.84 mmol), potassium carbonate (21 g, 151.36 mmol) was added to 190 mL DME/water (3:2) solution and degassed for 30 minutes. $Pd(PPh_3)_4$ (437 mg, 0.38 mmol) was added to the slurry under nitrogen and the slurry was degassed for another 5 minutes. The reaction was refluxed under nitrogen for 6 h. Content of the flask was filtered through a pad of celite and partitioned in ethyl acetate and brine. Organic phase was dried over anhydrous $Na_2SO_4$ and evaporated under vacuum. Crude yellow oil was flashed over silica gel using 5% ethylacetate/hexane. Final compound was isolated as colorless oil (9.8 g, 35.4 mmol).

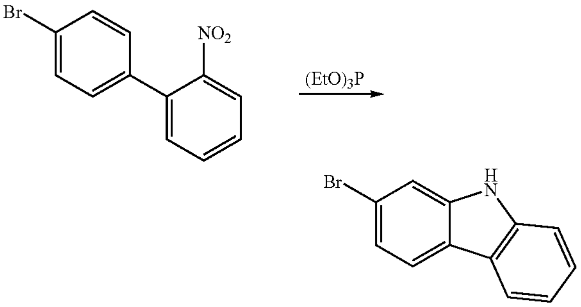

Synthesis of 2-bromo-9H-carbazole. 4'-bromo-2-nitrobiphenyl (9.8 g, 35.4 mmol) was refluxed with 30 mL triethylphosphite overnight. After cooling down the solution to room temperature, 40 mL 6(N)HCl was added to it slowly and heated to 80° C. for 3 h. Acidic solution was halfway neutralized with conc. NaOH, rest of the acidic solution was neutralized with solid $Na_2CO_3$. Cloudy solution was extracted three times with ethylacetate (500 mL). Combined organic layer was evaporated under vacuum and crude was flashed on silica gel (15% to 30% ethylacetate/hexane). 4.1 g final compound was isolated as off white solid.

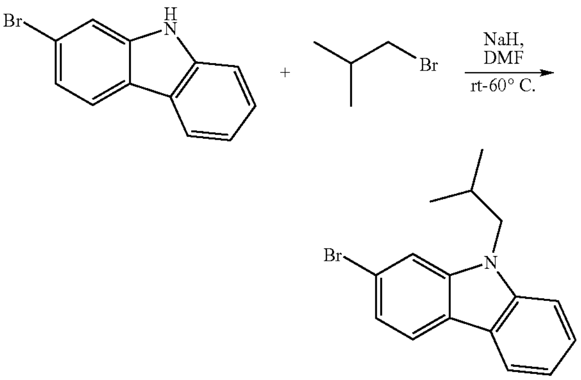

Synthesis of 2-bromo-9-isobutyl-9H-carbazole. 2-bromo-9H-carbazole (4.1 g, 16.74 mmol) was dissolved in DMF. To the stirred solution was slowly added NaH (1.8 g, 75.5 mmol) in 3 portions. Isobutylbromide (4.8 mL, 43.2 mmol) was added to the stirred slurry and after waiting for 20 minute, warmed up to 60° C. for 4 h. Reaction mixture was cooled to room temperature and carefully quenched with drop wise addition of saturated $NH_4Cl$ solution. Content was then partitioned in brine and ethylacetate. Organic layer was dried over anhydrous $Na_2SO_4$ and evaporated under vacuum. The crude product was flashed over silica gel with 10% ethylacetate/hexane. Final product (4.45 g, 14.8 mmol) was isolated as white solid.

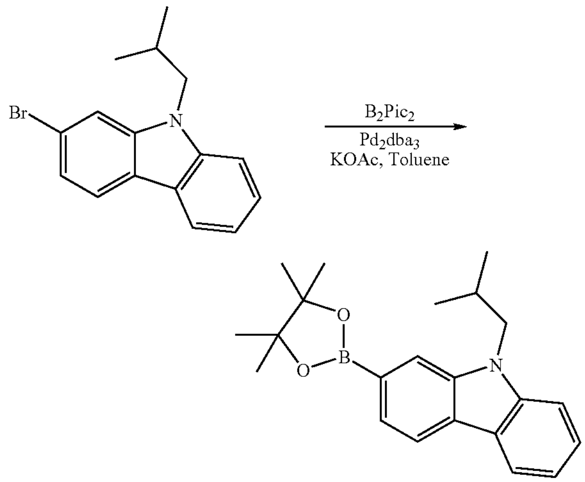

Synthesis of 9-isobutyl-2-pinacolboron-9H-carbazole. 2-bromo-9-isobutyl-9H-carbazole (4.45 g, 14.78 mmol), bisboronpinacolate (4.7 g, 18.5 mmol), potassium acetate (5.8 g, 59.1 mmol) were taken in 75 mL anhydrous toluene and degassed for 30 minutes. $Pd_2dba_3$ (362 mg, 0.443 mmol) was added to the slurry under nitrogen and the slurry was degassed for another 5 minutes. After overnight reflux, content of the reaction was cooled down and filtered through a celite pad. Toluene solution was partitioned in water and ethylacetate. Organic layer was dried over anhydrous $Na_2SO_4$ and solvent was evaporated under vacuum. Solid crude was flashed in silica gel using 10% ethylacetate/hexane. Isolated solid was subjected to Kugelrohr distillation at 133° C. to remove traces of bisboronpinacolate. Final product (4.77 g, 13.7 mmol) was isolated as off white solid.

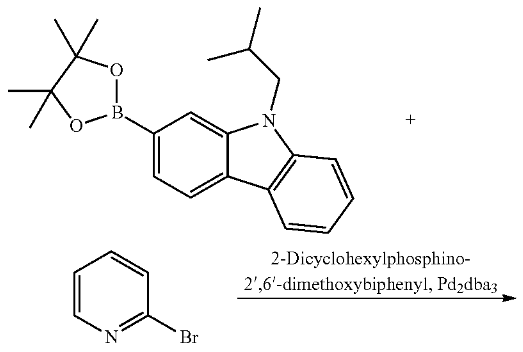

-continued

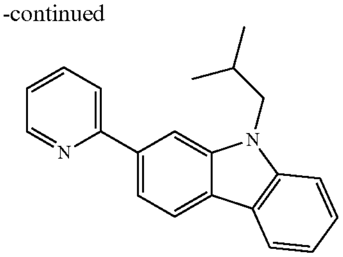

SL-205-90

Synthesis of 9-isobutyl-2-(pyridine-2-yl)-9H-carbazole. 9-isobutyl-2-pinacolboron-9H-carbazole (1.45 g, 4 mmol), 2-bromopyridine (760 mg, 4.8 mmol), 2-dicyclohexylphosphino-2',6'-dimethoxybiphenyl (67 mg, 0.16 mmol), $K_3PO_4.H_2O$ (3.68 g, 16 mmol) were added to 40 mL mixture of 9:1 toluene and water. Contents were degassed for 30 minutes before addition of $Pd_2dba_3$ (37 mg, 0.04 mmol) and degassed for another 5 minutes. After overnight reflux, reaction content was cooled to room temperature and filtered through a pad of celite. Filtrate was partitioned in water and ethylacetate. Organic layer was isolated, dried over anhydrous $Na_2SO_4$ and evaporated under vacuum. Crude was then flashed over silica gel using 10%-30% ethylacetate/hexane to remove the protodeborylation product. Final compound (620 mg, 2.1 mmol) was isolated as white solid.

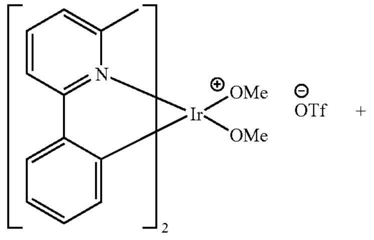

Intermediate-1

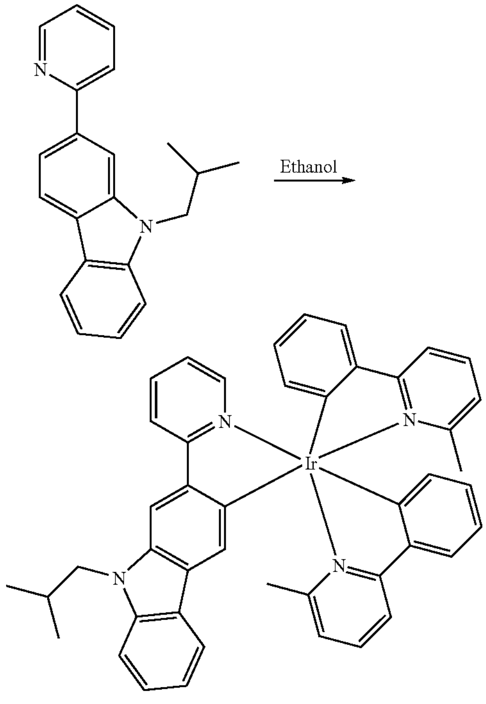

Compound 29

Synthesis of Compound 29. Carbazole ligand (620 mg, 2.1 mmol) from previous step was dissolved in ethanol and Intermediate-1 was added to it under nitrogen. Solution was then refluxed overnight. Deep orange color precipitate was filtered out and flashed over silica gel with 50% DCM/hexane. Isolated product was then sublimed to give 310 mg 99.7% pure product.

Example 6

Synthesis of Compound 7

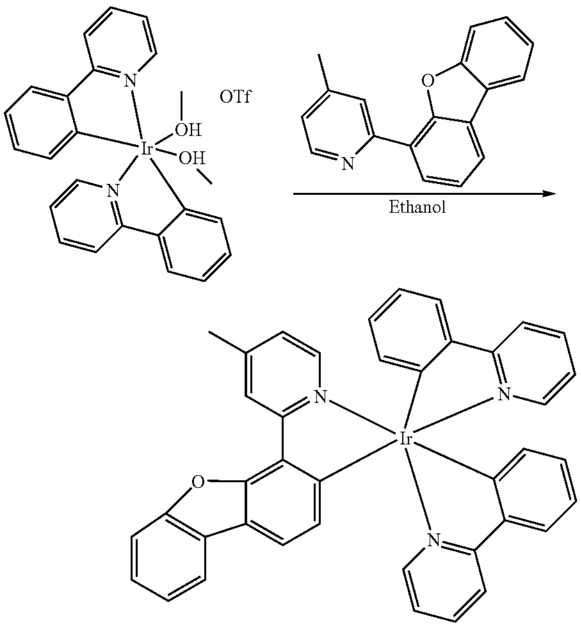

Compound 7

Synthesis of Compound 7. The iridium triflate precursor (2.0 g, 2.7 mmol) and 4-methyl-2-(dibenzo[b,d]furan-4-yl) pyridine (2.1 g, 8.1 mmol) were mixed in 60 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.0 g of pure product was obtained after the column purification.

Example 7

Synthesis of Compound 37

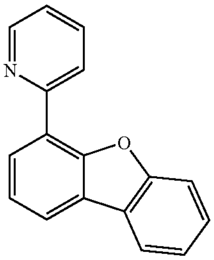

+

-continued

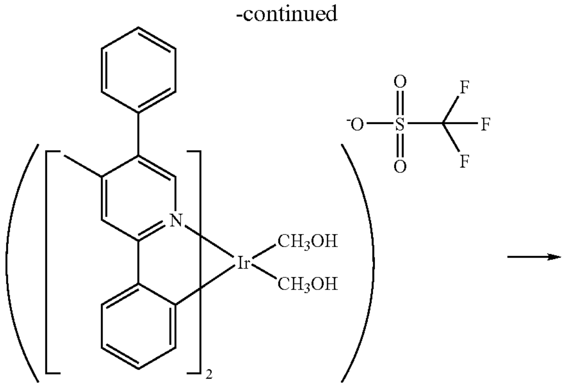

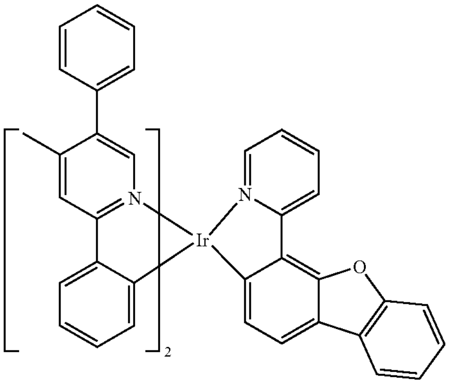

Compound 37

Synthesis of Compound 37. 2-(dibenzo[b,d]furan-4-yl)pyridine (5.0 g, 20.39 mmol) and the iridium triflate (5.0 g, 5.59 mmol) were placed in a 250 mL round bottom flask with 100 mL of a 1:1 solution of ethanol and methanol. The reaction mixture was refluxed for 24 h. A bright yellow precipitate was obtained. The reaction was cooled to room temperature and diluted with ethanol. Celite was added to and the reaction mixture was filtered through a silica gel plug. The plug was washed with ethanol (2×50 mL) followed by hexanes (2×50 mL). The product which remained on the silica gel plug was eluted with dichloromethane into a clean receiving flask. The dichloromethane was removed under vacuum and the product was recrystallized from a combination of dichloromethane and isopropanol. The yellow solid was filtered, washed with methanol followed by hexanes to give bright yellow crystalline product. The product was further purified by recrystallization from toluene followed by recrystallization from acetonitrile to give 1.94 g (37.5% yield) of product with purity 99.5% by HPLC.

Device Examples

All example devices were fabricated by high vacuum (<$10^{-7}$ Torr) thermal evaporation. The anode electrode is 800 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Particular devices are provided wherein an invention compound, Compound 1, 2, 4, 7, 10 or 29, is the emitting dopant and H1 is the host. The organic stack of Device Examples 1-11 consisted of, sequentially from the ITO surface, 100 Å of E1 as the hole injecting layer (HIL), 300 Å of 4,4'-bis-[N-(1- naphthyl)-N-phenylamino]biphenyl (α-NPD) as the hole transport layer (HTL), 300 Å of H1 doped with 7% or 10% of the invention compound, an Ir phosphorescent compound, as the emissive layer (EML), 50 Å of H1 as the blocking layer (BL) and 400 Å of $Alq_3$ (tris-8-hydroxyquinoline aluminum) as the ETL1.

Comparative Examples 1 and 2 were fabricated similarly to the Device Examples, except that E1 and E2. respectively, were used as the emitting dopant.

As used herein, the following compounds have the following structures:

E1

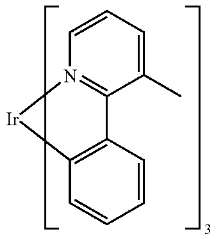

E2

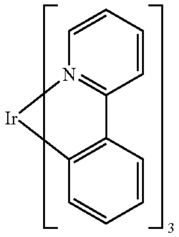

-continued

H1

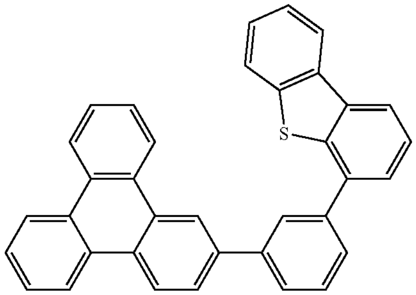

NPD

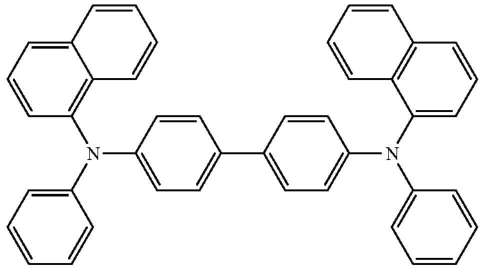

The device structures and device data are summarized below in Table 3 and Table 4. Table 3 shows the device structure, and Table 4 shows the corresponding measured results for the devices. Ex. is an abbreviation of Example.

TABLE 3

| Example | HIL | HTL | Host | A % | BL | ETL |
|---|---|---|---|---|---|---|
| Example 1 | E1 100 Å | NPD 300 Å | H1 | Compound 1 7% | H1 50 Å | Alq 400 Å |
| Example 2 | E1 100 Å | NPD 300 Å | H1 | Compound 1 10% | H1 50 Å | Alq 400 Å |
| Example 3 | E1 100 Å | NPD 300 Å | H1 | Compound 2 7% | H1 50 Å | Alq 400 Å |
| Example 4 | E1 100 Å | NPD 300 Å | H1 | Compound 2 10% | H1 50 Å | Alq 400 Å |
| Example 5 | E1 100 Å | NPD 300 Å | H1 | Compound 4 7% | H1 50 Å | Alq 400 Å |
| Example 6 | E1 100 Å | NPD 300 Å | H1 | Compound 4 10% | H1 50 Å | Alq 400 Å |
| Example 7 | E1 100 Å | NPD 300 Å | H1 | Compound 7 7% | H1 50 Å | Alq 400 Å |
| Example 8 | E1 100 Å | NPD 300 Å | H1 | Compound 7 10% | H1 50 Å | Alq 400 Å |
| Example 9 | E1 100 Å | NPD 300 Å | H1 | Compound 10 7% | H1 50 Å | Alq 400 Å |
| Example 10 | E1 100 Å | NPD 300 Å | H1 | Compound 10 10% | H1 50 Å | Alq 400 Å |
| Example 11 | E1 100 Å | NPD 300 Å | H1 | Compound 29 10% | H1 50 Å | Alq 400 Å |
| Comparative Example 1 | E1 100 Å | NPD 300 Å | H1 | Compound E1 7% | H1 50 Å | Alq 400 Å |
| Comparative Example 2 | E1 100 Å | NPD 300 Å | H1 | Compound E2 7% | H1 50 Å | Alq 400 Å |

TABLE 4

| | | | | At 1000 nits | | | | At 40 mA/$cm^2$ | |
|---|---|---|---|---|---|---|---|---|---|
| | λ | CIE | | V | LE | EQE | PE | Lo, | $RT_{80\%}$, |
| Example | max, nm | X | Y | (V) | (cd/A) | (%) | (lm/W) | nits | h |
| Ex. 1 | 532 | 0.354 | 0.616 | 6.1 | 60.1 | 15.9 | 31 | 17,382 | 180 |
| Ex. 2 | 530 | 0.367 | 0.607 | 6.5 | 43.2 | 11.5 | 21 | 13,559 | 170 |
| Ex. 3 | 527 | 0.355 | 0.612 | 6.2 | 51.7 | 13.9 | 26.1 | 14,565 | 210 |
| Ex. 4 | 528 | 0.361 | 0.609 | 6 | 44.4 | 11.9 | 23.3 | 13,618 | 360 |
| Ex. 5 | 528 | 0.348 | 0.620 | 5.7 | 68.7 | 18.1 | 37.7 | 19,338 | 98 |
| Ex. 6 | 528 | 0.356 | 0.616 | 5.2 | 70.1 | 18.5 | 42.4 | 21,199 | 96 |
| Ex. 7 | 522 | 0.326 | 0.630 | 5.6 | 68.2 | 18.4 | 38.6 | 18,431 | 120 |
| Ex. 8 | 524 | 0.336 | 0.623 | 5.2 | 58.2 | 15.7 | 35.0 | 17,606 | 200 |
| Ex. 9 | 522 | 0.320 | 0.634 | 5.4 | 70.7 | 19 | 41.4 | 19,996 | 75 |
| Ex. 10 | 522 | 0.327 | 0.631 | 5 | 71.1 | 19.1 | 44.9 | 21,703 | 58 |
| Ex. 11 | 576 | 0.538 | 0.459 | 5.6 | 50.6 | 19 | 28.1 | 14,228 | 800 |
| Comparative Ex. 1 | 527 | 0.344 | 0.614 | 6.4 | 56.7 | 15.6 | 27.6 | 15,436 | 155 |
| Comparative Ex. 2 | 519 | 0.321 | 0.621 | 6 | 45.1 | 12.6 | 23.6 | 13,835 | 196 |

From Device Examples 1-11, it can be seen that the invention compounds as emitting dopants in green phosphorescent devices provide high device efficiency and longer lifetime. In particular, the lifetime, $RT_{80\%}$ (defined as the time for the initial luminance, $L_0$, to decay to 80% of its value, at a constant current density of 40 mA/$cm^2$ at room temperature) of devices containing Compounds 1, 2, 7 and 29 are notably higher than that measured for Comparative Example 2 which used the industry standard emitting dopant $Ir(ppy)_3$. Additionally, Compound 1 in Device Example 1 achieved high device efficiency (i.e., LE of 60 cd/A at 1000 cd/$m^2$), indicating that the inventive compounds comprising a single substituted pyridyl ligand (e.g., pyridyl dibenzofuran) have a high enough triplet energy for efficient green electrophosphorescence.

Additional device structures and device data are summarized below. The device structures and device data are summarized below in Table 5 and Table 6. Table 5 shows the device structure, and Table 6 shows the corresponding measured results for the devices. Ex. is an abbreviation of Example.

As used herein, the following compounds have the following structures:

E1

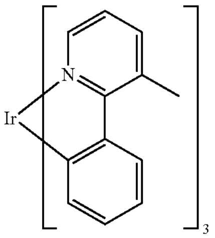

E2

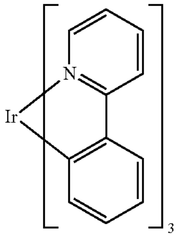

-continued

E3

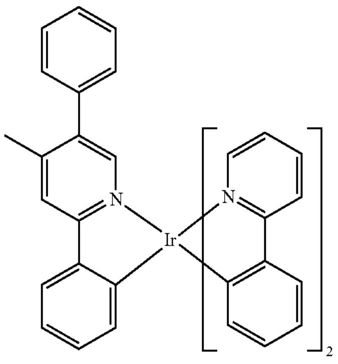

H1

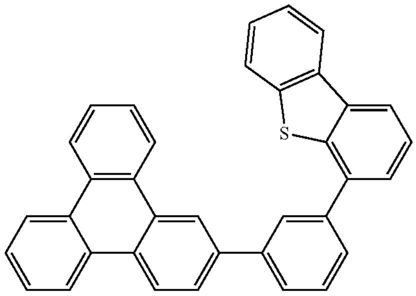

NPD

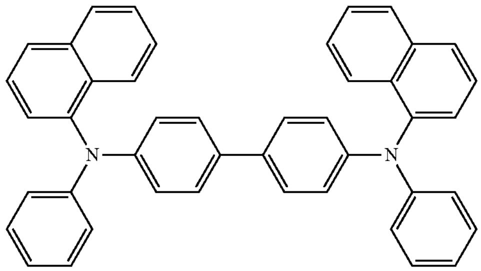

H2 is a compound available as NS60 from Nippon Steel Company (NSCC) of Tokyo, Japan.

TABLE 5

| Example | HIL | HTL | Host | A % | BL | ETL |
|---|---|---|---|---|---|---|
| Example 12 | E1 100 Å | NPD 300 Å | H2 | Compound 1 10% | H2 100 Å | Alq 400 Å |
| Example 13 | E1 100 Å | NPD 300 Å | H2 | Compound 2 7% | H2 100 Å | Alq 400 Å |
| Example 14 | E1 100 Å | NPD 300 Å | H2 | Compound 2 10% | H2 100 Å | Alq 400 Å |
| Example 15 | E1 100 Å | NPD 300 Å | H2 | Compound 4 10% | H2 100 Å | Alq 400 Å |
| Example 16 | E1 100 Å | NPD 300 Å | H2 | Compound 7 10% | H2 100 Å | Alq 400 Å |
| Example 17 | E1 100 Å | NPD 300 Å | H2 | Compound 10 10% | H2 100 Å | Alq 400 Å |
| Example 18 | E1 100 Å | NPD 300 Å | H2 | Compound 29 10% | H2 100 Å | Alq 400 Å |
| Example 19 | E3 100 Å | NPD 300 Å | H1 | Compound 37 7% | H1 100 Å | Alq 400 Å |
| Example 20 | E3 100 Å | NPD 300 Å | H1 | Compound 37 10% | H1 100 Å | Alq 400 Å |
| Example 21 | E3 100 Å | NPD 300 Å | H2 | Compound 37 10% | H2 100 Å | Alq 400 Å |

TABLE 6

| | | | | At 1000 nits | | | | At 40 mA/cm$^2$ | |
|---|---|---|---|---|---|---|---|---|---|
| | λ | CIE | | V | LE | EQE | PE | Lo, | $RT_{80\%}$, |
| Example | max, nm | X | Y | (V) | (cd/A) | (%) | (lm/W) | nits | h |
| Ex. 12 | 530 | 0.361 | 0.612 | 4.1 | 78.6 | 20.9 | 60.0 | 24,069 | 220 |
| Ex. 13 | 526 | 0.354 | 0.615 | 4.7 | 48.9 | 13.1 | 33.0 | 14,002 | 210 |
| Ex. 14 | 527 | 0.349 | 0.620 | 4.9 | 49.8 | 13.3 | 31.6 | 14,510 | 190 |
| Ex. 15 | 528 | 0.363 | 0.612 | 5.1 | 67.8 | 18 | 42.1 | 21,146 | 116 |
| Ex. 16 | 522 | 0.334 | 0.626 | 4.8 | 65.9 | 17.8 | 43.1 | 20,136 | 170 |
| Ex. 17 | 522 | 0.333 | 0.627 | 5.7 | 62.1 | 16.7 | 34.0 | 18,581 | 98 |
| Ex. 18 | 576 | 0.542 | 0.455 | 6.4 | 36.2 | 13.9 | 17.9 | 10,835 | 740 |
| Ex. 19 | 532 | 0.386 | 0.593 | 5.6 | 67.8 | 18.5 | 37.9 | 21,426 | 98 |
| Ex. 20 | 532 | 0.386 | 0.593 | 5.7 | 67.7 | 18.5 | 37.5 | 21,050 | 103 |
| Ex. 21 | 532 | 0.380 | 0.598 | 6.5 | 54.8 | 14.8 | 26.7 | 16,798 | 315 |

From Device Examples 12-21, it can be seen that the invention compounds as emitting dopants in green phosphorescent devices provide devices with high efficiency and long lifetimes. In particular, the lifetime, $RT_{80\%}$ (defined as the time for the initial luminance, $L_0$, to decay to 80% of its value, at a constant current density of 40 mA/cm$^2$ at room temperature) of devices containing Compounds 29 and 37 are notably higher than those measured for the Comparative Examples. In particular, Compound 29 in Device Example 18 and Compound 37 in Device Example 21 measured 740 h and 315 h, respectively. Devices with Compound 1 in H2, as shown in Example 12, had exceptionally high efficiency, 78.6 cd/A and long lifetime. It is unexpected that Compound 1 worked extremely well in H2. Additionally, Compounds 1, 4, 7, 29, and 37 in Device Examples 12, 15, 17, 19, and 20, respectively, achieved high device efficiency (i.e., LE of greater than 60 cd/A at 1000 cd/m$^2$), indicating that the inventive compounds comprising a single substituted pyridyl ligand (e.g., pyridyl dibenzofuran) have a high enough triplet energy for efficient green electrophosphorescence.

The above data suggests that the heteroleptic iridium complexes provided herein can be excellent emitting dopants for phosphorescent OLEDs, providing devices having improved efficiency and longer lifetime that may also have improved manufacturing.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

FORMULA I

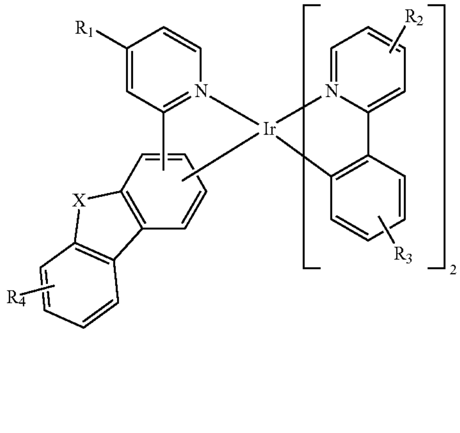

, wherein X is selected from the group consisting of O and S;

wherein $R_2$, $R_3$, and $R_4$ may represent mono, di, tri, or tetra substitutions;

wherein $R_1$ is alkyl;

wherein each of $R_2$, $R_3$, and $R_4$ are independently selected from the group consisting of hydrogen, alkyl, and aryl.

2. The compound of claim 1, wherein $R_4$ is selected from the group consisting of hydrogen and alkyl having four or fewer carbon atoms.

3. The compound of claim 1, wherein $R_4$ is selected from the group consisting of hydrogen and methyl.

4. The compound of claim 1, wherein $R_4$ is selected from the group consisting of hydrogen, alkyl having four or fewer carbon atoms and aryl with 5 or 6 atoms in the ring.

5. The compound of claim 1, wherein $R_2$ and $R_3$ are independently selected from the group consisting of hydrogen, methyl and phenyl.

6. The compound of claim 1, wherein $R_2$ and $R_3$ are hydrogen.

7. The compound of claim 1, wherein $R_2$, $R_3$, and $R_4$ are independently selected from the group consisting of hydrogen, alkyl having four or fewer carbon atoms and aryl with 5 or 6 fewer atoms in the ring.

8. The compound of claim 1, wherein $R_2$, $R_3$, and $R_4$ are independently selected from the group consisting of hydrogen, methyl and phenyl.

9. The compound of claim 1, wherein $R_2$, $R_3$, and $R_4$ are hydrogen.

10. The compound of claim 1, wherein the compound has the formula:

FORMULA III

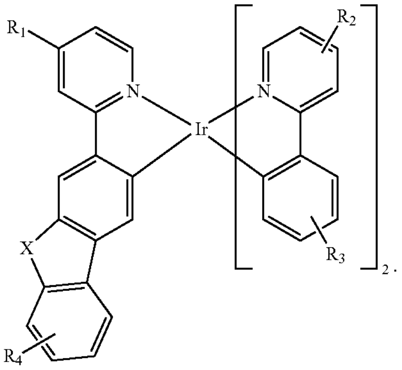

11. The compound of claim 1, wherein the compound has the formula:

FORMULA IV

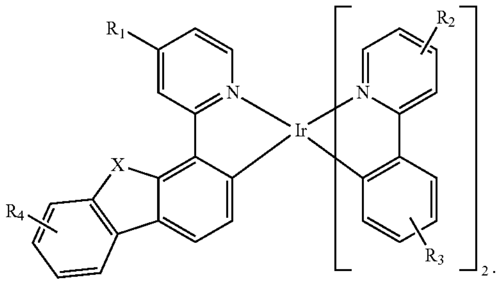

12. The compound of claim 1, wherein the compound has the formula:

FORMULA V

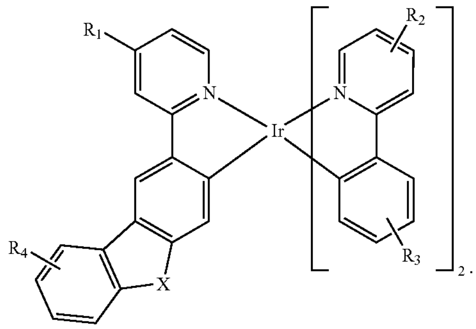

13. The compound of claim 1, wherein the compound is selected from the group consisting of:

Compound 7

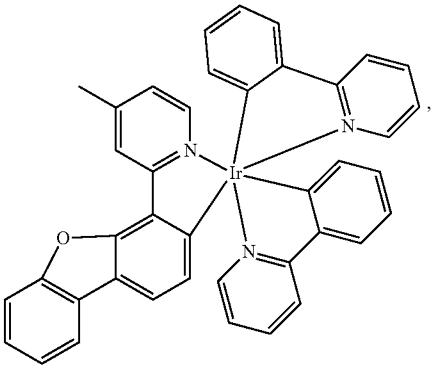

Compound 8

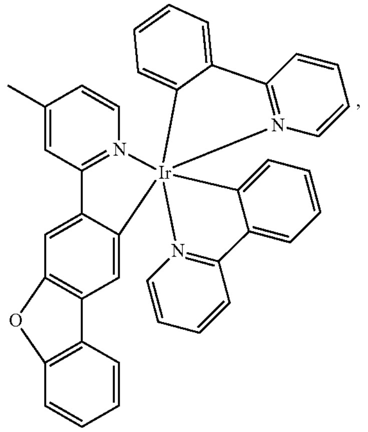

-continued
Compound 9
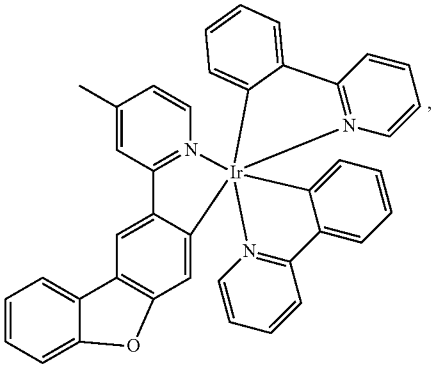
Compound 10
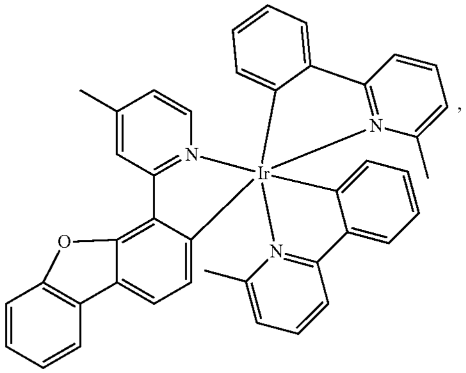
Compound 11
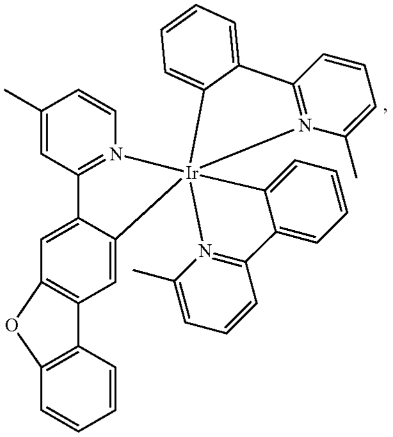
Compound 12
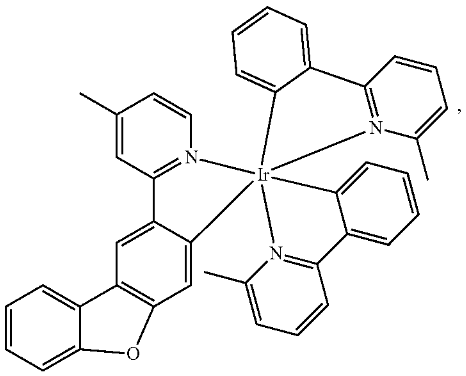
-continued
Compound 19
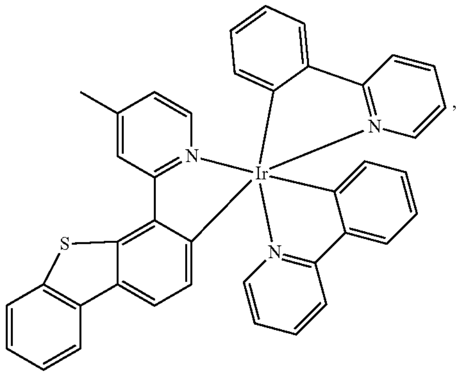
Compound 20
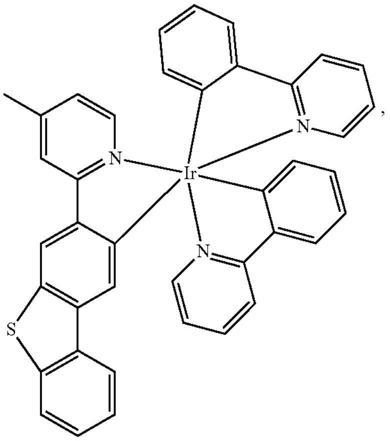
Compound 21
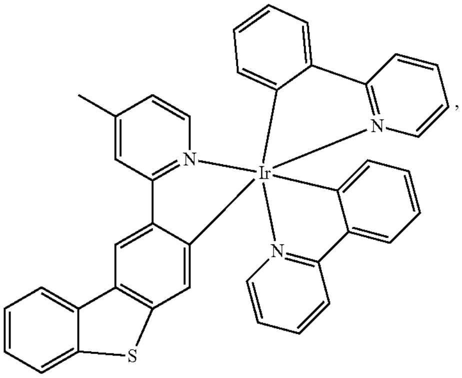
Compound 22
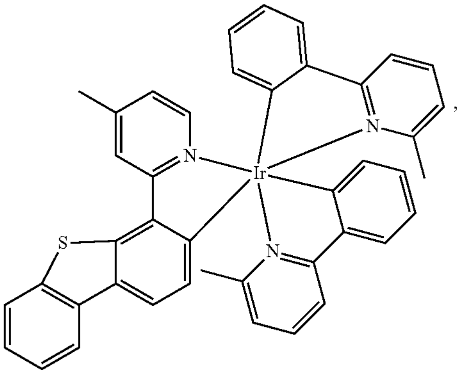

-continued
Compound 23
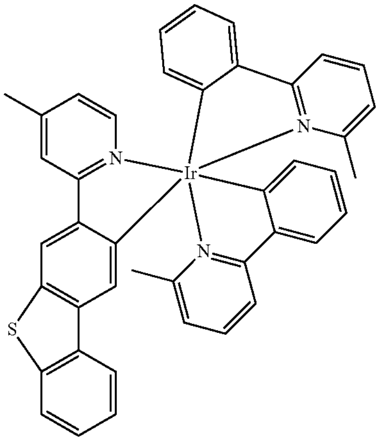
, and
Compound 24
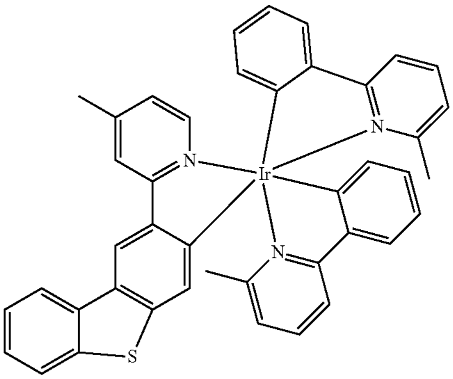
.
14. The compound of claim 1, wherein the compound is selected from the group consisting of:
Compound 40
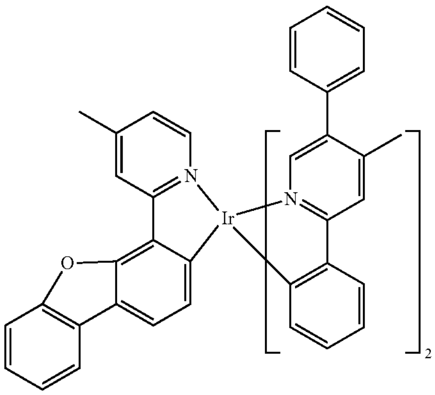
,
-continued
Compound 41
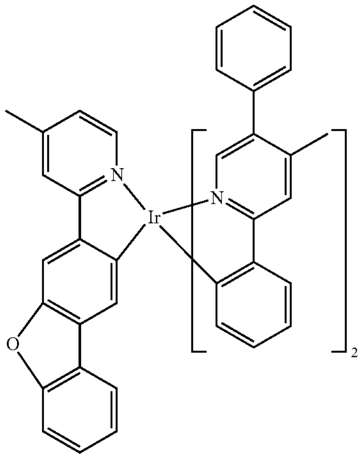
,
Compound 42
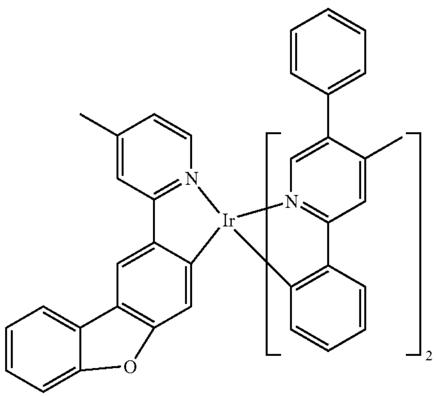
,
Compound 49
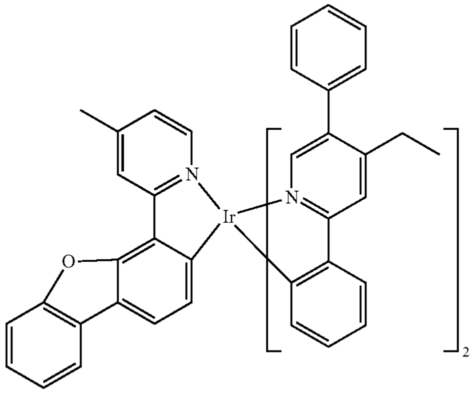
, -continued
Compound 50
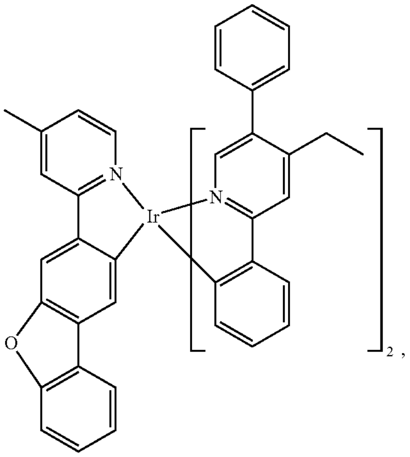
Compound 51
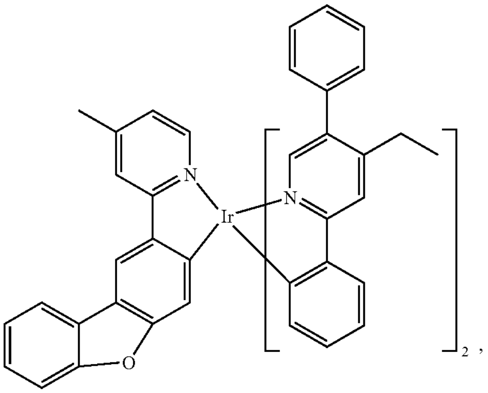
Compound 64
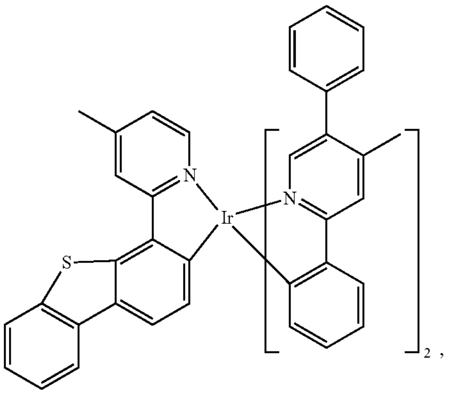
-continued
Compound 65
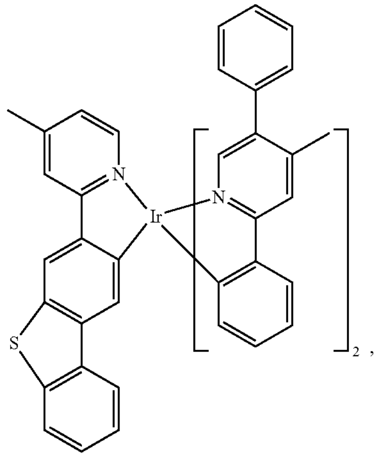
Compound 66
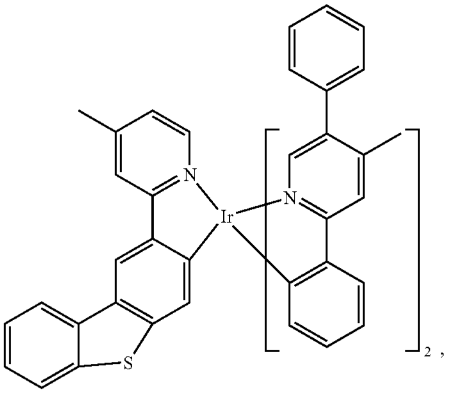
Compound 73
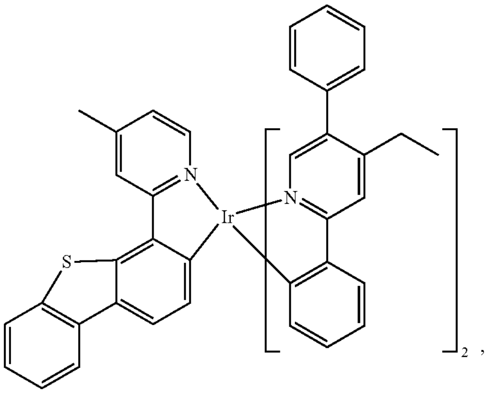

-continued
Compound 74
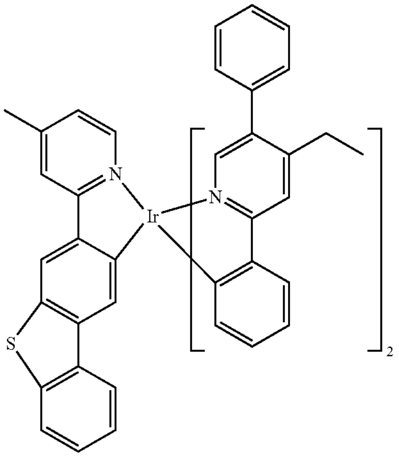
, and
Compound 75
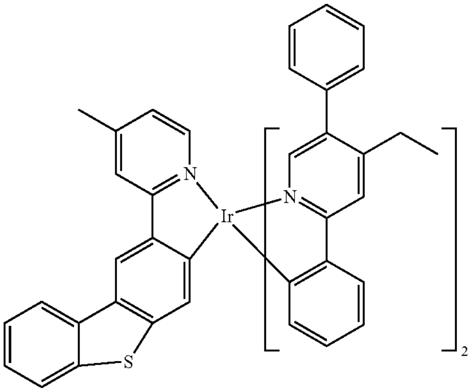
.
15. The compound of claim 1, wherein X is O.
16. The compound of claim 15, wherein the compound is selected from the group consisting of:
Compound 7
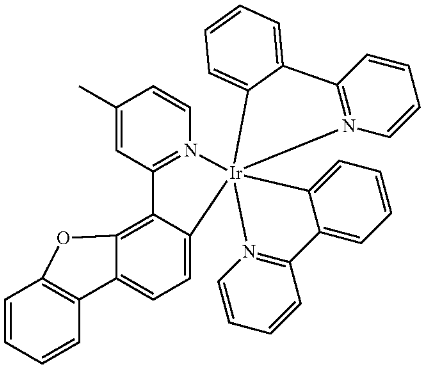
,
-continued
Compound 8
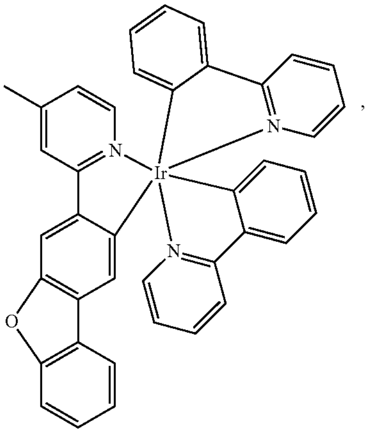
,
Compound 9
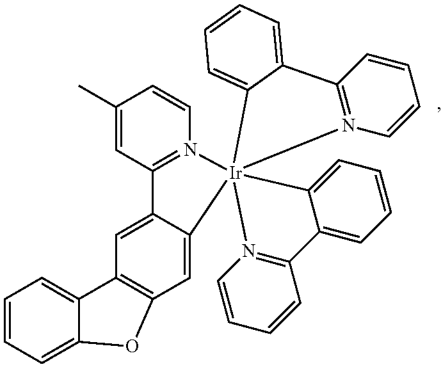
,
Compound 10
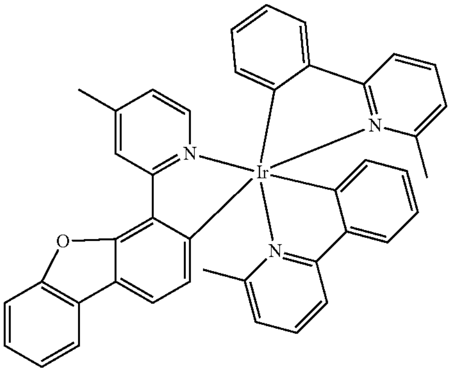
, -continued
Compound 11
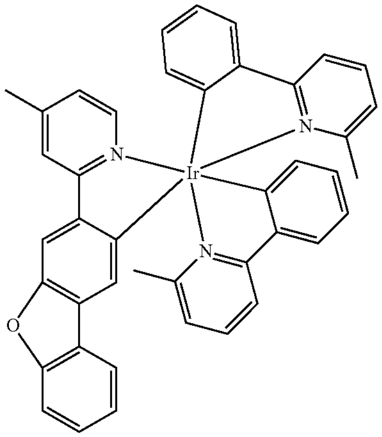
, and
Compound 12
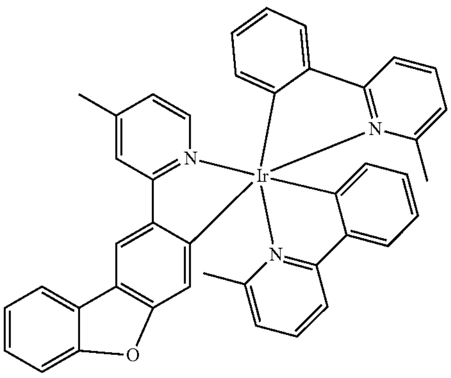
.
17. The compound of claim 15, wherein the compound is selected from the group consisting of:
Compound 40
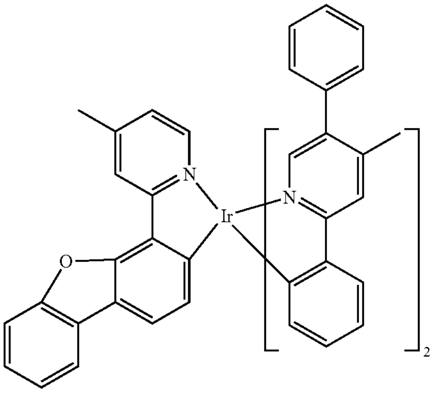
,
-continued
Compound 41
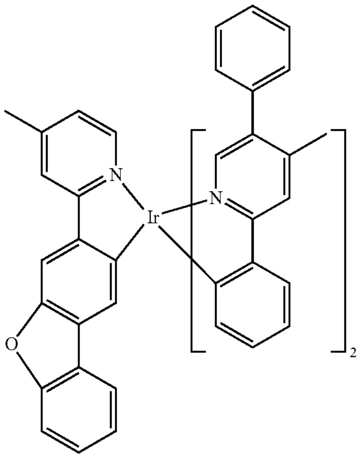
,
Compound 42
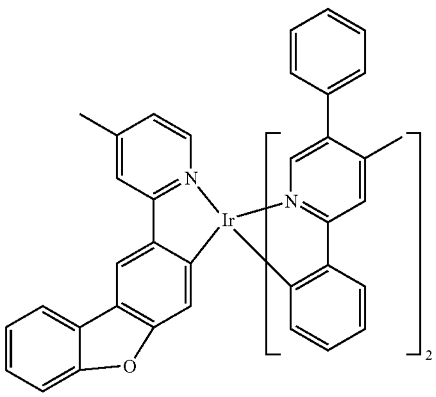
,
Compound 49
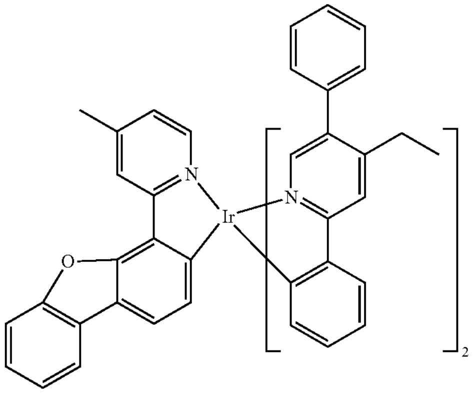
, -continued
Compound 50
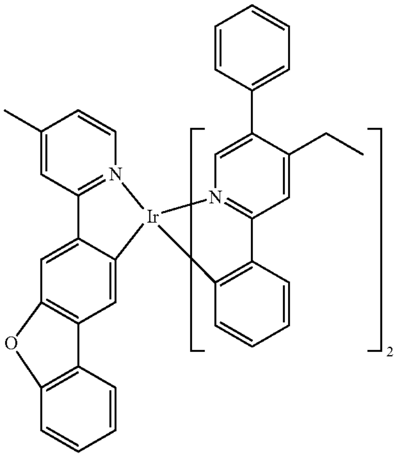
, and
Compound 51
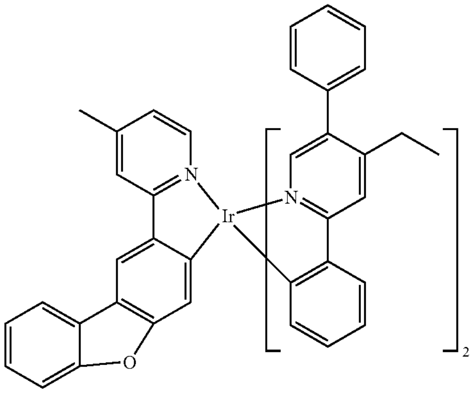
.
18. The compound of claim 15, wherein the compound is selected from the group consisting of:
Compound 7
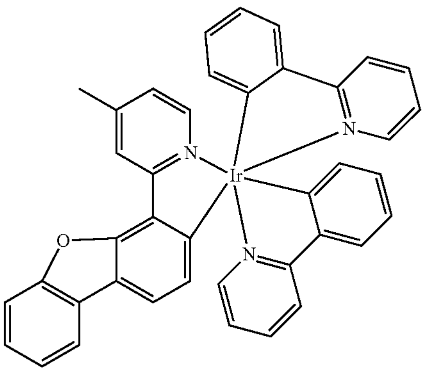
,
-continued
Compound 8
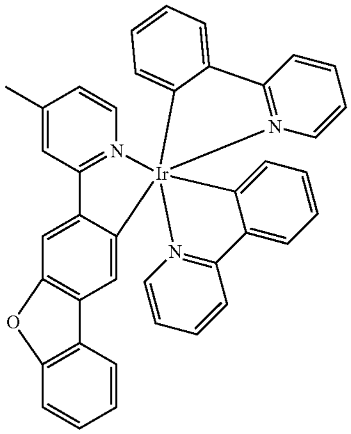
,
Compound 9
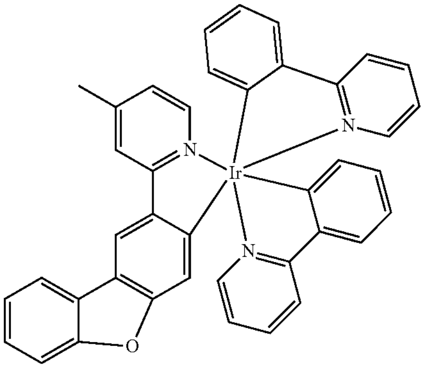
,
Compound 10
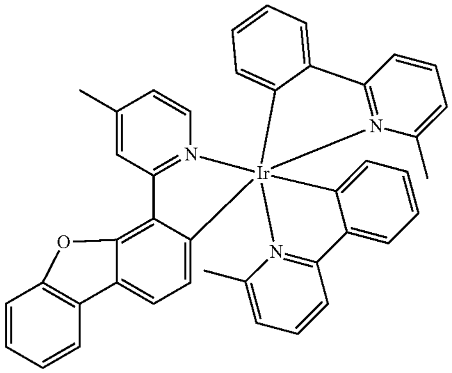
, -continued
Compound 11
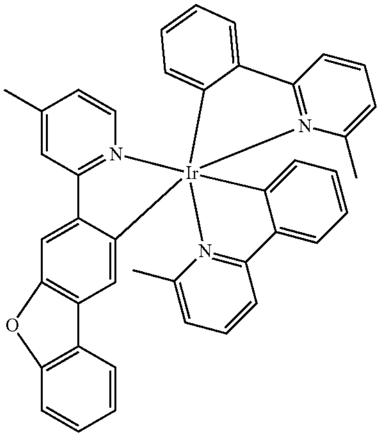
,
Compound 12
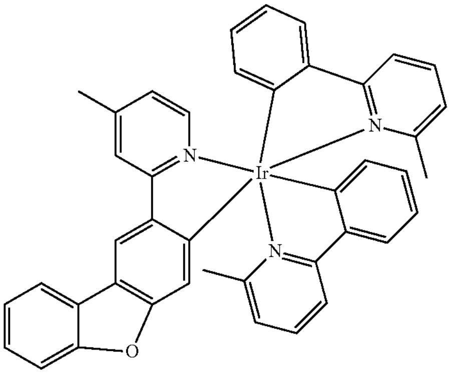
,
Compound 40
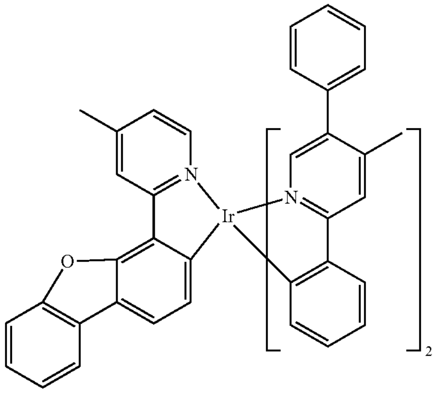
,
-continued
Compound 41
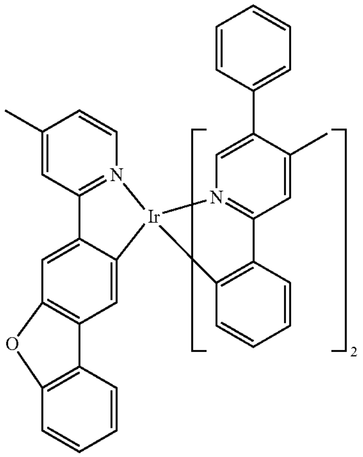
,
Compound 42
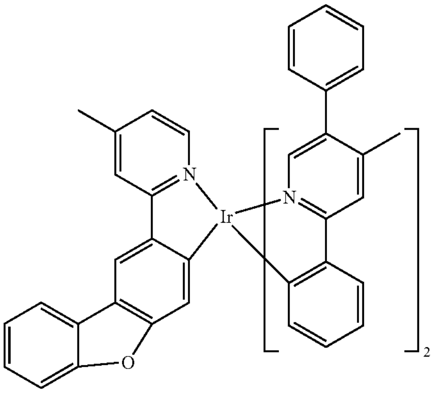
,
Compound 49
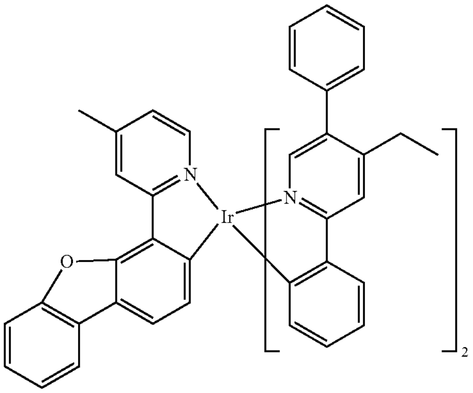
, -continued
Compound 50
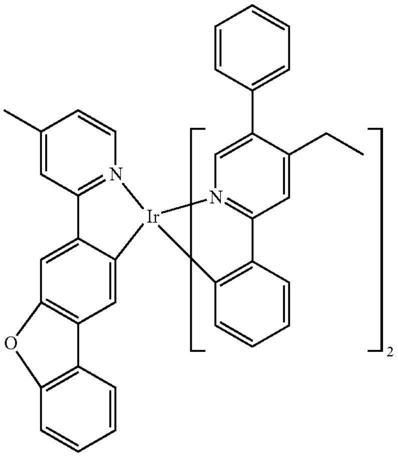
, and
Compound 51
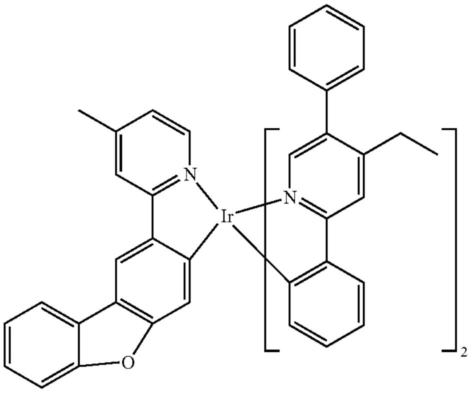
.
19. The compound of claim 1, wherein X is S.
20. The compound of claim 19, wherein the compound is selected from the group consisting of:
Compound 19
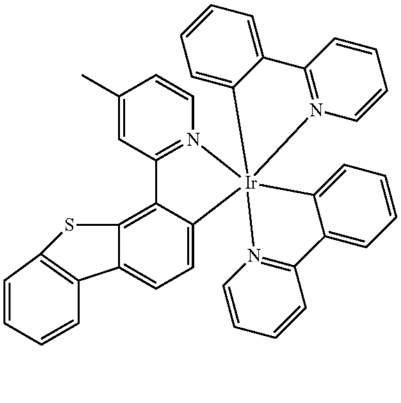
,
-continued
Compound 20
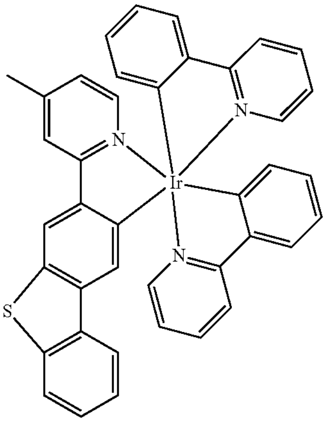
,
Compound 21
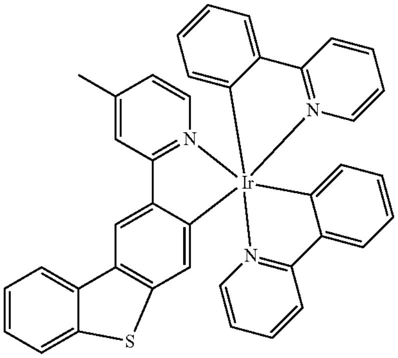
,
Compound 22
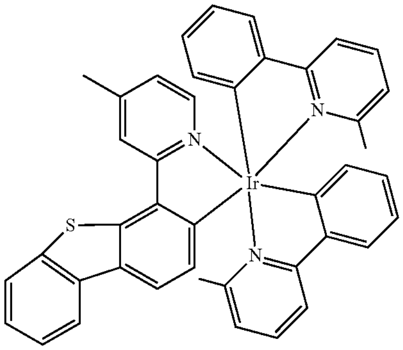
,
Compound 23
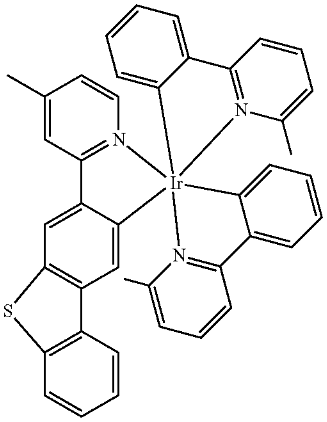
, and -continued
Compound 24
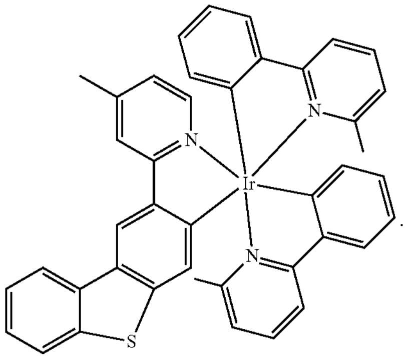
21. The compound of claim 19, wherein the compound is selected from the group consisting of:
Compound 67
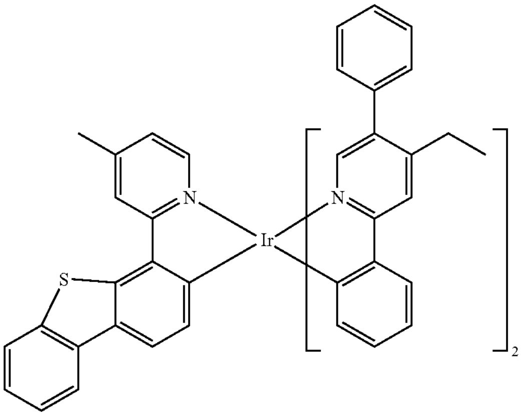
,
Compound 68
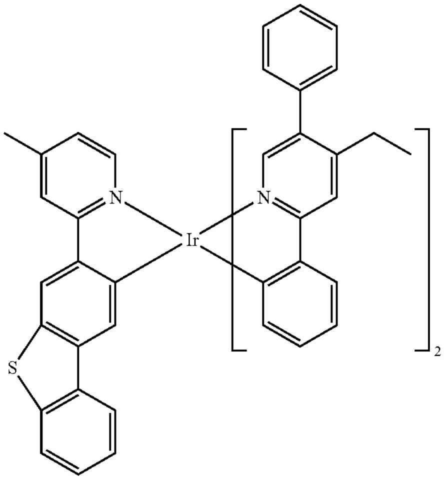
,
-continued
Compound 69
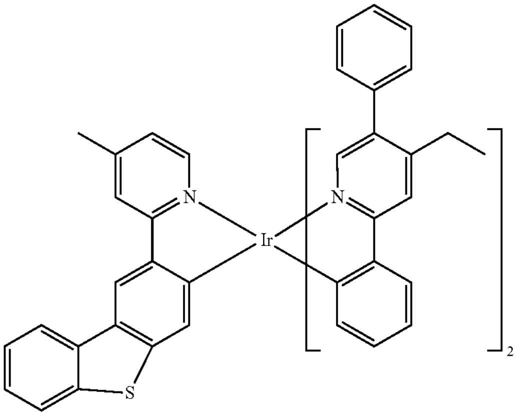
,
Compound 73
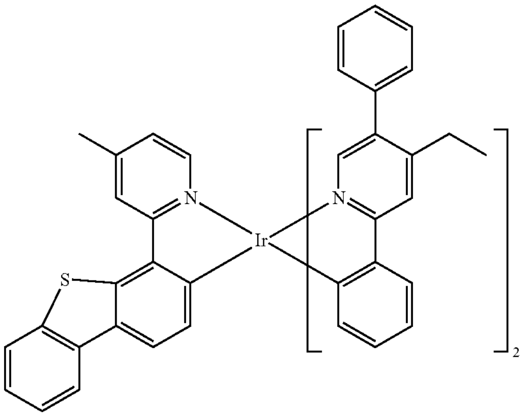
,
Compound 74
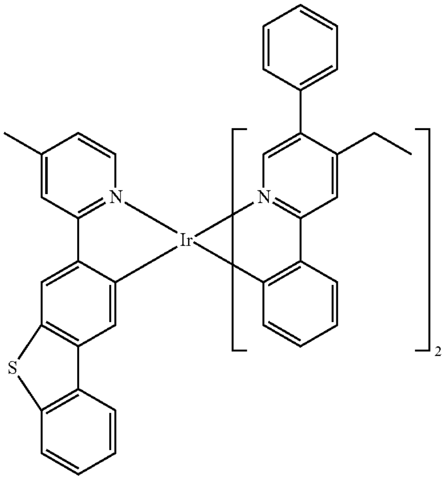
, and -continued
Compound 75
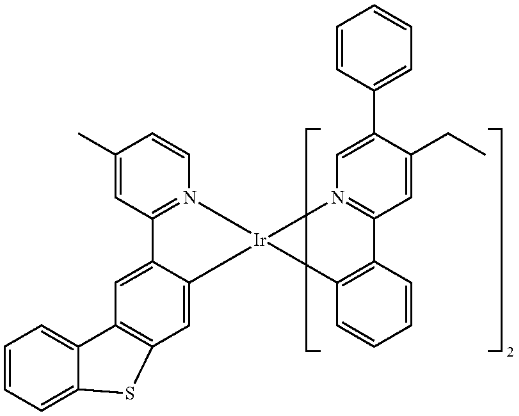
.
22. The compound of claim 19, wherein the compound is selected from the group consisting of:
Compound 19
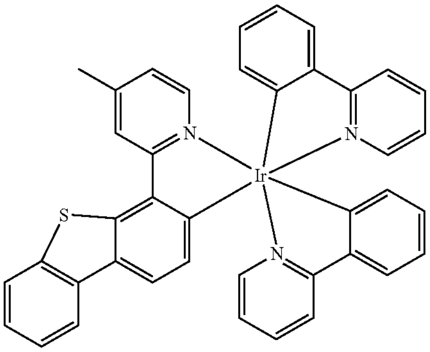
,
Compound 20
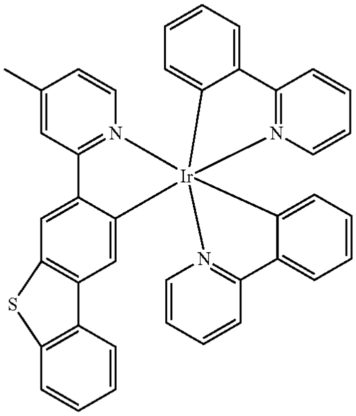
,
-continued
Compound 21
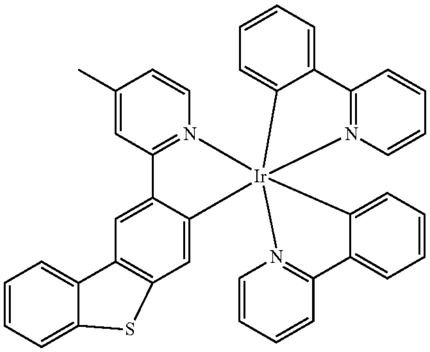
,
Compound 22
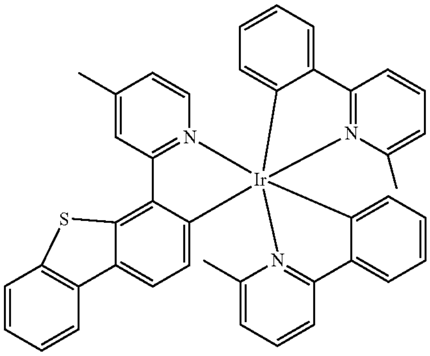
,
Compound 23
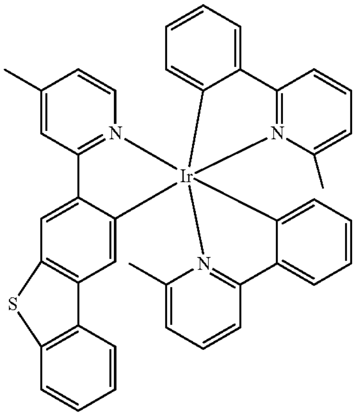
,
Compound 24
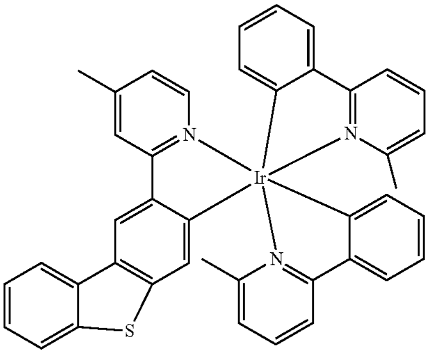
, -continued
Compound 67
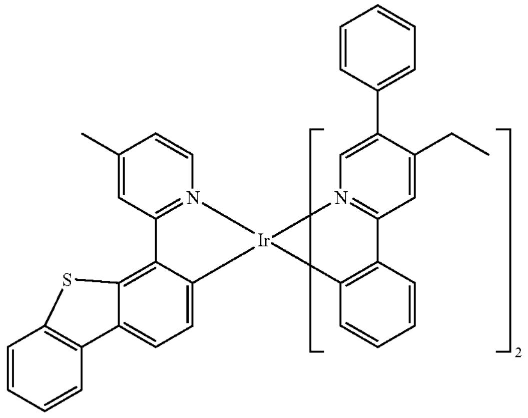
,
Compound 68
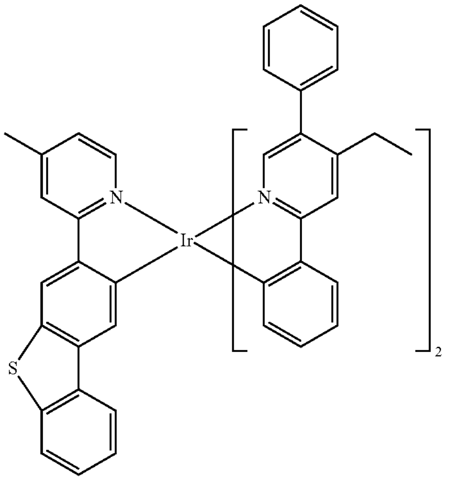
,
Compound 69
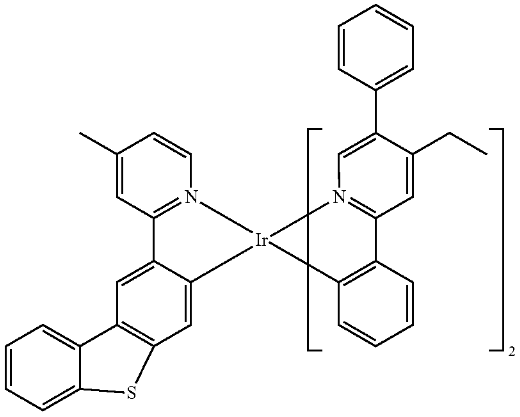
,
-continued
Compound 73
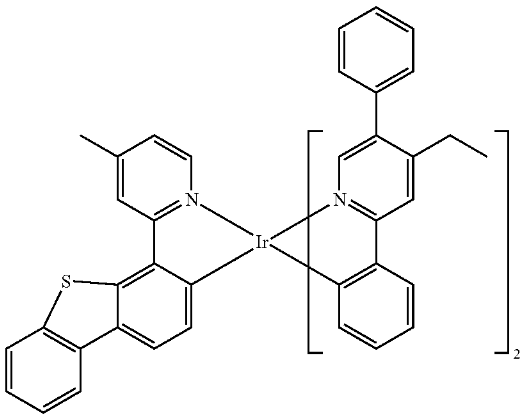
,
Compound 74
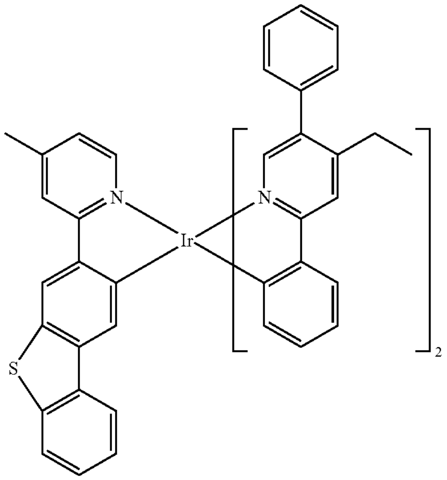
, and
Compound 75
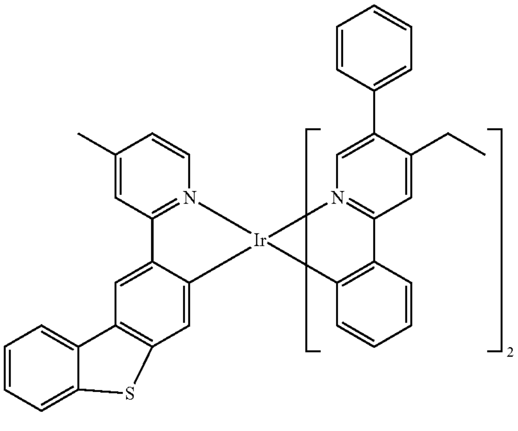
.

23. The compound of claim 1, wherein $R_1$ is an alkyl having four or fewer carbon atoms.

24. The compound of claim 1, wherein $R_1$ is methyl.

25. The compound of claim 1 wherein $R_2$ and $R_3$ are independently selected from the group consisting of hydrogen, alkyl having four or fewer carbon atoms, and aryl with 5 or 6 atoms in a ring.

26. A first device comprising an organic light emitting device, comprising:

an anode;

a cathode; and an organic layer, disposed between the anode and the cathode, the organic layer comprising a heteroleptic iridium complex having the formula:

FORMULA I

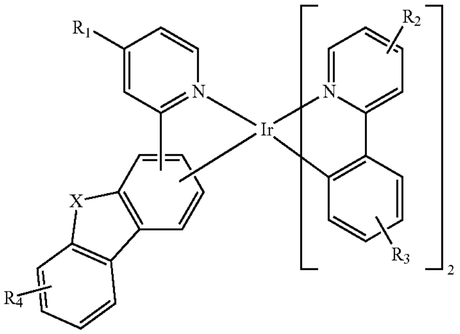
, wherein X is selected from the group consisting of O and S;

wherein $R_2$, $R_3$ and $R_4$ may represent mono, di, tri, or tetra substitutions;

wherein $R_1$ is alkyl;

wherein each of $R_2$, $R_3$ and $R_4$ are independently selected from the group consisting of hydrogen, alkyl, and aryl.

27. The device of claim 26, wherein the first device is a consumer product.

28. The device of claim 26, wherein $R_2$ and $R_3$ are independently selected from the group consisting of hydrogen, alkyl having four or fewer carbon atoms and aryl with 5 or 6 atoms in the ring.

29. The device of claim 26, wherein the compound is selected from the group consisting of:

Compound 7

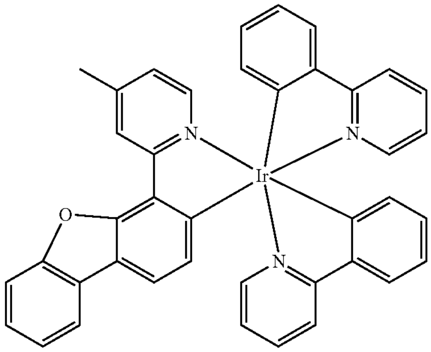
,

-continued

Compound 8

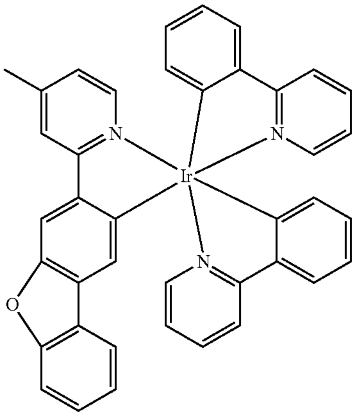
,

Compound 9

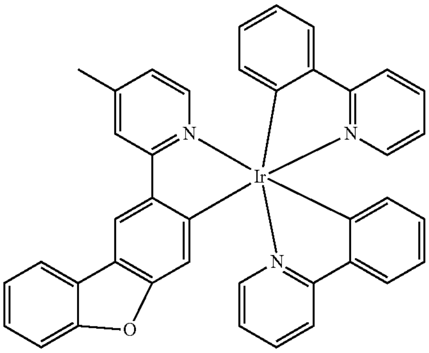
,

Compound 10

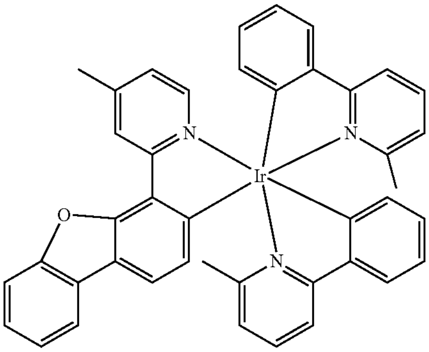
,

Compound 11

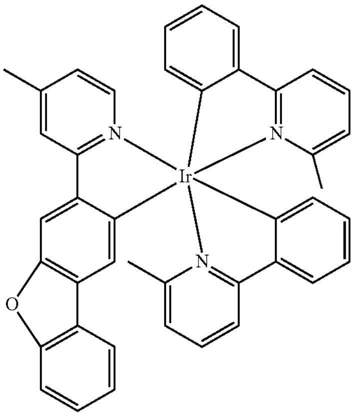
,

-continued
Compound 12
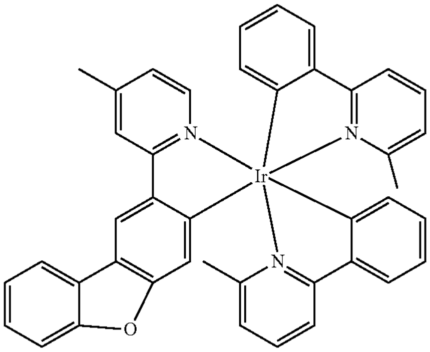
,
Compound 19
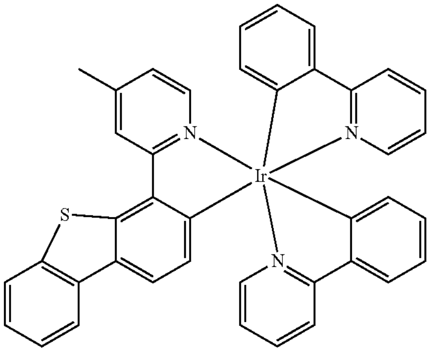
,
Compound 20
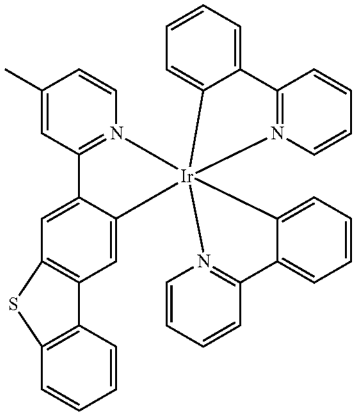
,
Compound 21
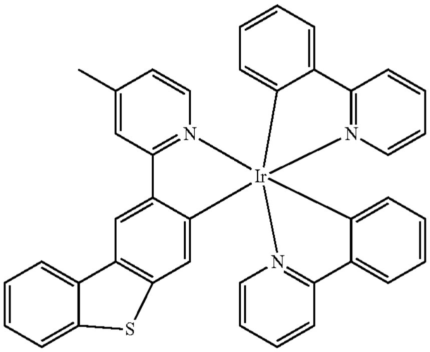
,
-continued
Compound 22
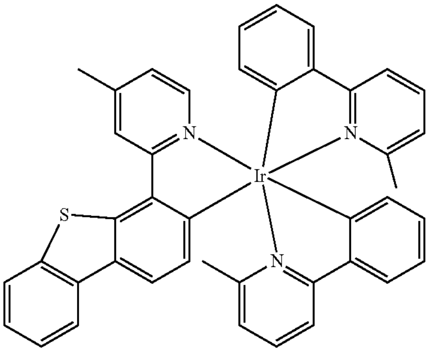
,
Compound 23
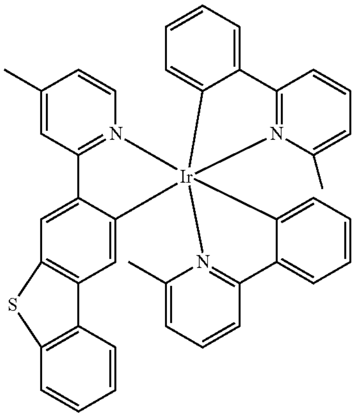
, and
Compound 24
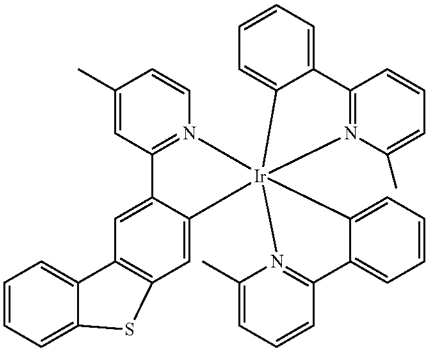
.

30. The device of claim 26, wherein the compound is selected from the group consisting of:
Compound 40
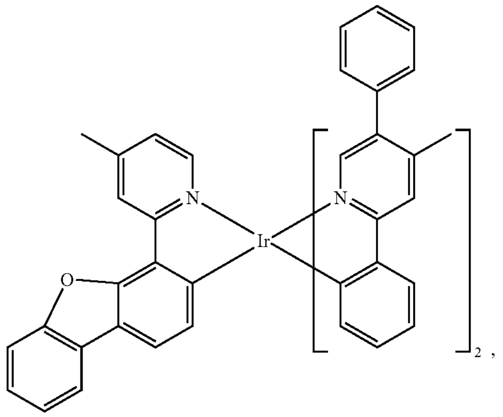
Compound 41
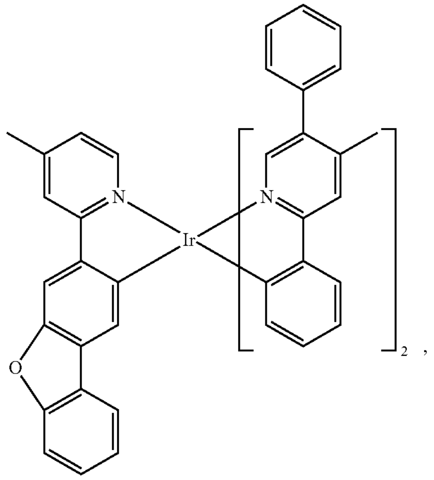
Compound 42
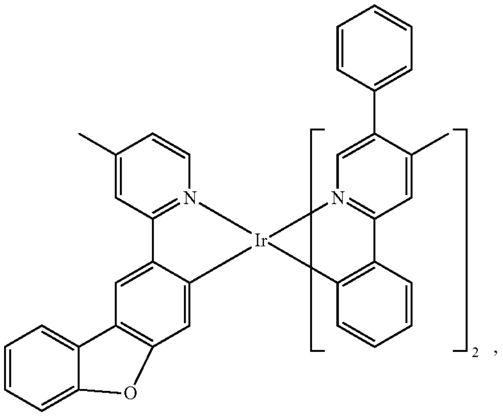
-continued
Compound 49
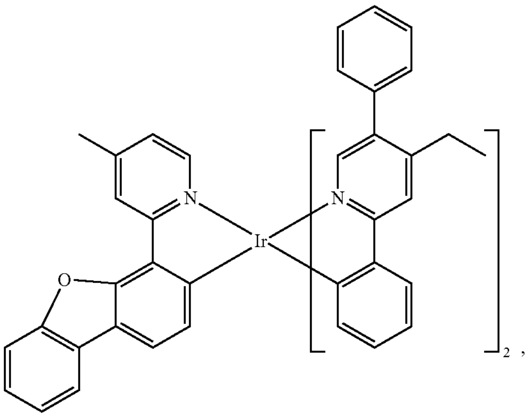
Compound 50
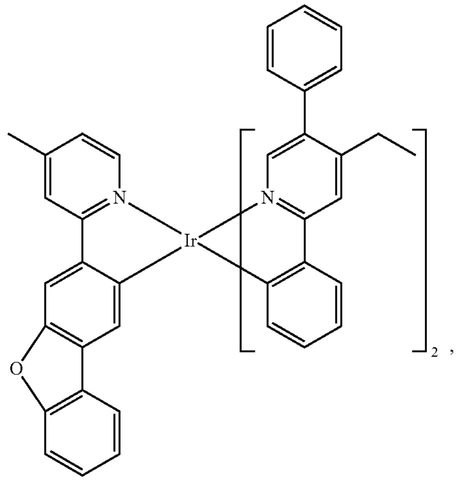
Compound 51
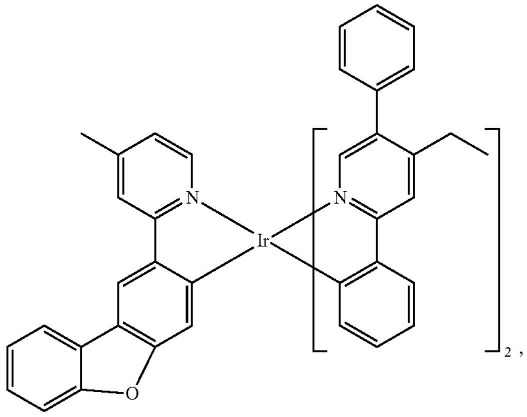

-continued
Compound 64
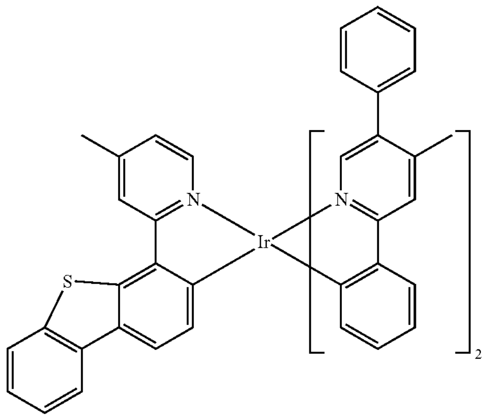
2 ,
Compound 65
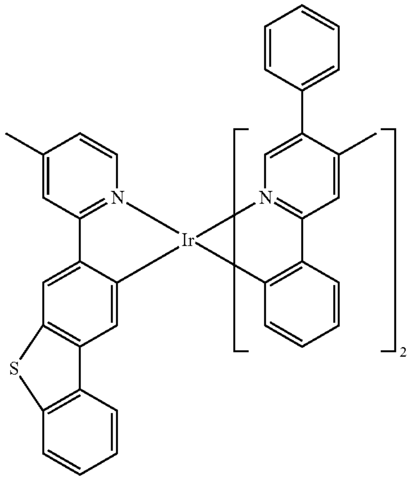
2 ,
Compound 66
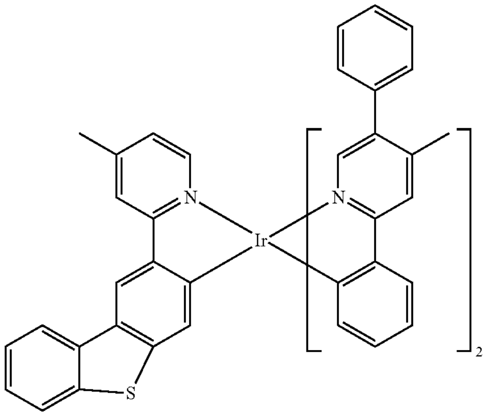
2 ,
-continued
Compound 73
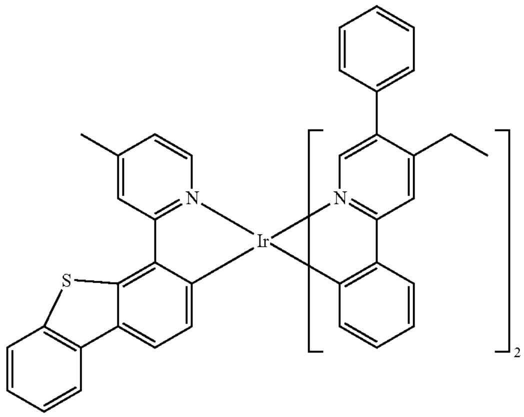
2 ,
Compound 74
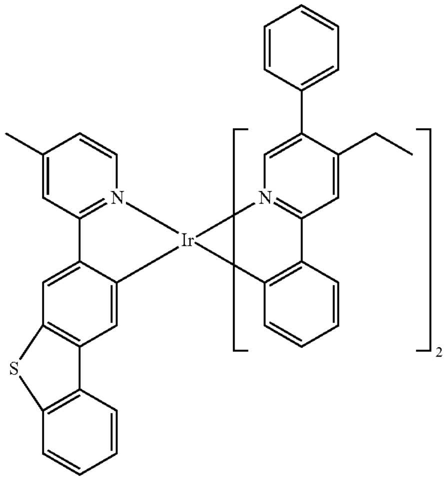
2 , and
Compound 75
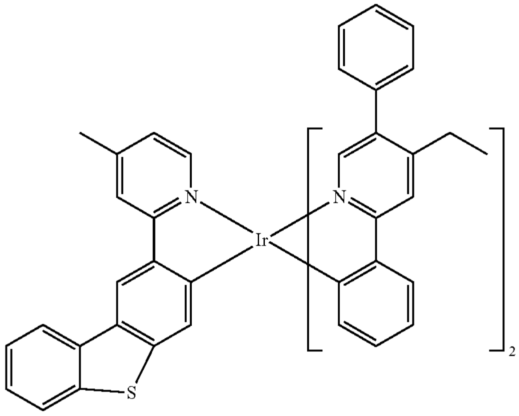
2 .
31. The device of claim 26, wherein the organic layer is an emissive layer and the compound having the formula:

FORMULA I

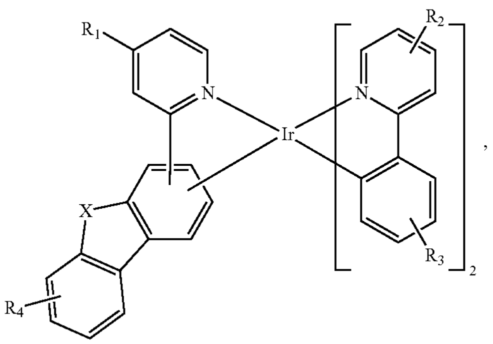

is an emitting dopant.

32. The device of claim 26, wherein the organic layer further comprises a host.

33. The device of claim 32, wherein the host comprises a triphenylene moiety and a dibenzothiophene moiety.

34. The device of claim 33, wherein the host has the formula:

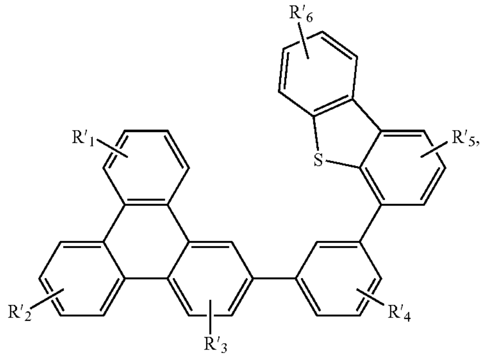

wherein $R'_1$, $R'_2$, $R'_4$, and $R'_6$ may represent mono, di, tri, or tetra substitutions;

wherein $R'_3$, and $R_5'$ may represent mono, di, or tri substitutions; and wherein each of $R'_1$, $R'_2$, $R'_3$, $R'_4$, $R'_5$, and $R'_6$ are independently selected from the group consisting of hydrogen, alkyl, and aryl.

35. A compound having the formula:

FORMULA IV

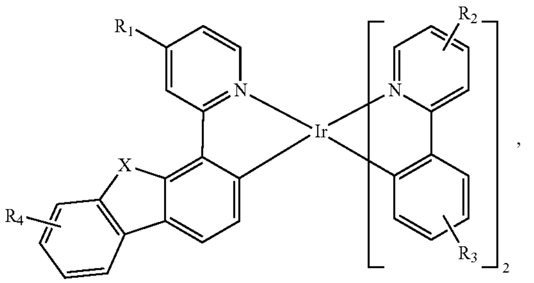

wherein X is selected from the group consisting of NR, O, S, BR, and Se;

wherein R is selected from hydrogen and alkyl;

wherein $R_2$, $R_3$, and $R_4$ may represent mono, di, tri, or tetra substitutions;

wherein $R_1$ is alkyl;

wherein each of $R_2$, $R_3$, and $R_4$ are independently selected from the group consisting of hydrogen, alkyl, and aryl.

36. The compound of claim 35, wherein X is NR.

37. The compound of claim 35, wherein the compound is selected from the group consisting of:

Compound 31

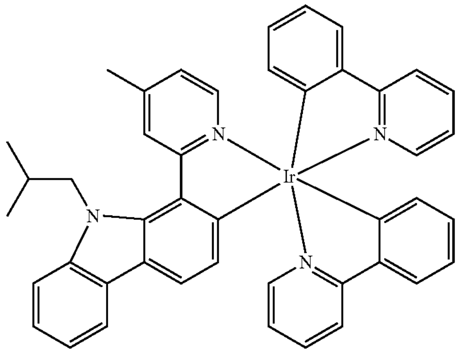

and

Compound 34

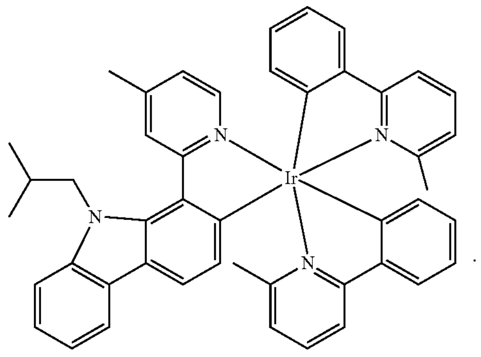

.

38. The compound of claim 35, wherein the compound is selected from the group consisting of:

Compound 85

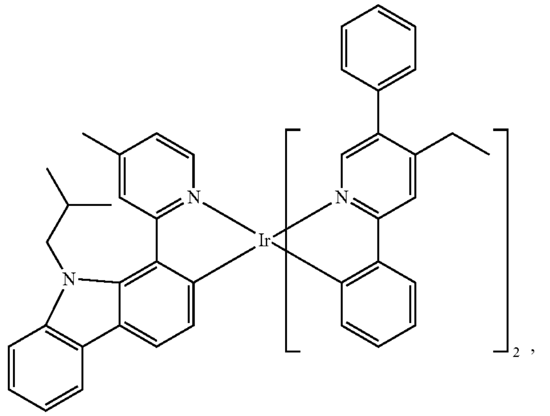

-continued
Compound 88
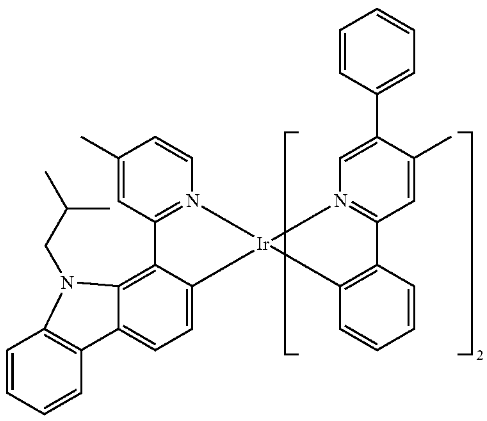
, and
Compound 97
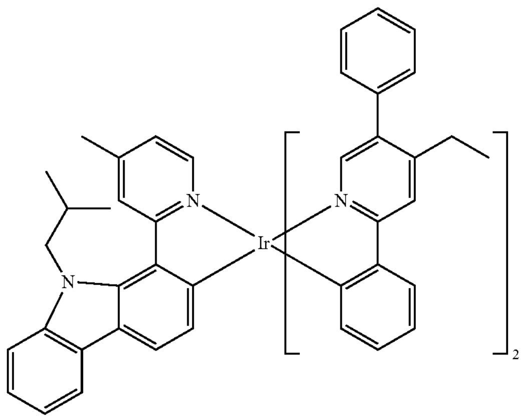
.
39. The compound of claim 35, wherein the compound is selected from the group consisting of:
Compound 31
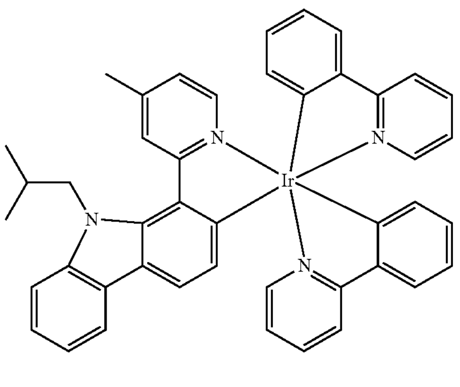
,
-continued
Compound 34
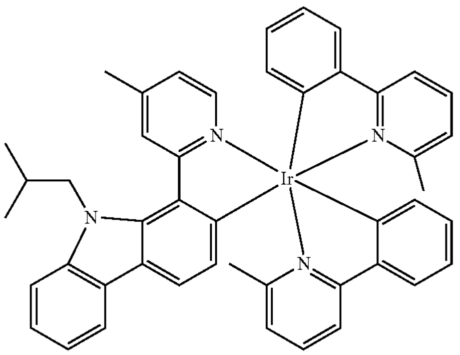
,
Compound 85
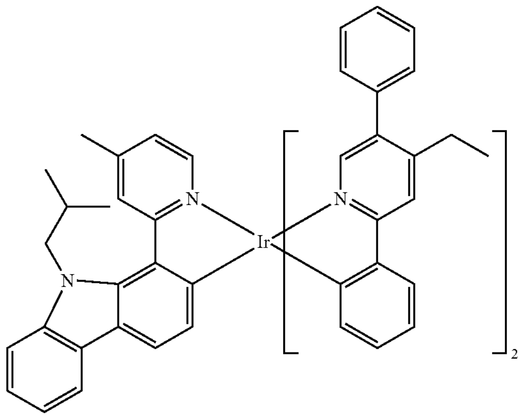
,
Compound 88
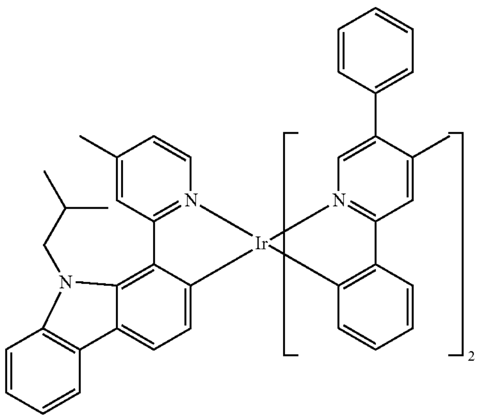
, and -continued
Compound 97
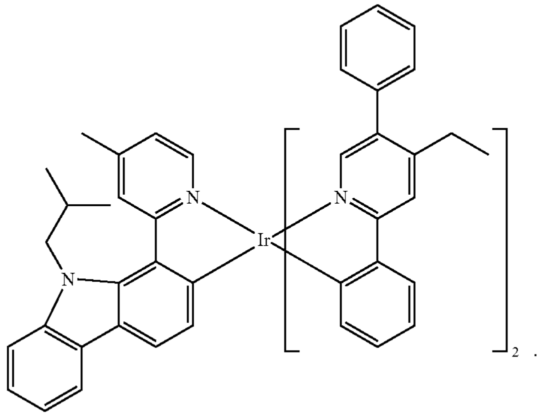
* * * * *